United States Patent
Banet et al.

(10) Patent No.: US 10,722,131 B2
(45) Date of Patent: *Jul. 28, 2020

(54) BODY-WORN SYSTEM FOR CONTINUOUS, NONINVASIVE MEASUREMENT OF CARDIAC OUTPUT, STROKE VOLUME, CARDIAC POWER, AND BLOOD PRESSURE

(75) Inventors: Matt Banet, Kihei, HI (US); Isaac Henry, La Mesa, CA (US); Donald Bernstein, Rancho Santa Fe, CA (US)

(73) Assignee: SOTERA WIRELESS, INC., San Diego, CA (US)

( * ) Notice: Subject to any disclaimer, the term of this patent is extended or adjusted under 35 U.S.C. 154(b) by 1258 days.

This patent is subject to a terminal disclaimer.

(21) Appl. No.: 13/338,228

(22) Filed: Dec. 27, 2011

(65) Prior Publication Data

US 2014/0249431 A1  Sep. 4, 2014

Related U.S. Application Data

(60) Provisional application No. 61/427,756, filed on Dec. 28, 2010.

(51) Int. Cl.
*A61B 5/0295* (2006.01)
*A61B 5/029* (2006.01)
(Continued)

(52) U.S. Cl.
CPC .......... *A61B 5/0295* (2013.01); *A61B 5/0008* (2013.01); *A61B 5/0022* (2013.01);
(Continued)

(58) Field of Classification Search
None
See application file for complete search history.

(56) References Cited

U.S. PATENT DOCUMENTS 4,263,918 A  4/1981  Swearingen et al.
4,270,547 A  6/1981  Steffen et al.
(Continued)

FOREIGN PATENT DOCUMENTS

EP  0443267 A1  8/1991
EP  0993803 A1  4/2000
(Continued)

OTHER PUBLICATIONS

Non-Final Office Action issued by the US Patent and Trademark Office dated Aug. 31, 2012 in U.S. Appl. No. 12/469,213.
(Continued)

*Primary Examiner* — Michael R Bloch
(74) *Attorney, Agent, or Firm* — Acuity Law Group, PC; Michael A. Whittaker

(57) ABSTRACT

The invention provides a system for measuring stroke volume (SV), cardiac output (CO), and cardiac power (CP) from a patient that features: 1) an impedance sensor connected to at least two body-worn electrodes and including an impedance circuit that processes analog signals from the electrodes to measure an impedance signal (e.g. TBEV waveform); 2) an ECG sensor connected to at least two chest-worn electrodes and including an ECG circuit that processes analog signals from the electrodes to measure and ECG signal; 3) an optical sensor connected to a body-worn optical probe and including an optical circuit that processes signals from the probe to measure at least one optical signal (e.g. a PPG waveform) from the patient; 4) a processing system, typically worn on the patient's wrist and connected through a wired interface to the optical sensor, and through either a wired or wireless interface to the TBEV and ECG sensors.

11 Claims, 38 Drawing Sheets

(51) Int. Cl.
  *A61B 5/053* (2006.01)
  *A61B 5/08* (2006.01)
  *A61B 5/11* (2006.01)
  *A61B 5/1455* (2006.01)
  *A61B 5/00* (2006.01)
  *A61B 5/01* (2006.01)
  *A61B 5/021* (2006.01)
  *A61B 5/02* (2006.01)
  *A61B 5/0205* (2006.01)
  *A61B 5/145* (2006.01)
  *G06F 19/00* (2018.01)
  *A61B 5/024* (2006.01)
  *A61B 5/0245* (2006.01)

(52) U.S. Cl.
  CPC ............... *A61B 5/01* (2013.01); *A61B 5/021* (2013.01); *A61B 5/0205* (2013.01); *A61B 5/029* (2013.01); *A61B 5/02028* (2013.01); *A61B 5/0535* (2013.01); *A61B 5/0816* (2013.01); *A61B 5/1116* (2013.01); *A61B 5/14542* (2013.01); *A61B 5/14551* (2013.01); *A61B 5/6823* (2013.01); *A61B 5/6824* (2013.01); *A61B 5/725* (2013.01); *A61B 5/746* (2013.01); *G06F 19/00* (2013.01); *A61B 5/0245* (2013.01); *A61B 5/02427* (2013.01); *A61B 5/681* (2013.01); *A61B 5/6826* (2013.01); *A61B 5/6833* (2013.01); *A61B 5/7239* (2013.01); *A61B 2562/04* (2013.01)

(56) References Cited

U.S. PATENT DOCUMENTS

| | | | |
|---|---|---|---|
| 4,305,400 A | 12/1981 | Logan | |
| 4,367,752 A | 1/1983 | Jimenez et al. | |
| 4,577,639 A | 3/1986 | Simon et al. | |
| 4,582,068 A | 4/1986 | Phillipps et al. | |
| 4,653,498 A | 3/1987 | New, Jr. et al. | |
| 4,710,164 A | 12/1987 | Levin et al. | |
| 4,722,351 A | 2/1988 | Phillipps et al. | |
| 4,802,486 A | 2/1989 | Goodman et al. | |
| 4,807,638 A | 2/1989 | Sramek | |
| 4,905,697 A | 3/1990 | Heggs et al. | |
| 5,025,791 A | 6/1991 | Niwa | |
| 5,140,990 A | 8/1992 | Jones et al. | |
| 5,190,038 A | 3/1993 | Polson et al. | |
| 5,197,489 A | 3/1993 | Conlan | |
| 5,247,931 A | 9/1993 | Norwood | |
| 5,316,008 A | 5/1994 | Suga et al. | |
| 5,339,818 A | 8/1994 | Baker et al. | |
| 5,435,315 A | 7/1995 | McPhee et al. | |
| 5,448,991 A | 9/1995 | Polson et al. | |
| 5,465,082 A | 11/1995 | Chaco | |
| 5,482,036 A | 1/1996 | Diab et al. | |
| 5,485,838 A | 1/1996 | Ukawa et al. | |
| 5,490,505 A | 2/1996 | Diab et al. | |
| 5,515,858 A | 5/1996 | Myllymaki | |
| 5,517,988 A | 5/1996 | Gerhard | |
| 5,524,637 A | 6/1996 | Erickson | |
| 5,549,650 A | 8/1996 | Bornzin et al. | |
| 5,575,284 A | 11/1996 | Athan et al. | |
| 5,577,508 A | 11/1996 | Medero | |
| 5,588,427 A | 12/1996 | Tien | |
| 5,593,431 A | 1/1997 | Sheldon | |
| 5,632,272 A | 5/1997 | Diab et al. | |
| 5,649,543 A | 7/1997 | Hosaka et al. | |
| 5,680,870 A | 10/1997 | Hood et al. | |
| 5,685,299 A | 11/1997 | Diab et al. | |
| 5,709,205 A | 1/1998 | Bukta | |
| 5,743,856 A | 4/1998 | Oka et al. | |
| 5,766,131 A | 6/1998 | Kondo et al. | |
| 5,769,785 A | 6/1998 | Diab et al. | |
| 5,800,349 A | 9/1998 | Isaacson et al. | |
| 5,820,550 A | 10/1998 | Polson et al. | |
| 5,848,373 A | 12/1998 | Delorme et al. | |
| 5,853,370 A | 12/1998 | Chance et al. | |
| 5,857,975 A | 1/1999 | Golub | |
| 5,865,755 A | 2/1999 | Golub | |
| 5,865,756 A | 2/1999 | Peel, III | |
| 5,873,834 A | 2/1999 | Yanagi et al. | |
| 5,876,353 A | 3/1999 | Riff | |
| 5,895,359 A | 4/1999 | Peel, III | |
| 5,899,855 A | 5/1999 | Brown | |
| 5,913,827 A | 6/1999 | Gorman | |
| 5,919,141 A | 7/1999 | Money et al. | |
| 5,941,836 A | 8/1999 | Friedman | |
| 5,964,701 A | 10/1999 | Asada et al. | |
| 5,964,720 A | 10/1999 | Pelz | |
| 5,971,930 A | 10/1999 | Elghazzawi | |
| 6,002,952 A | 12/1999 | Diab et al. | |
| 6,011,985 A | 1/2000 | Athan et al. | |
| 6,018,673 A | 1/2000 | Chin et al. | |
| 6,036,642 A | 3/2000 | Diab et al. | |
| 6,041,783 A | 3/2000 | Gruenke | |
| 6,057,758 A | 5/2000 | Dempsey et al. | |
| 6,067,462 A | 5/2000 | Diab et al. | |
| 6,071,244 A * | 6/2000 | Band | A61B 5/029 600/526 |
| 6,081,735 A | 6/2000 | Diab et al. | |
| 6,081,742 A | 6/2000 | Amano et al. | |
| 6,094,592 A | 7/2000 | Yorkey et al. | |
| 6,117,077 A | 9/2000 | Del Mar et al. | |
| 6,129,686 A | 10/2000 | Friedman | |
| 6,157,850 A | 12/2000 | Diab et al. | |
| 6,159,147 A | 12/2000 | Lighter et al. | |
| 6,160,478 A | 12/2000 | Jacobsen et al. | |
| 6,168,569 B1 | 1/2001 | McEwen et al. | |
| 6,176,831 B1 | 1/2001 | Voss et al. | |
| 6,198,394 B1 | 3/2001 | Jacobsen et al. | |
| 6,198,951 B1 | 3/2001 | Kosuda et al. | |
| 6,199,550 B1 | 3/2001 | Wiesmann et al. | |
| 6,206,830 B1 | 3/2001 | Diab et al. | |
| 6,236,872 B1 | 5/2001 | Diab et al. | |
| 6,251,080 B1 | 6/2001 | Henkin et al. | |
| 6,261,247 B1 | 7/2001 | Ishikawa et al. | |
| 6,262,769 B1 | 7/2001 | Anderson et al. | |
| 6,263,222 B1 | 7/2001 | Diab et al. | |
| 6,287,262 B1 | 9/2001 | Amano et al. | |
| 6,322,516 B1 | 11/2001 | Masuda et al. | |
| 6,334,065 B1 | 12/2001 | Al-Ali et al. | |
| 6,371,921 B1 | 4/2002 | Caro et al. | |
| 6,388,240 B2 | 5/2002 | Schulz et al. | |
| RE37,852 E | 9/2002 | Aso et al. | |
| 6,443,890 B1 | 9/2002 | Schulze et al. | |
| 6,480,729 B2 | 11/2002 | Stone | |
| 6,485,431 B1 * | 11/2002 | Campbell | 600/526 |
| 6,491,647 B1 | 12/2002 | Bridger et al. | |
| 6,503,206 B1 | 1/2003 | Li et al. | |
| 6,514,218 B2 | 2/2003 | Yamamoto | |
| 6,516,289 B2 | 2/2003 | David | |
| 6,526,310 B1 | 2/2003 | Carter et al. | |
| 6,527,729 B1 | 3/2003 | Turcott | |
| 6,541,756 B2 | 4/2003 | Schulz et al. | |
| 6,544,173 B2 | 4/2003 | West et al. | |
| 6,544,174 B2 | 4/2003 | West et al. | |
| 6,546,267 B1 | 4/2003 | Sugiura et al. | |
| 6,551,252 B2 | 4/2003 | Sackner et al. | |
| 6,584,336 B1 | 6/2003 | Ali et al. | |
| 6,589,170 B1 | 7/2003 | Flach et al. | |
| 6,595,929 B2 | 7/2003 | Stivoric et al. | |
| 6,605,038 B1 | 8/2003 | Teller et al. | |
| 6,606,993 B1 | 8/2003 | Wiesmann et al. | |
| 6,616,606 B1 | 9/2003 | Petersen et al. | |
| 6,645,154 B2 | 11/2003 | Oka | |
| 6,650,917 B2 | 11/2003 | Diab et al. | |
| 6,684,090 B2 | 1/2004 | Ali et al. | |
| 6,694,177 B2 | 2/2004 | Eggers et al. | |
| 6,699,194 B1 | 3/2004 | Diab et al. | |
| 6,732,064 B1 | 5/2004 | Kadtke et al. | |
| 6,745,060 B2 | 6/2004 | Diab et al. | |
| 6,770,028 B1 | 8/2004 | Ali et al. | |
| 6,790,178 B1 | 9/2004 | Mault et al. | |

(56) References Cited

U.S. PATENT DOCUMENTS

| | | |
|---|---|---|
| 6,811,538 B2 | 11/2004 | Westbrook et al. |
| 6,845,256 B2 | 1/2005 | Chin et al. |
| 6,850,787 B2 | 2/2005 | Weber et al. |
| 6,879,850 B2 | 4/2005 | Kimball |
| 6,893,396 B2 | 5/2005 | Schulze et al. |
| 6,912,414 B2 | 6/2005 | Tong |
| 6,934,571 B2 | 8/2005 | Wiesmann et al. |
| 6,947,781 B2 | 9/2005 | Asada et al. |
| 6,976,958 B2 | 12/2005 | Quy |
| 6,985,078 B2 | 1/2006 | Suzuki et al. |
| 6,997,882 B1 | 2/2006 | Parker et al. |
| 7,020,508 B2 | 3/2006 | Stivoric et al. |
| 7,020,578 B2 | 3/2006 | Sorensen et al. |
| 7,029,447 B2 | 4/2006 | Rantala |
| 7,041,060 B2 | 5/2006 | Flaherty et al. |
| 7,048,687 B1 | 5/2006 | Reuss et al. |
| 7,115,824 B2 | 10/2006 | Lo |
| 7,156,809 B2 | 1/2007 | Quy |
| 7,184,809 B1 | 2/2007 | Sterling et al. |
| 7,186,966 B2 | 3/2007 | Al-Ali |
| 7,194,293 B2 | 3/2007 | Baker, Jr. |
| 7,215,984 B2 | 5/2007 | Diab et al. |
| 7,215,987 B1 | 5/2007 | Sterling et al. |
| 7,225,007 B2 | 5/2007 | Al-Ali et al. |
| 7,237,446 B2 | 7/2007 | Chan et al. |
| 7,241,265 B2 | 7/2007 | Cummings et al. |
| 7,257,438 B2 | 8/2007 | Kinast |
| 7,296,312 B2 | 11/2007 | Menkedick et al. |
| 7,299,159 B2 | 11/2007 | Nanikashvili |
| 7,301,451 B2 | 11/2007 | Hastings |
| 7,314,451 B2 | 1/2008 | Halperin et al. |
| 7,351,206 B2 | 4/2008 | Suzuki et al. |
| 7,355,512 B1 | 4/2008 | Al-Ali |
| 7,373,191 B2 | 5/2008 | Delonzer et al. |
| 7,373,912 B2 | 5/2008 | Self et al. |
| 7,377,794 B2 | 5/2008 | Al-Ali et al. |
| 7,382,247 B2 | 6/2008 | Welch et al. |
| 7,383,069 B2 | 6/2008 | Ruchti et al. |
| 7,383,070 B2 | 6/2008 | Diab et al. |
| 7,384,398 B2 | 6/2008 | Gagnadre et al. |
| 7,400,919 B2 | 7/2008 | Petersen et al. |
| 7,420,472 B2 | 9/2008 | Tran |
| 7,427,926 B2 | 9/2008 | Sinclair et al. |
| 7,455,643 B1 | 11/2008 | Li et al. |
| 7,468,036 B1 | 12/2008 | Rulkov et al. |
| 7,477,143 B2 | 1/2009 | Albert |
| 7,479,890 B2 | 1/2009 | Lehrman et al. |
| 7,485,095 B2 | 2/2009 | Shusterman |
| 7,502,643 B2 | 3/2009 | Farringdon et al. |
| 7,508,307 B2 | 3/2009 | Albert |
| 7,509,131 B2 | 3/2009 | Krumm et al. |
| 7,509,154 B2 | 3/2009 | Diab et al. |
| 7,522,035 B2 | 4/2009 | Albert |
| 7,530,949 B2 | 5/2009 | Al-Ali et al. |
| 7,539,532 B2 | 5/2009 | Tran |
| 7,541,939 B2 | 6/2009 | Zadesky et al. |
| 7,542,878 B2 | 6/2009 | Nanikashvili |
| 7,586,418 B2 | 9/2009 | Cuddihy et al. |
| 7,598,878 B2 | 10/2009 | Goldreich |
| 7,602,301 B1 | 10/2009 | Stirling et al. |
| 7,616,110 B2 | 11/2009 | Crump et al. |
| 7,625,344 B1 | 12/2009 | Brady et al. |
| 7,628,071 B2 | 12/2009 | Sasaki et al. |
| 7,628,730 B1 | 12/2009 | Watterson et al. |
| 7,641,614 B2 | 1/2010 | Asada et al. |
| 7,648,463 B1 | 1/2010 | Elhag et al. |
| 7,656,287 B2 | 2/2010 | Albert et al. |
| 7,668,588 B2 | 2/2010 | Kovacs |
| 7,670,295 B2 | 3/2010 | Sackner et al. |
| 7,674,230 B2 | 3/2010 | Reisfeld |
| 7,674,231 B2 | 3/2010 | McCombie et al. |
| 7,678,061 B2 | 3/2010 | Lee et al. |
| 7,684,954 B2 | 3/2010 | Shahabdeen et al. |
| 7,689,437 B1 | 3/2010 | Teller et al. |
| 7,698,101 B2 | 4/2010 | Alten et al. |
| 7,698,830 B2 | 4/2010 | Townsend et al. |
| 7,698,941 B2 | 4/2010 | Sasaki et al. |
| 7,715,984 B2 | 5/2010 | Ramakrishnan et al. |
| 7,725,147 B2 | 5/2010 | Li et al. |
| 7,782,189 B2 | 8/2010 | Spoonhower et al. |
| 7,827,011 B2 | 11/2010 | Devaul et al. |
| 7,925,022 B2 | 4/2011 | Jung et al. |
| 7,976,480 B2 | 7/2011 | Grajales et al. |
| 7,983,933 B2 | 7/2011 | Karkanias et al. |
| 8,047,998 B2 | 11/2011 | Kolluri et al. |
| 8,082,160 B2 | 12/2011 | Collins, Jr. et al. |
| 8,137,270 B2 | 3/2012 | Keenan et al. |
| 8,167,800 B2 | 5/2012 | Ouchi et al. |
| 2001/0004234 A1 | 6/2001 | Petelenz et al. |
| 2001/0007923 A1 | 7/2001 | Yamamoto |
| 2001/0013826 A1 | 8/2001 | Ahmed et al. |
| 2002/0013517 A1 | 1/2002 | West et al. |
| 2002/0032386 A1 | 3/2002 | Sackner et al. |
| 2002/0072859 A1 | 6/2002 | Kajimoto et al. |
| 2002/0138014 A1* | 9/2002 | Baura ................. A61B 5/029 600/526 |
| 2002/0151805 A1 | 10/2002 | Sugo et al. |
| 2002/0156354 A1 | 10/2002 | Larson |
| 2002/0170193 A1 | 11/2002 | Townsend et al. |
| 2002/0183627 A1 | 12/2002 | Nishii et al. |
| 2002/0193671 A1 | 12/2002 | Ciurczak et al. |
| 2002/0193692 A1 | 12/2002 | Inukai et al. |
| 2002/0198679 A1 | 12/2002 | Victor et al. |
| 2003/0004420 A1 | 1/2003 | Narimatsu |
| 2003/0120164 A1* | 6/2003 | Nielsen ............. A61B 5/02055 600/513 |
| 2003/0130590 A1 | 7/2003 | Bui et al. |
| 2003/0135099 A1 | 7/2003 | Al-Ali |
| 2003/0153836 A1 | 8/2003 | Gagnadre et al. |
| 2003/0158699 A1 | 8/2003 | Townsend et al. |
| 2003/0167012 A1* | 9/2003 | Friedman et al. ............ 600/506 |
| 2003/0171662 A1 | 9/2003 | O'Connor et al. |
| 2003/0181815 A1 | 9/2003 | Ebner et al. |
| 2003/0208335 A1 | 11/2003 | Unuma et al. |
| 2004/0019288 A1 | 1/2004 | Kinast |
| 2004/0030261 A1 | 2/2004 | Rantala |
| 2004/0034293 A1 | 2/2004 | Kimball |
| 2004/0034294 A1 | 2/2004 | Kimball et al. |
| 2004/0054821 A1 | 3/2004 | Warren et al. |
| 2004/0073128 A1 | 4/2004 | Hatlestad et al. |
| 2004/0077934 A1 | 4/2004 | Massad |
| 2004/0122315 A1 | 6/2004 | Krill |
| 2004/0133079 A1 | 7/2004 | Mazar et al. |
| 2004/0162466 A1 | 8/2004 | Quy |
| 2004/0162493 A1 | 8/2004 | Mills |
| 2004/0225207 A1 | 11/2004 | Bae et al. |
| 2004/0267099 A1 | 12/2004 | McMahon et al. |
| 2005/0027205 A1 | 2/2005 | Tarassenko et al. |
| 2005/0043598 A1 | 2/2005 | Goode, Jr. et al. |
| 2005/0059870 A1 | 3/2005 | Aceti |
| 2005/0070773 A1 | 3/2005 | Chin et al. |
| 2005/0113107 A1 | 5/2005 | Meunier |
| 2005/0113703 A1 | 5/2005 | Farringdon et al. |
| 2005/0119586 A1 | 6/2005 | Coyle et al. |
| 2005/0119833 A1 | 6/2005 | Nanikashvili |
| 2005/0124866 A1 | 6/2005 | Elaz et al. |
| 2005/0124903 A1 | 6/2005 | Roteliuk et al. |
| 2005/0149350 A1 | 7/2005 | Kerr et al. |
| 2005/0171444 A1* | 8/2005 | Ono et al. .................... 600/490 |
| 2005/0187796 A1 | 8/2005 | Rosenfeld et al. |
| 2005/0206518 A1 | 9/2005 | Welch et al. |
| 2005/0209511 A1 | 9/2005 | Heruth et al. |
| 2005/0228296 A1 | 10/2005 | Banet |
| 2005/0228298 A1 | 10/2005 | Banet et al. |
| 2005/0228301 A1 | 10/2005 | Banet et al. |
| 2005/0234317 A1 | 10/2005 | Kiani |
| 2005/0240087 A1 | 10/2005 | Keenan et al. |
| 2005/0261565 A1 | 11/2005 | Lane et al. |
| 2005/0261593 A1 | 11/2005 | Zhang et al. |
| 2005/0265267 A1 | 12/2005 | Hwang |
| 2005/0283088 A1* | 12/2005 | Bernstein ..................... 600/506 |
| 2006/0036141 A1 | 2/2006 | Kamath et al. |
| 2006/0047215 A1 | 3/2006 | Newman et al. |
| 2006/0074321 A1 | 4/2006 | Kouchi et al. |

(56) References Cited

U.S. PATENT DOCUMENTS

| | | |
|---|---|---|
| 2006/0074322 A1 | 4/2006 | Nitzan |
| 2006/0128263 A1 | 6/2006 | Baird |
| 2006/0142648 A1 | 6/2006 | Banet et al. |
| 2006/0155589 A1 | 7/2006 | Lane et al. |
| 2006/0178591 A1 | 8/2006 | Hempfling |
| 2006/0200029 A1 | 9/2006 | Evans et al. |
| 2006/0252999 A1 | 11/2006 | Devaul et al. |
| 2006/0265246 A1 | 11/2006 | Hoag |
| 2006/0270949 A1 | 11/2006 | Mathie et al. |
| 2006/0271404 A1 | 11/2006 | Brown |
| 2006/0281979 A1 | 12/2006 | Kim et al. |
| 2007/0010719 A1 | 1/2007 | Huster et al. |
| 2007/0055163 A1 | 3/2007 | Asada et al. |
| 2007/0066910 A1 | 3/2007 | Inukai et al. |
| 2007/0071643 A1 | 3/2007 | Hall et al. |
| 2007/0094045 A1 | 4/2007 | Cobbs et al. |
| 2007/0118056 A1 | 5/2007 | Wang et al. |
| 2007/0129769 A1 | 6/2007 | Bourget et al. |
| 2007/0142715 A1 | 6/2007 | Banet et al. |
| 2007/0156456 A1 | 7/2007 | McGillin et al. |
| 2007/0161912 A1 | 7/2007 | Zhang et al. |
| 2007/0185393 A1 | 8/2007 | Zhou et al. |
| 2007/0188323 A1 | 8/2007 | Sinclair et al. |
| 2007/0193834 A1 | 8/2007 | Pai et al. |
| 2007/0208233 A1 | 9/2007 | Kovacs |
| 2007/0232867 A1 | 10/2007 | Hansmann |
| 2007/0237719 A1 | 10/2007 | Jones et al. |
| 2007/0244376 A1 | 10/2007 | Wang |
| 2007/0250261 A1 | 10/2007 | Soehren |
| 2007/0252853 A1 | 11/2007 | Park et al. |
| 2007/0255116 A1 | 11/2007 | Mehta et al. |
| 2007/0260487 A1 | 11/2007 | Bartfeld et al. |
| 2007/0265533 A1 | 11/2007 | Tran |
| 2007/0265880 A1 | 11/2007 | Bartfeld et al. |
| 2007/0270671 A1 | 11/2007 | Gal |
| 2007/0276261 A1 | 11/2007 | Banet et al. |
| 2007/0282208 A1 | 12/2007 | Jacobs et al. |
| 2007/0287386 A1 | 12/2007 | Agrawal et al. |
| 2007/0293770 A1 | 12/2007 | Bour et al. |
| 2007/0293781 A1 | 12/2007 | Sims et al. |
| 2008/0004500 A1 | 1/2008 | Cazares et al. |
| 2008/0004507 A1 | 1/2008 | Williams, Jr. et al. |
| 2008/0004904 A1 | 1/2008 | Tran |
| 2008/0027341 A1 | 1/2008 | Sackner et al. |
| 2008/0033255 A1 | 2/2008 | Essenpreis et al. |
| 2008/0039731 A1 | 2/2008 | McCombie et al. |
| 2008/0077027 A1 | 3/2008 | Allgeyer |
| 2008/0082001 A1 | 4/2008 | Hatlestad et al. |
| 2008/0101160 A1 | 5/2008 | Besson |
| 2008/0103405 A1 | 5/2008 | Banet et al. |
| 2008/0114220 A1 | 5/2008 | Banet et al. |
| 2008/0132106 A1 | 6/2008 | Burnes et al. |
| 2008/0139955 A1 | 6/2008 | Hansmann et al. |
| 2008/0146887 A1 | 6/2008 | Rao et al. |
| 2008/0146892 A1 | 6/2008 | Leboeuf et al. |
| 2008/0161707 A1 | 7/2008 | Farringdon et al. |
| 2008/0162496 A1 | 7/2008 | Postrel |
| 2008/0167535 A1 | 7/2008 | Stivoric et al. |
| 2008/0171927 A1 | 7/2008 | Yang et al. |
| 2008/0194918 A1 | 8/2008 | Kulik et al. |
| 2008/0195735 A1 | 8/2008 | Hodges et al. |
| 2008/0204254 A1 | 8/2008 | Kazuno |
| 2008/0208013 A1 | 8/2008 | Zhang et al. |
| 2008/0208273 A1 | 8/2008 | Owen et al. |
| 2008/0214963 A1 | 9/2008 | Guillemaud et al. |
| 2008/0221399 A1 | 9/2008 | Zhou et al. |
| 2008/0221404 A1 | 9/2008 | Tso |
| 2008/0262362 A1 | 10/2008 | Kolluri et al. |
| 2008/0275349 A1 | 11/2008 | Halperin et al. |
| 2008/0281168 A1 | 11/2008 | Gibson et al. |
| 2008/0281310 A1 | 11/2008 | Dunning et al. |
| 2008/0287751 A1 | 11/2008 | Stivoric et al. |
| 2008/0294019 A1 | 11/2008 | Tran |
| 2008/0319282 A1 | 12/2008 | Tran |
| 2008/0319327 A1 | 12/2008 | Banet et al. |
| 2009/0018408 A1 | 1/2009 | Ouchi et al. |
| 2009/0018409 A1 | 1/2009 | Banet et al. |
| 2009/0018453 A1 | 1/2009 | Banet et al. |
| 2009/0040041 A1 | 2/2009 | Janetis et al. |
| 2009/0054752 A1 | 2/2009 | Jonnalagadda et al. |
| 2009/0069642 A1 | 3/2009 | Gao et al. |
| 2009/0076363 A1 | 3/2009 | Bly et al. |
| 2009/0076397 A1 | 3/2009 | Libbus et al. |
| 2009/0076398 A1 | 3/2009 | Li et al. |
| 2009/0076405 A1 | 3/2009 | Amurthur et al. |
| 2009/0082681 A1 | 3/2009 | Yokoyama et al. |
| 2009/0099424 A1* | 4/2009 | O'Brien et al. ............... 600/301 |
| 2009/0112072 A1 | 4/2009 | Banet et al. |
| 2009/0112281 A1 | 4/2009 | Miyazawa et al. |
| 2009/0112630 A1 | 4/2009 | Collins, Jr. et al. |
| 2009/0118590 A1 | 5/2009 | Teller et al. |
| 2009/0118626 A1 | 5/2009 | Moon et al. |
| 2009/0131759 A1 | 5/2009 | Sims et al. |
| 2009/0187085 A1 | 7/2009 | Pav |
| 2009/0192366 A1 | 7/2009 | Mensinger et al. |
| 2009/0198139 A1 | 8/2009 | Lewicke et al. |
| 2009/0221937 A1 | 9/2009 | Smith et al. |
| 2009/0222119 A1 | 9/2009 | Plahey et al. |
| 2009/0227877 A1 | 9/2009 | Tran |
| 2009/0233770 A1 | 9/2009 | Vincent et al. |
| 2009/0259113 A1 | 10/2009 | Liu et al. |
| 2009/0262074 A1 | 10/2009 | Nasiri et al. |
| 2009/0264712 A1 | 10/2009 | Baldus et al. |
| 2009/0287067 A1 | 11/2009 | Dorogusker et al. |
| 2009/0295541 A1 | 12/2009 | Roof |
| 2009/0306485 A1 | 12/2009 | Bell |
| 2009/0306487 A1 | 12/2009 | Crowe et al. |
| 2009/0306524 A1 | 12/2009 | Muhlsteff et al. |
| 2009/0312973 A1 | 12/2009 | Hatlestad et al. |
| 2009/0318779 A1 | 12/2009 | Tran |
| 2009/0322513 A1 | 12/2009 | Hwang et al. |
| 2009/0326349 A1 | 12/2009 | McGonigle et al. |
| 2010/0010380 A1 | 1/2010 | Panken et al. |
| 2010/0030034 A1 | 2/2010 | Schulhauser et al. |
| 2010/0030085 A1 | 2/2010 | Rojas Ojeda et al. |
| 2010/0056881 A1 | 3/2010 | Libbus et al. |
| 2010/0056886 A1 | 3/2010 | Hurtubise et al. |
| 2010/0113948 A1 | 5/2010 | Yang et al. |
| 2010/0125188 A1 | 5/2010 | Schilling et al. |
| 2010/0130811 A1 | 5/2010 | Leuthardt et al. |
| 2010/0160793 A1 | 6/2010 | Lee et al. |
| 2010/0160794 A1 | 6/2010 | Banet et al. |
| 2010/0160795 A1 | 6/2010 | Banet et al. |
| 2010/0160796 A1 | 6/2010 | Banet et al. |
| 2010/0160797 A1 | 6/2010 | Banet et al. |
| 2010/0160798 A1 | 6/2010 | Banet et al. |
| 2010/0168589 A1 | 7/2010 | Banet et al. |
| 2010/0210930 A1 | 8/2010 | Saylor |
| 2010/0217099 A1 | 8/2010 | Leboeuf et al. |
| 2010/0222649 A1 | 9/2010 | Schoenberg |
| 2010/0234693 A1 | 9/2010 | Srinivasan et al. |
| 2010/0234786 A1 | 9/2010 | Fulkerson et al. |
| 2010/0241011 A1 | 9/2010 | McCombie et al. |
| 2010/0268518 A1* | 10/2010 | Sugo ................ 703/2 |
| 2010/0280440 A1 | 11/2010 | Skelton et al. |
| 2010/0298650 A1 | 11/2010 | Moon et al. |
| 2010/0298651 A1 | 11/2010 | Moon et al. |
| 2010/0298652 A1 | 11/2010 | McCombie et al. |
| 2010/0298653 A1 | 11/2010 | McCombie et al. |
| 2010/0298654 A1 | 11/2010 | McCombie et al. |
| 2010/0298655 A1 | 11/2010 | McCombie et al. |
| 2010/0298656 A1 | 11/2010 | McCombie et al. |
| 2010/0298657 A1 | 11/2010 | McCombie et al. |
| 2010/0298658 A1 | 11/2010 | McCombie et al. |
| 2010/0298659 A1 | 11/2010 | McCombie et al. |
| 2010/0298660 A1 | 11/2010 | McCombie et al. |
| 2010/0298661 A1 | 11/2010 | McCombie et al. |
| 2010/0312115 A1 | 12/2010 | Dentinger |
| 2010/0317976 A1* | 12/2010 | Chelma ............. A61B 5/02 600/485 |
| 2010/0324384 A1 | 12/2010 | Moon et al. |
| 2010/0324385 A1 | 12/2010 | Moon et al. |
| 2010/0324386 A1 | 12/2010 | Moon et al. |
| 2010/0324387 A1 | 12/2010 | Moon et al. |

(56) References Cited

U.S. PATENT DOCUMENTS

| | | |
|---|---|---|
| 2010/0324388 A1 | 12/2010 | Moon et al. |
| 2010/0324389 A1 | 12/2010 | Moon et al. |
| 2010/0331640 A1 | 12/2010 | Medina |
| 2011/0066006 A1 | 3/2011 | Banet et al. |
| 2011/0066007 A1 | 3/2011 | Banet et al. |
| 2011/0066008 A1 | 3/2011 | Banet et al. |
| 2011/0066009 A1 | 3/2011 | Moon et al. |
| 2011/0066010 A1 | 3/2011 | Moon et al. |
| 2011/0066037 A1 | 3/2011 | Banet et al. |
| 2011/0066038 A1 | 3/2011 | Banet et al. |
| 2011/0066039 A1 | 3/2011 | Banet et al. |
| 2011/0066043 A1 | 3/2011 | Banet et al. |
| 2011/0066044 A1 | 3/2011 | Moon et al. |
| 2011/0066045 A1 | 3/2011 | Moon et al. |
| 2011/0066050 A1 | 3/2011 | Moon et al. |
| 2011/0066051 A1 | 3/2011 | Moon et al. |
| 2011/0066062 A1 | 3/2011 | Banet et al. |
| 2011/0070829 A1 | 3/2011 | Griffin et al. |
| 2011/0076942 A1 | 3/2011 | Taveau et al. |
| 2011/0087116 A1* | 4/2011 | Parkin et al. ............ 600/485 |
| 2011/0093281 A1 | 4/2011 | Plummer et al. |
| 2011/0105862 A1 | 5/2011 | Gies et al. |
| 2011/0144456 A1 | 6/2011 | Muhlsteff et al. |
| 2011/0152632 A1 | 6/2011 | Le Neel et al. |
| 2011/0178375 A1 | 7/2011 | Forster |
| 2011/0224498 A1 | 9/2011 | Banet et al. |
| 2011/0224499 A1 | 9/2011 | Banet et al. |
| 2011/0224500 A1 | 9/2011 | Banet et al. |
| 2011/0224506 A1 | 9/2011 | Moon et al. |
| 2011/0224507 A1 | 9/2011 | Banet et al. |
| 2011/0224508 A1 | 9/2011 | Moon |
| 2011/0224556 A1 | 9/2011 | Moon et al. |
| 2011/0224557 A1 | 9/2011 | Banet et al. |
| 2011/0224564 A1 | 9/2011 | Moon et al. |
| 2011/0257489 A1 | 10/2011 | Banet et al. |
| 2011/0257551 A1 | 10/2011 | Banet et al. |
| 2011/0257552 A1 | 10/2011 | Banet et al. |
| 2011/0257554 A1 | 10/2011 | Banet et al. |
| 2011/0257555 A1 | 10/2011 | Banet et al. |
| 2011/0275907 A1 | 11/2011 | Inciardi et al. |
| 2012/0065525 A1 | 3/2012 | Douniama et al. |
| 2012/0123232 A1 | 5/2012 | Najarian et al. |

FOREIGN PATENT DOCUMENTS

| | | |
|---|---|---|
| GB | 2329250 A | 3/1999 |
| WO | 1999032030 A1 | 7/1999 |
| WO | 2006005169 A1 | 1/2006 |
| WO | 2007024777 A2 | 3/2007 |
| WO | 2007143535 A2 | 12/2007 |
| WO | 2008037820 A1 | 4/2008 |
| WO | 2008110788 A1 | 9/2008 |
| WO | 2009009761 A1 | 1/2009 |
| WO | 2010135516 A2 | 11/2010 |
| WO | 2010135518 A1 | 11/2010 |
| WO | 2010148205 A1 | 12/2010 |
| WO | 2011032132 A2 | 3/2011 |
| WO | 2011034881 A1 | 3/2011 |
| WO | 2011082341 A1 | 7/2011 |
| WO | 2011112782 A1 | 9/2011 |
| WO | 2011133582 A1 | 10/2011 |

OTHER PUBLICATIONS

Non-Final Office Action issued by the US Patent and Trademark Office dated Sep. 14, 2012 in U.S. Appl. No. 12/650,374.
Drinnan et al., Relation between heart rate and pulse transit time during paced respiration. Physiol. Meas. Aug. 2001;22(3):425-432.
Flash et al., The Coordination of Arm Movements: An Experimentally Confirmed Mathematical Model. J Neurosci. Jul. 1985;5(7):1688-1703.
Ma and Zhang, A Correlation Study on the Variabilities in Pulse Transit Time, Blood Pressure, and Heart Rate Recorded Simultaneously from Healthy Subjects. Conf Proc IEEE Eng Med Biol Soc. 2005;1:996-999.
Non-Final Office Action issued by the US Patent and Trademark Office dated Sep. 17, 2012 in U.S. Appl. No. 12/469,192.
Gallagher, Comparison of Radial and Femoral Arterial Blood Pressure in Children after Cardiopulmonary Bypass. J Clin Monit. Jul. 1985;1(3):168-171.
Park et al., Direct Blood Pressure Measurements in Brachial and Femoral Arteries in Children. Circulation Feb. 1970; 41(2)231-237.
Talkowski, Quantifying Physical Activity in Community Dwelling Older Adults Using Accelerometry. University of Pittsburgh (Dissertation) 2008:1-91.
Non-Final Office Action issued by the US Patent and Trademark Office dated Sep. 26, 2012 in U.S. Appl. No. 12/560,104.
Packet Definition. The Linux Information Project Jan. 8, 2006 http://www.linfo.org/packet.html.
RS-232. Wikipedia Dec. 5, 2008 http:l/web.archive.org/web/20081205160754/http:/len.wikipedia.org/wiki/RS-232.
Non-Final Office Action issued by the US Patent and Trademark Office dated Oct. 9, 2012 in U.S. Appl. No. 12/762,726.
Final Office Action issued by the US Patent and Trademark Office dated Oct. 22, 2012 in U.S. Appl. No. 12/762,822.
Final Office Action issued by the US Patent and Trademark Office dated Oct. 25, 2012 in U.S. Appl. No. 12/599,426.
Alves et al., CAN Protocol: A Laboratory Prototype for Fieldbus Applications. XIX IMEKO World Congress Fundamental and Applied Metrology Sep. 6-11, 2009, Lisbon, Portugal. 4 pages :454-457 ISBN 978-963-88410-0-1.
Benefits of Digital Sensors. Gems Sensors. Feb. 14, 2008. http://web.archive.org/web/20080214122230/http://www.sensorland.com/HowPage054.html.
Final Office Action issued by the US Patent and Trademark Office dated Oct. 25, 2012 in U.S. Appl. No. 12/762,790.
Non-Final Office Action issued by the US Patent and Trademark Office dated Oct. 30, 2012 in U.S. Appl. No. 12/559,386.
Non-Final Office Action issued by the US Patent and Trademark Office dated Nov. 6, 2012 in U.S. Appl. No. 12/559,379.
Non-Final Office Action issued by the US Patent and Trademark Office dated Nov. 6, 2012 in U.S. Appl. No. 12/650,370.
Poon and Zhang, Cuff-Less and Noninvasive Measurements of Arterial Blood Pressure by Pulse Transit Time. Conf Proc IEEE Eng Med Biol Soc. 2005;6:5877-5880.
Non-Final Office Action issued by the US Patent and Trademark Office dated Nov. 7, 2012 in U.S. Appl. No. 12/559,392.
Final Office Action issued by the United States Patent and Trademark Office in U.S. Appl. No. 12/469,236 dated Jul. 8, 2013.
Non-Final Office Action issued by the United States Patent and Trademark Office in U.S. Appl. No. 12/560,111 dated Jul. 8, 2013.
Scanaill et al., A Review of Approaches to Mobility Telemonitoring of the Elderly in Their Living Environment. Annals of Biomed Engineer. Apr. 2006;34(4):547-563.
Notice of Allowance issued by the United States Patent and Trademark Office in U.S. Appl. No. 12/762,733 dated Jul. 24, 2013.
Final Office Action issued by the United States Patent and Trademark Office in U.S. Appl. No. 12/762,944 dated Aug. 2, 2013.
Response to Office Action issued by the United States Patent and Trademark Office in U.S. Appl. No. 12/559,039 dated Aug. 9, 2013.
Sifil et al., Evaluation of the Harmonized Alert Sensing Technology Device for Hemodynamic Monitoring in Chronic Hemodialysis Patients. ASAIO J. Nov.-Dec. 2003;49(6):667-672.
Weinhold et al., Buprenorphine alone and in combination with naloxone in non-dependent humans. Drug Alcohol Depend. Aug. 1992;30(3):263-274.
Final Office Action issued by the United States Patent and Trademark Office in U.S. Appl. No. 12/762,726 dated Aug. 15, 2013.
Extended European Search Report and Written Opinion issued in application No. EP 10817733 dated Aug. 29, 2013.
Extended European Search Report and Written Opinion issued in application No. EP 08770884 dated Sep. 17, 2013.
Non-Final Office Action issued by the US Patent and Trademark Office dated Jun. 11, 2012 in U.S. Appl. No. 12/469,222.
Non-Final Office Action issued by the US Patent and Trademark Office dated Jun. 8, 2012 in U.S. Appl. No. 12/650,383.

(56) References Cited

OTHER PUBLICATIONS

Non-Final Office Action issued by the US Patent and Trademark Office dated Jun. 8, 2012 in U.S. Appl. No. 12/650,392.
Non-Final Office Action issued by the US Patent and Trademark Office dated Jun. 20, 2012 in U.S. Appl. No. 12/762,751.
International Search Report and Written Opinion dated Jun. 29, 2012 issued in PCT/US2012/025640.
Non-Final Office Action issued by the US Patent and Trademark Office dated Jul. 5, 2012 in U.S. Appl. No. 12/560,138.
"Signal Strength." Oct. 6, 2008. http://web.archive.org/web/20081006200523/http://!en.wikipedia.org/wiki/Signal_strength.
Non-Final Office Action issued by the US Patent and Trademark Office dated May 24, 2012 in U.S. Appl. No. 12/560,111.
Restriction Requirement issued by the US Patent and Trademark Office dated Apr. 24, 2012 in U.S. Appl. No. 12/469,107.
Response to Restriction Requirement submitted Jun. 14, 2012 in U.S. Appl. No. 12/469,107.
Non-Final Office Action issued by the US Patent and Trademark Office dated Aug. 30, 2012 in U.S. Appl. No. 12/469,202.
Non-Final Office Action issued by the US Patent and Trademark Office dated Sep. 17, 2012 in U.S. Appl. No. 12/650,354.
Non-Final Office Action issued by the US Patent and Trademark Office dated Sep. 21, 2012 in U.S. Appl. No. 12/469,115.
Response to Non-Final Office Action issued in U.S. Appl. No. 12/469,236 dated Sep. 27, 2012.
Response to Non-Final Office Action issued in U.S. Appl. No. 12/487,283 dated Sep. 27, 2012.
Non-Final Office Action issued by the US Patent and Trademark Office dated Sep. 28, 2012 in U.S. Appl. No. 12/560,087.
Response to Non-Final Office Action issued in U.S. Appl. No. 12/762,836 dated Oct. 9, 2012.
Response to Non-Final Office Action issued in U.S. Appl. No. 12/559,429 dated Oct. 12, 2012.
Response to Non-Final Office Action issued in U.S. Appl. No. 12/559,430 dated Oct. 12, 2012.
Response to Non-Final Office Action issued in U.S. Appl. No. 12/559,435 dated Oct. 23, 2012.
Final Office Action issued by the US Patent and Trademark Office dated Oct. 24, 2012 in U.S. Appl. No. 12/599,429.
Final Office Action issued by the US Patent and Trademark Office dated Oct. 24, 2012 in U.S. Appl. No. 12/599,430.
Non-Final Office Action issued by the US Patent and Trademark Office dated Oct. 23, 2012 in U.S. Appl. No. 12/762,944.
Response to Non-Final Office Action issued in U.S. Appl. No. 12/762,733 dated Oct. 25, 2012.
Final Office Action issued by the US Patent and Trademark Office dated Oct. 26, 2012 in U.S. Appl. No. 12/762,836.
Non-Final Office Action issued by the US Patent and Trademark Office dated Oct. 24, 2012 in U.S. Appl. No. 12/559,403.
Non Final Office Action issued by the United States Patent and Trademark Office in U.S. Appl. No. 12/559,413 dated Nov. 9, 2012.
Response to Office Action issued in U.S. Appl. No. 12/762,846 dated Nov. 13, 2012.
Response to Office Action issued in U.S. Appl. No. 12/762,874 dated Nov. 13, 2012.
Response to Office Action issued in U.S. Appl. No. 12/560,111 dated Nov. 26, 2012.
Response to Office Action issued in U.S. Appl. No. 11/930,881 dated Nov. 26, 2012.
Final Rejection issued by the United States Patent and Trademark Office in U.S. Appl. No. 12/559,419 dated Nov. 16, 2012.
Non Final Office Action issued by the United States Patent and Trademark Office in U.S. Appl. No. 12/559,408 dated Nov. 23, 2012.
Response to Office Action issued in U.S. Appl. No. 12/138,199 dated Nov. 29, 2012.
Response to Office Action issued in U.S. Appl. No. 12/650,383 dated Dec. 7, 2012.
Response to Office Action issued in U.S. Appl. No. 12/650,392 dated Dec. 7, 2012.
Final Rejection issued by the United States Patent and Trademark Office in U.S. Appl. No. 12/559,435 dated Dec. 12, 2012.
Final Rejection issued by the United States Patent and Trademark Office in U.S. Appl. No. 12/560,111 dated Dec. 12, 2012.
Clifford et al., Measuring Tilt with Low-g Accelerometers. Freescale Semiconductor, Inc., 2005:8 pages.
McKneely et al., Plug-and-Play and Network-Capable Medical Instrumentation and Database with a Complete Healthcare Technology Suite: MediCAN. Joint Workshop on High Confidence Medical Devices, Software, and Systems and Medical Device Plug-and-Play Interoperability. 2007:122-129.
Montgomery et al., Lifeguard—A Personal Physiological Monitor for Extreme Environments. Conf Proc IEEE Eng Med Biol Soc. 2004;3:2192-2195.
Thongpithoonrat et al., Networking and Plug-and-Play of Bedside Medical Instruments. Conf Proc IEEE Eng Med Biol Soc. 2008;2008:1514-1517.
Yang et al., Research on Multi-Parameter Physiological Monitor Based on Can Bus. IFMBE Proceed. 2008;19:417-419.
Zeltwanger, Controller Area Network and CANopen in Medical Equipment. Bus Briefing: Med Dev Manuf Technol. 2002:34-37.
Zitzmann and Schumann, Interoperable Medical Devices Due to Standardized CANopen Interfaces. Joint Workshop on High Confidence Medical Devices, Software, and Systems and Medical Device Plug-and-Play Interoperability. 2007:97-103.
Non Final Office Action issued by the United States Patent and Trademark Office in U.S. Appl. No. 13/432,976 dated Dec. 14, 2012.
Final Rejection issued by the United States Patent and Trademark Office in U.S. Appl. No. 12/762,733 dated Dec. 20, 2012.
Final Rejection issued by the United States Patent and Trademark Office in U.S. Appl. No. 12/762,846 dated Dec. 20, 2012.
Final Rejection issued by the United States Patent and Trademark Office in U.S. Appl. No. 12/650,392 dated Jan. 3, 2013.
Final Rejection issued by the United States Patent and Trademark Office in U.S. Appl. No. 12/487,283 dated Jan. 3, 2013.
Non Final Office Action issued by the United States Patent and Trademark Office in U.S. Appl. No. 13/292,923 dated Jan. 14, 2013.
Notice of Allowance issued by the United States Patent and Trademark Office in U.S. Appl. No. 11/470,708 dated Jan. 18, 2013.
International Search Report and Written Opinion issued in PCT/US2012/064302 dated Jan. 15, 2013.
Allen et al., Classification of a known sequence of motions and postures from accelerometry data using adapted Gaussian mixture models. Physiol. Meas. 2006;27:935-951.
Asada et al., Active Noise Cancellation Using MEMS Accelerometers for Motion-Tolerant Wearable Bio-Sensors. Proceedings of the 26th Annual International Conference of the IEEE EMBS. San Francisco, CA, USA. Sep. 1-5, 2004:2157-2160.
Bowers et al., Respiratory Rate Derived from Principal Component Analysis of Single Lead Electrocardiogram. Computers in Cardiology Conference Proceedings Sep. 2008;35:437-440.
Bussmann et al., Measuring daily behavior using ambulatory accelerometry: The Activity Monitor. Behav Res Methods Instrum Comput. Aug. 2001;33(3):349-356.
Cretikos et al., The Objective Medical Emergency Team Activation Criteria: a case—control study. Resuscitation Apr. 2007;73(1):62-72.
Espina et al., Wireless Body Sensor Network for Continuous Cuff-less Blood Pressure Monitoring. Proceedings of the 3rd IEEE-EMBS. International Summer School and Symposium on Medical Devices and Biosensors. MIT, Boston, USA, Sep. 4-6, 2006:11-15.
Fieselmann et al., Respiratory rate predicts cardiopulmonary arrest for internal medicine patients. J Gen Intern Med Jul. 1993;8(7):354-360.
Goldhill et al., A physiologically-based early warning score for ward patients: the association between score and outcome. Anaesthesia Jun. 2005;60(6):547-553.
Hung et al., Estimation of Respiratory Waveform Using an Accelerometer. 5th IEEE International Symposium on Biomedical Imaging: From Nano to Macro, May 14-17, 2008:1493-1496.
Jin, A Respiration Monitoring System Based on a Tri-Axial Accelerometer and an Air-Coupled Microphone. Technische Universiteit

(56) References Cited

OTHER PUBLICATIONS

Eindhoven, University of Technology. Master's Graduation Paper, Electrical Engineering Aug. 25, 2009.
Karantonis et al., Implementation of a Real-Time Human Movement Classifier Using a Triaxial Accelerometer for Ambulatory Monitoring. IEEE Transactions on Information Technology in Biomedicine. Jan. 2006;10(1):156-167.
Khambete et al., Movement artefact rejection in impedance pneumography using six strategically placed electrodes. Physiol. Meas. 2000;21:79-88.
Khan et al., Accelerometer Signal-based Human Activity Recognition Using Augmented Autoregressive Model Coefficients and Artificial w Neural Nets. 30th Annual International Conference of the IEEE Engineering in Medicine and Biology Society. Aug. 20-24, 2008:5172-5175.
Mason, Signal Processing Methods for Non-Invasive Respiration Monitoring. Department of Engineering Science, University of Oxford 2002.
Mathie et al., Classification of basic daily movements using a triaxial accelerometer. Med Biol Eng Comput. Sep. 2004;42(5):679-687.
Otto et al., System Architecture of a Wireless Body Area Sensor Network for Ubiquitous Health Monitoring. Journal of Mobile Multimedia Jan. 10, 2006;1(4):307-326.
Park et al., An improved algorithm for respiration signal extraction from electrocardiogram measured by conductive textile electrodes using instantaneous frequency estimation. Med Bio Eng Comput 2008;46:147-158.
PDF-Pro for iPhone & iPod touch User Manual. ePapyrus Jul. 2009;1:1-25 http://epapyrus.com/en/files/PDFPro%.
Seo et al., Performance Improvement of Pulse Oximetry-Based Respiration Detection by Selective Mode Bandpass Filtering. Ergonomics and Health Aspects of Work with Computers Lecture Notes in Computer Science, 2007;4566:300-308.
Soh et al., An investigation of respiration while wearing back belts. Applied Ergonomics 1997; 28(3):189-192.
Subbe et al., Effect of introducing the Modified Early Warning score on clinical outcomes, cardiopulmonary arrests and intensive care utilization in acute medical admissions. Anaesthesia Aug. 2003;58(8):797-802.
Vuorela et al., Two portable long-term measurement devices for ECG and bioimpedance. Second International Conference on Pervasive Computing Technologies for Healthcare.. Jan. 30-Feb. 1, 2008: 169-172.
Wolf et al., Development of a Fall Detector and Classifier based on a Triaxial Accelerometer Demo Board. 2007:210-213.
Non-Final Office Action issued by the US Patent and Trademark Office dated Apr. 30, 2012 in U.S. Appl. No. 12/762,790.
Non-Final Office Action issued by the US Patent and Trademark Office dated Mar. 30, 2012 in U.S. Appl. No. 12/469,236.
Non-Final Office Action issued by the US Patent and Trademark Office dated Apr. 3, 2012 in U.S. Appl. No. 12/469,094.
Restriction Requirement issued by the US Patent and Trademark Office dated Feb. 2, 2012 in U.S. Appl. No. 12/469,222.
Non-Final Office Action issued by the US Patent and Trademark Office dated Mar. 27, 2012 in U.S. Appl. No. 12/559,426.
Non-Final Office Action issued by the US Patent and Trademark Office dated Apr. 3, 2012 in U.S. Appl. No. 12/559,039.
Non-Final Office Action issued by the US Patent and Trademark Office dated Dec. 29, 2011 in U.S. Appl. No. 12/559,080.
Response to Non-Final Office Action submitted Mar. 19, 2012 in U.S. Appl. No. 12/559,080.
Notice of Allowance issued by the US Patent and Trademark Office dated Apr. 2, 2012 in U.S. Appl. No. 12/559,080.
Non-Final Office Action issued by the US Patent and Trademark Office dated Dec. 15, 2011 in U.S. Appl. No. 12/560,077.
Non-Final Office Action issued by the US Patent and Trademark Office dated Mar. 8, 2012 in U.S. Appl. No. 12/560,093.
Restriction Requirement issued by the US Patent and Trademark Office dated Dec. 14, 2012 in U.S. Appl. No. 12/560,093.
Response to Restriction Requirement submitted Feb. 15, 2012 in U.S. Appl. No. 12/560,093.
Non-Final Office Action issued by the US Patent and Trademark Office dated Mar. 1, 2012 in U.S. Appl. No. 12/560,104.
Restriction Requirement issued by the US Patent and Trademark Office dated Jan. 19, 2012 in U.S. Appl. No. 12/469,115.
Response to Restriction Requirement submitted Feb. 15, 2012 in U.S. Appl. No. 12/469,115.
Restriction Requirement issued by the US Patent and Trademark Office dated Nov. 14, 2011 in U.S. Appl. No. 12/469,127.
Response to Restriction Requirement submitted Feb. 15, 2012 in U.S. Appl. No. 12/469,127.
Non-Final Office Action issued by the US Patent and Trademark Office dated Mar. 9, 2012 in U.S. Appl. No. 12/469,127.
Non-Final Office Action issued by the US Patent and Trademark Office dated Apr. 3, 2012 in U.S. Appl. No. 12/469,137.
International Preliminary Report on Patentability dated Dec. 1, 2011 issued in PCT/US2010/035554.
International Search Report and Written Opinion dated Sep. 23, 2010 issued in PCT/US2010/035554.
International Preliminary Report on Patentability dated Jan. 5, 2012 issued in PCT/US2010/039000.
International Search Report and Written Opinion dated Sep. 7, 2010 issued in PCT/US2010/039000.
International Search Report and Written Opinion dated Nov. 3, 2010 issued in PCT/US2010/048729.
International Search Report and Written Opinion dated Nov. 5, 2010 issued in PCT/US2010/048866.
International Search Report and Written Opinion dated Mar. 3, 2011 issued in PCT/US2010/062564.
Non-Final Office Action issued by the US Patent and Trademark Office dated Jul. 18, 2012 in U.S. Appl. No. 12/650,389.
Chan et al., Noninvasive and Cuffless Measurements of Blood Pressure for Telemedicine. Proceedings of the 23rd Annual International Conference of the IEEE Engineering in Medicine and Biology Society 2001:3 pages.
Fung, Advisory System for Administration of Phenylephrine Following Spinal Anesthesia for Cesarean Section. Master's Thesis. University of British Columbia 2002: 119 pages.
Liu et al., The Changes in Pulse Transit Time at Specific Cuff Pressures during Inflation and Deflation. Proceedings of the 28th IEEE EMBS Annual International Conference New York City, USA, Aug. 30-Sep. 3, 2006:6404-6405.
Nitzan et al., Effects of External Pressure on Arteries Distal to the Cuff During Sphygmomanometry. IEEE Transactions on Biomedical Engineering, Jun. 2005;52(6):1120-1127.
USB 2.0 Specification Engineering Change Notice. Oct. 20, 2000.
Yan and Zhang, A Novel Calibration Method for Noninvasive Blood Pressure Measurement Using Pulse Transit Time. Proceedings of the 4th IEEE-EMBS International Summer School and Symposium on Medical Devices and Biosensors St Catharine's College,Cambridge, UK, Aug. 19-22, 2007.
Zislin et al., Ways of Improving the Accuracy of Arterial Pressure Oscillometry. Biomedical Engineering 2005;39 (4):174-178.
International Search Report and Written Opinion dated May 29, 2012 issued in PCT/US2012/025648.
Non-Final Office Action issued by the US Patent and Trademark Office dated Aug. 3, 2012 in U.S. Appl. No. 12/762,925.
Non-Final Office Action issued by the US Patent and Trademark Office dated Aug. 3, 2012 in U.S. Appl. No. 12/762,963.
Non-Final Office Action issued by the US Patent and Trademark Office dated Aug. 20, 2012 in U.S. Appl. No. 12/762,777.
Non-Final Office Action issued by the US Patent and Trademark Office dated Aug. 21, 2012 in U.S. Appl. No. 12/469,107.
Non-Final Office Action issued by the US Patent and Trademark Office dated Aug. 24, 2012 in U.S. Appl. No. 12/762,936.
International Search Report and Written Opinion dated Jul. 22, 2011 issued in PCT/US2011/027843.
International Search Report and Written Opinion dated Jul. 20, 2011 issued in PCT/US2011/033100.
Non-Final Office Action issued by the US Patent and Trademark Office dated May 26, 2011 in U.S. Appl. No. 12/469,151.

(56) References Cited

OTHER PUBLICATIONS

Response to Non-Final Office Action submitted Nov. 25, 2011 in U.S. Appl. No. 12/469,151.
Notice of Allowance issued by the US Patent and Trademark Office dated Feb. 1, 2012 in U.S. Appl. No. 12/469,151.
Non-Final Office Action issued by the US Patent and Trademark Office dated Aug. 4, 2011 in U.S. Appl. No. 12/469,182.
Response to Non-Final Office Action submitted Nov. 25, 2011 in U.S. Appl. No. 12/469,182.
Notice of Allowance issued by the US Patent and Trademark Office dated Dec. 28, 2011 in U.S. Appl. No. 12/469,182.
International Search Report and Written Opinion dated Oct. 15, 2010 issued in PCT/US2010/035550.
Non-Final Office Action issued by the US Patent and Trademark Office dated Apr. 12, 2012 in U.S. Appl. No. 12/559,429.
Non-Final Office Action issued by the US Patent and Trademark Office dated Apr. 12, 2012 in U.S. Appl. No. 12/559,430.
Non-Final Office Action issued by the US Patent and Trademark Office dated Apr. 24, 2012 in U.S. Appl. No. 12/559,435.
Non-Final Office Action issued by the US Patent and Trademark Office dated Apr. 25, 2012 in U.S. Appl. No. 12/762,733.
Non-Final Office Action issued by the US Patent and Trademark Office dated Apr. 27, 2012 in U.S. Appl. No. 12/762,822.
Non-Final Office Action issued by the US Patent and Trademark Office dated Mar. 27, 2012 in U.S. Appl. No. 12/559,422.
Mathie, Monitoring and Interpreting Human Movement Patterns using a Triaxial Accelerometer. Faculty of Engineering. The University of New South Wales. PhD Dissertation. Aug. 2003: part1 pp. 1-256.
Mathie, Monitoring and Interpreting Human Movement Patterns using a Triaxial Accelerometer. Faculty of Engineering. The University of New South Wales. PhD Dissertation. Aug. 2003: part2 pp. 256-512.
International Search Report and Written Opinion dated Apr. 27, 2012 as reported in PCT/US2011/067441.
Non-Final Office Action issued by the US Patent and Trademark Office dated May 7, 2012 in U.S. Appl. No. 12/469,115.
Non-Final Office Action issued by the US Patent and Trademark Office dated May 9, 2012 in U.S. Appl. No. 12/762,836.
Non-Final Office Action issued by the US Patent and Trademark Office dated May 10, 2012 in U.S. Appl. No. 12/559,419.
Jackson, Digital Filter Design and Synthesis Using High-Level Modeling Tools. Virginia Polytechnic Institute and State University Thesis. Dec. 1999.
Kim et al., Two Algorithms for Detecting Respiratory Rate from ECG Signal. IFMBE Proceedings 2007;14(6) JC27:4069-4071.
O'Haver, Peak Finding and Measurement, Version 1.6 Oct. 26, 2006. http://web.archive.org/web/20090205162604/http://terpconnect.umd.edu/-toh/spectrum/PeakFindingandMeasurement.htm.
Reinvuo et al., Measurement of Respiratory Rate with High-Resolution Accelerometer and EMFit Pressure Sensor. Proceedings of the 2006 IEEE Sensors Applications Symposium Feb. 7-9, 2006:192-195.
Non-Final Office Action issued by the US Patent and Trademark Office dated May 11, 2012 in U.S. Appl. No. 12/762,846.
Non-Final Office Action issued by the US Patent and Trademark Office dated May 11, 2012 in U.S. Appl. No. 12/762,874.
Henry et al., "Stroke Volume Obtained From Brachial Artery Using Transbrachial Electrical Bioimpedeance Belocimetry", 34th Annual International Conference of the IEEE EMBS, 2012, 142-145.

* cited by examiner

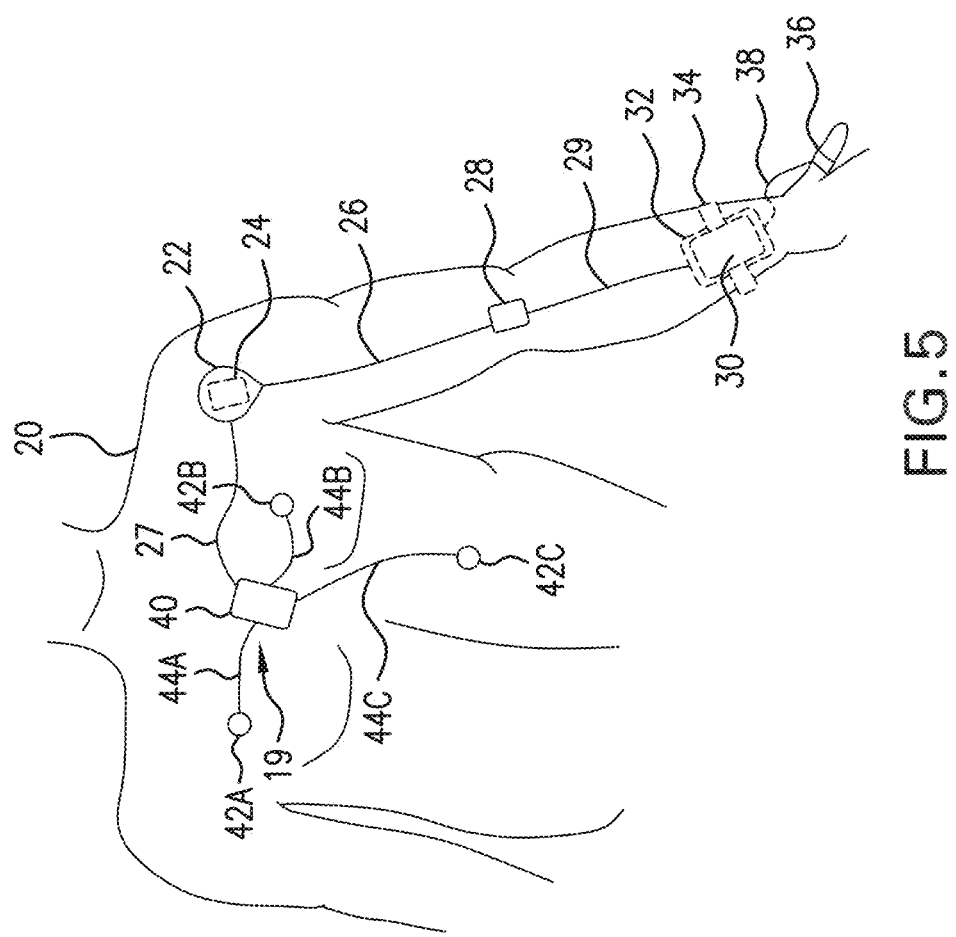

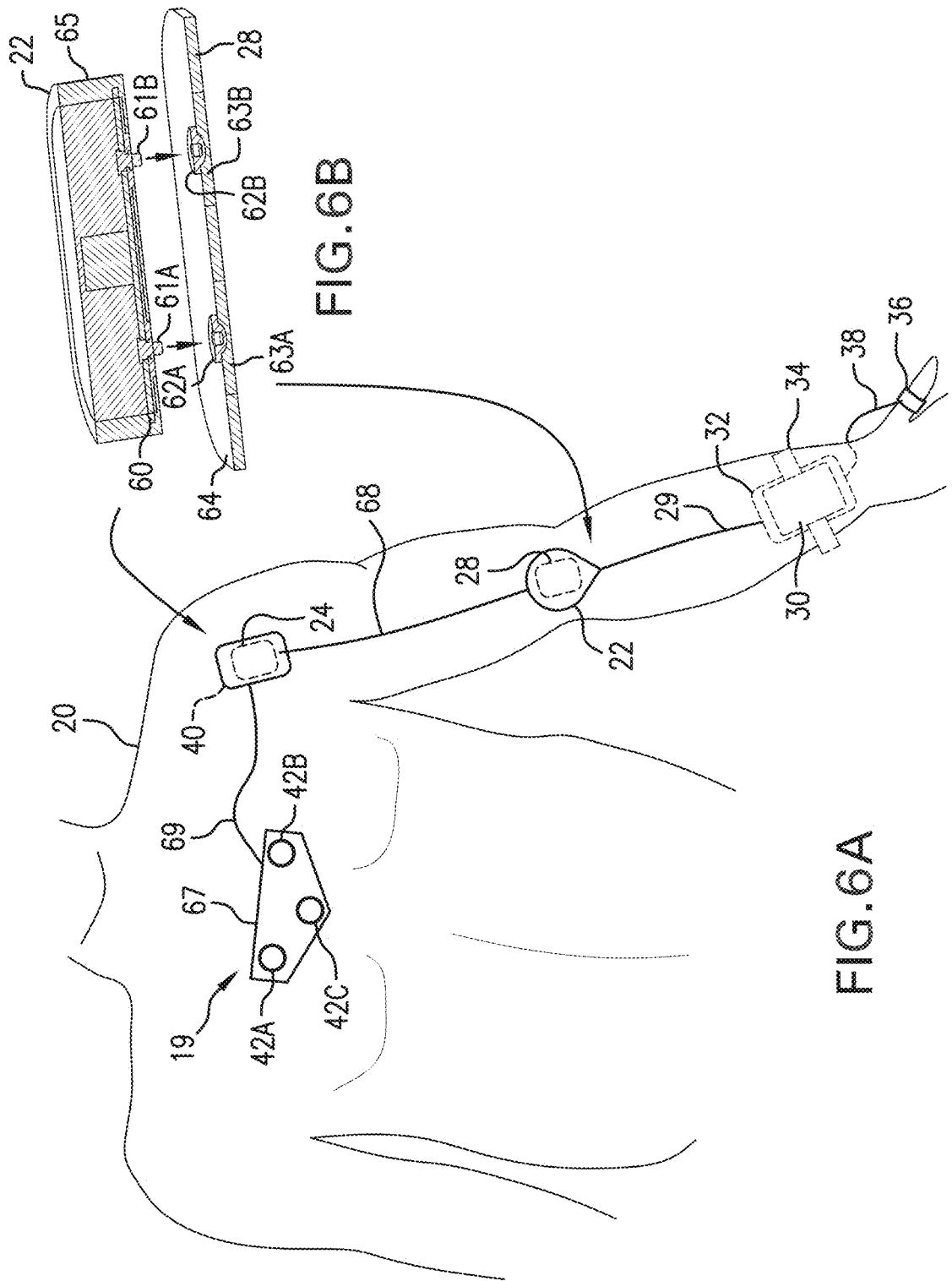

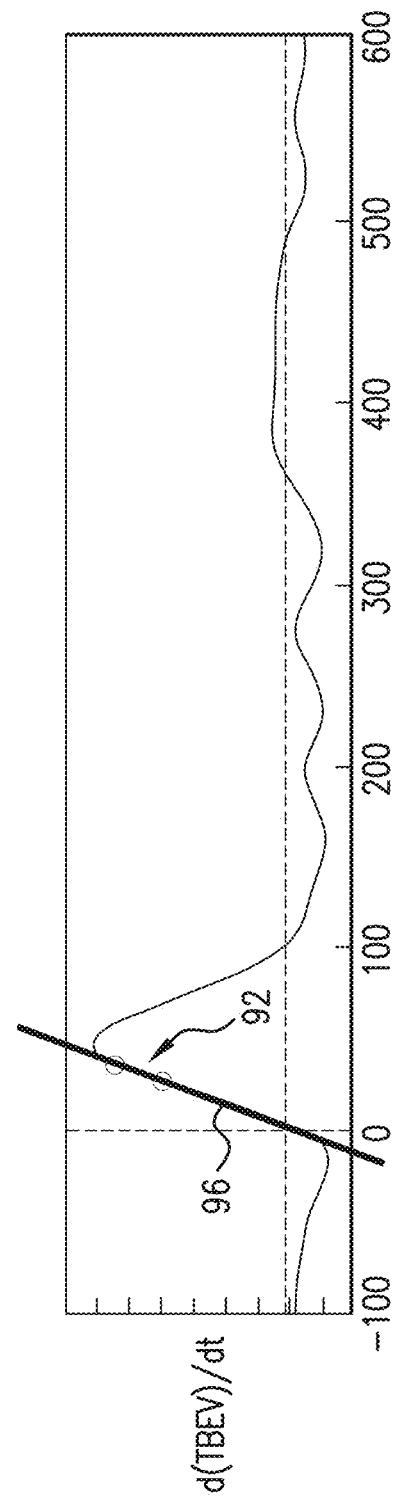

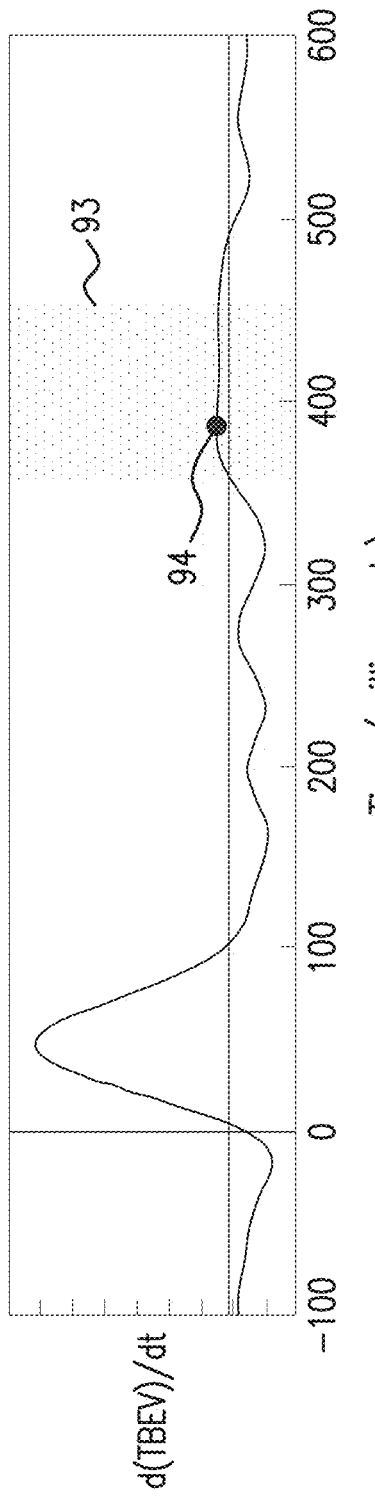
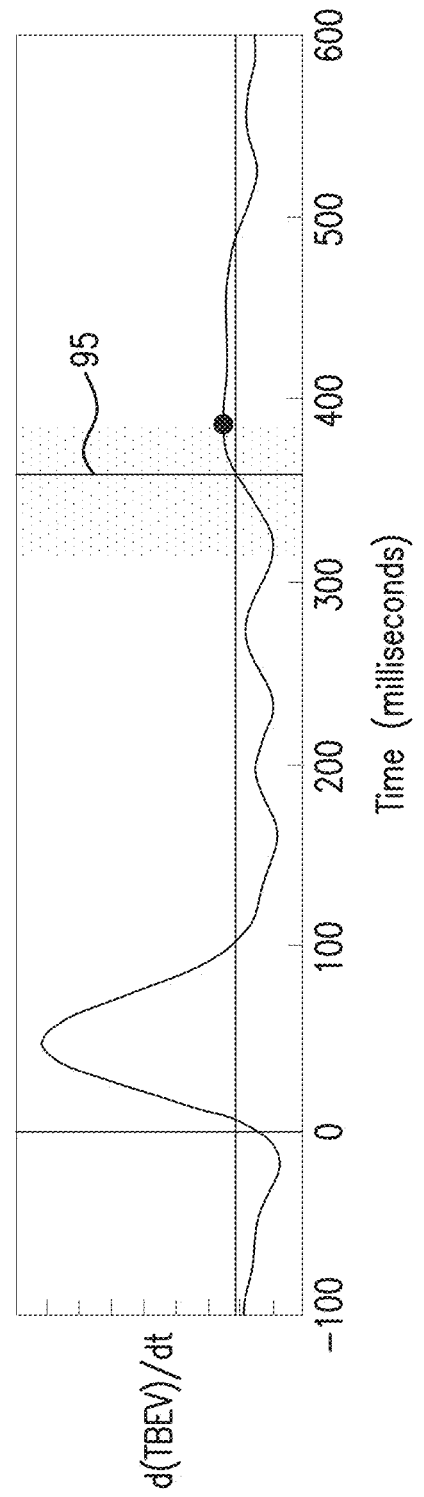
FIG.13C
FIG.13D

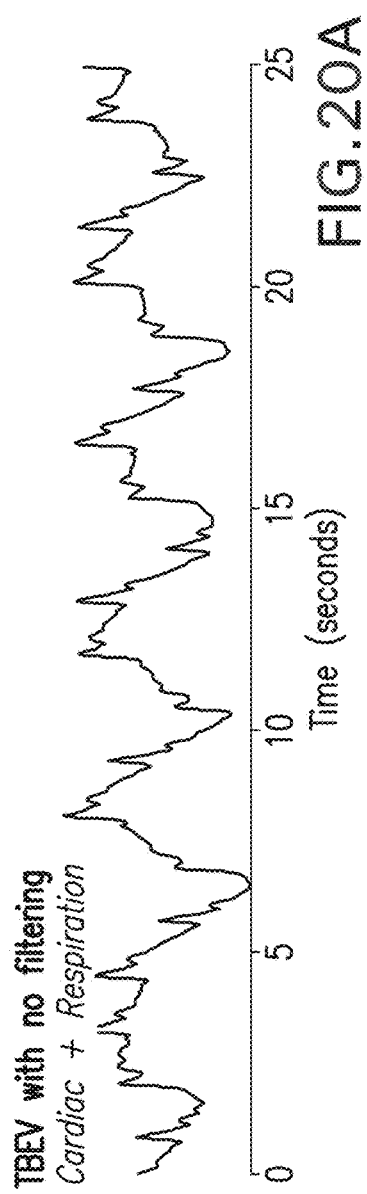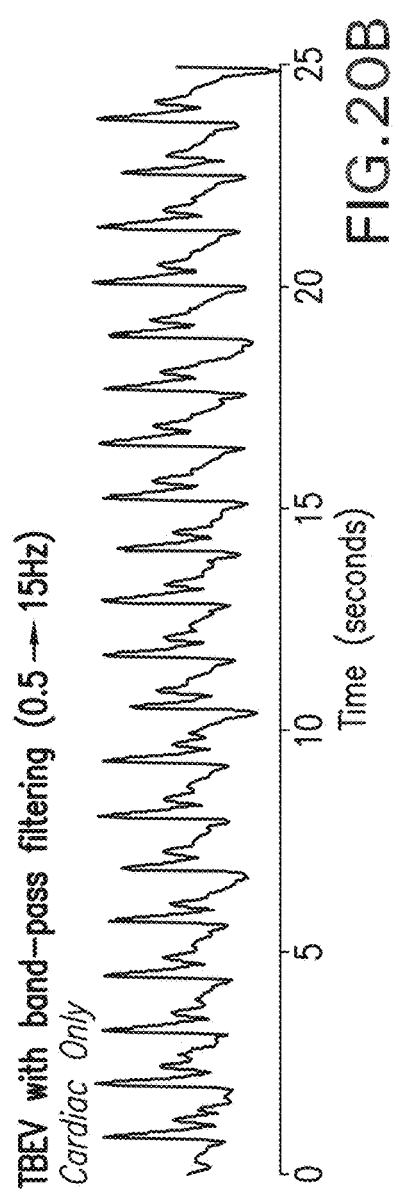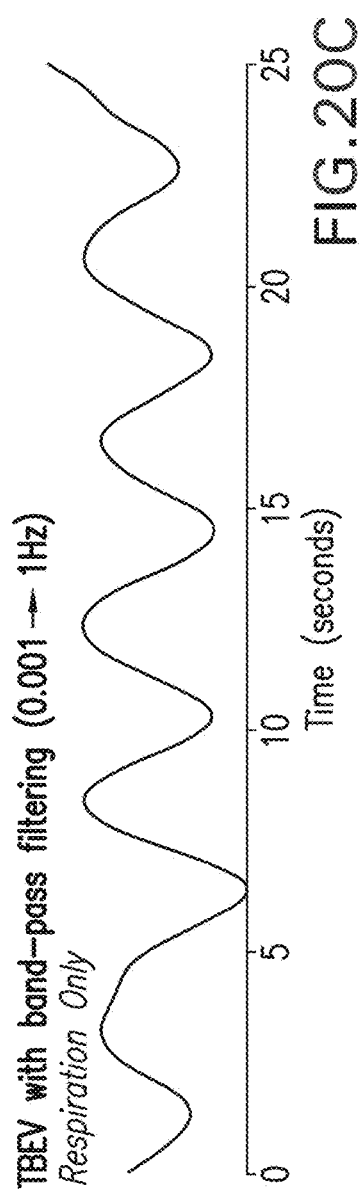

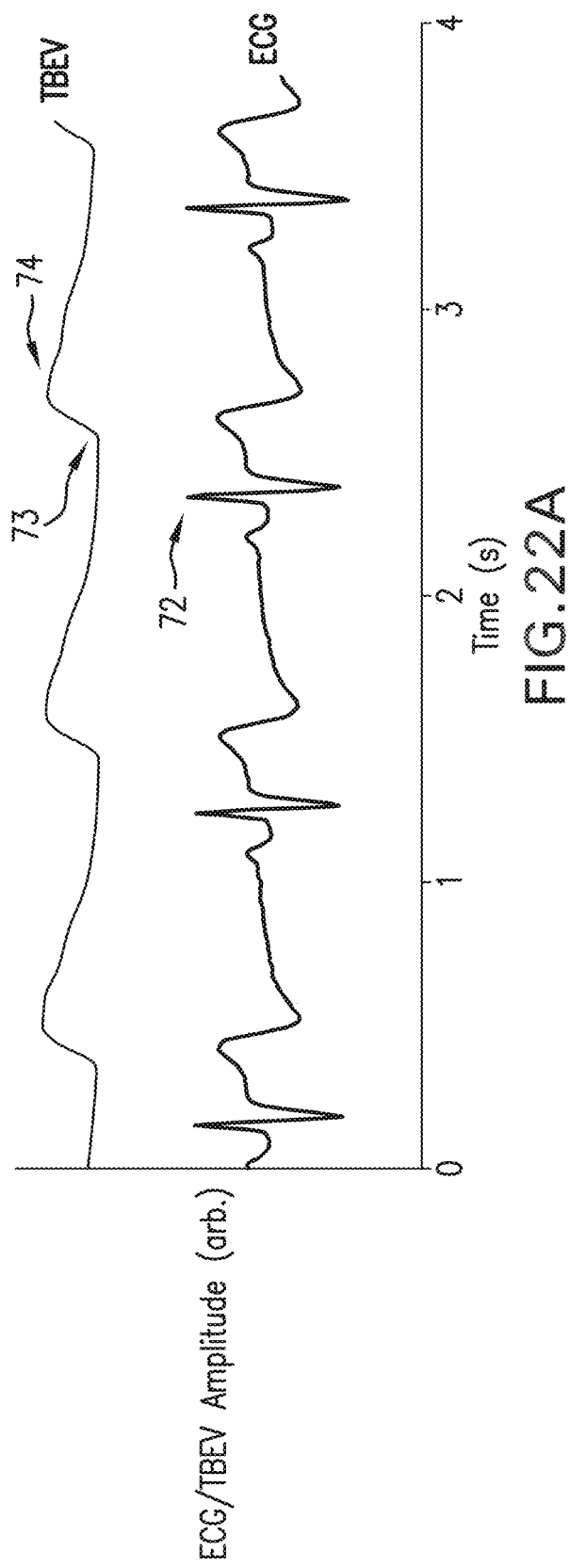
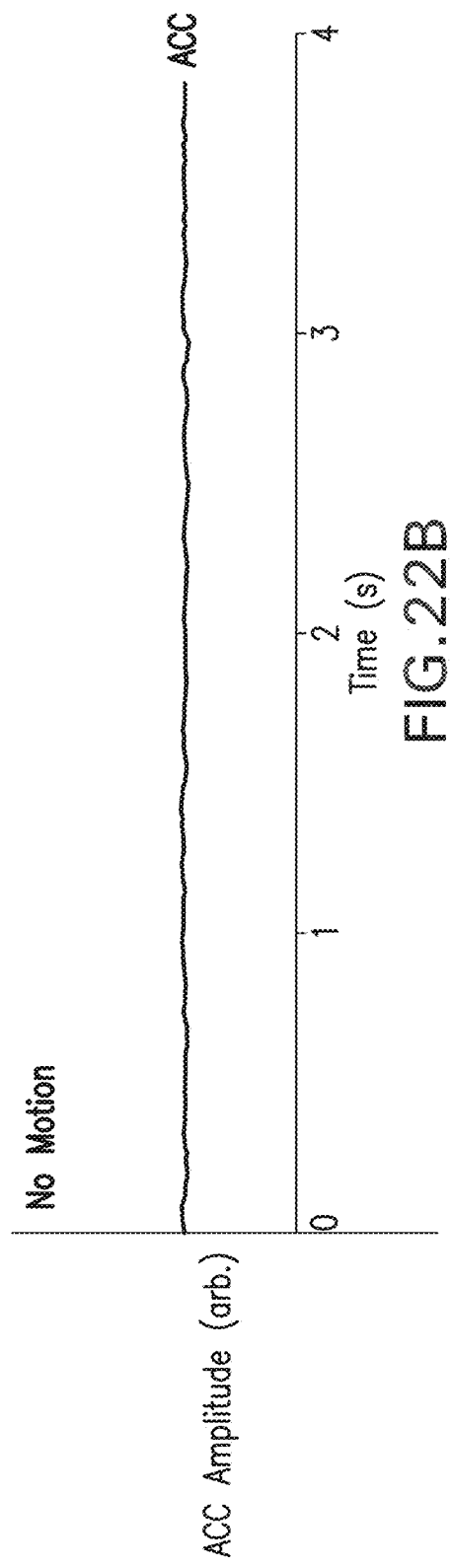
FIG.22A
FIG.22B

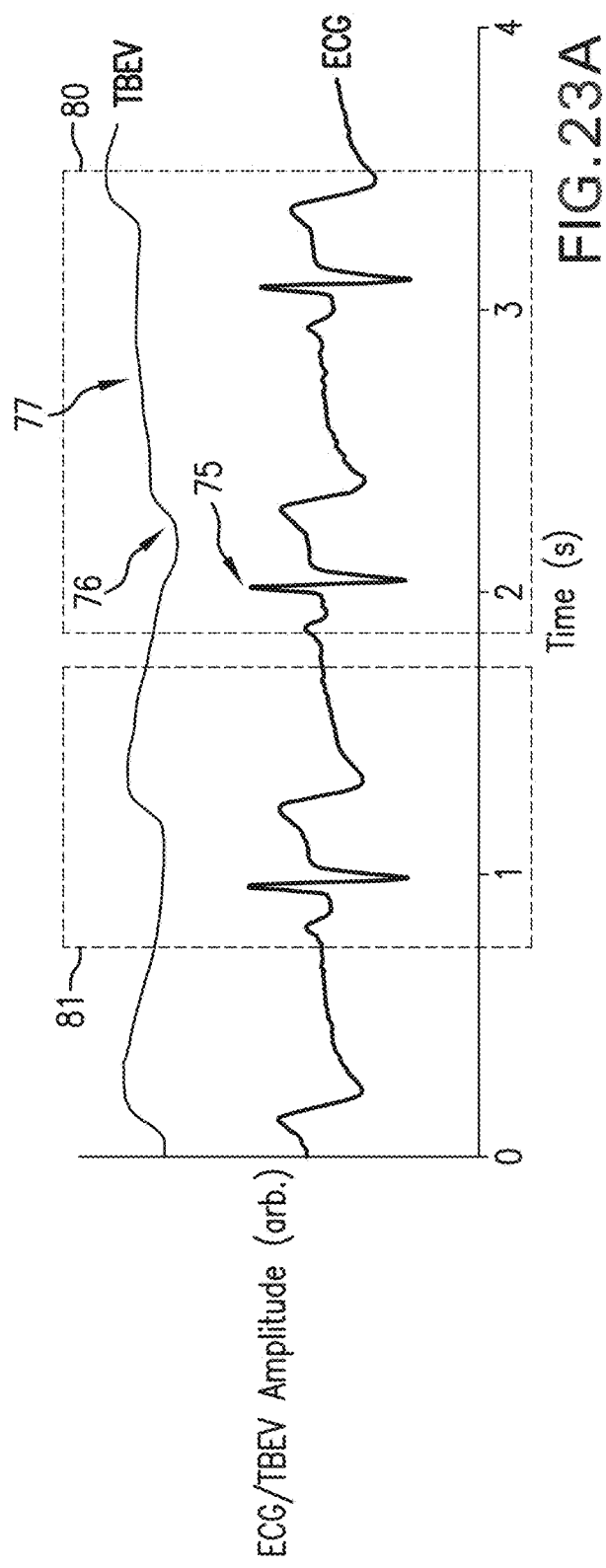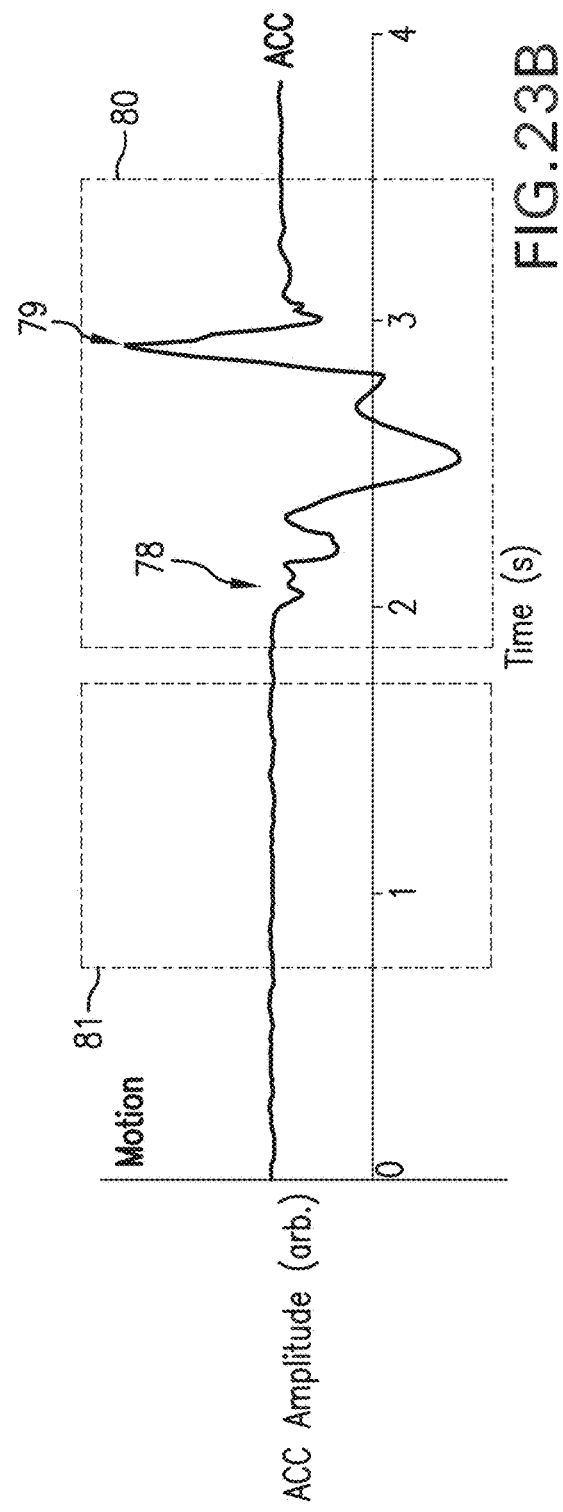

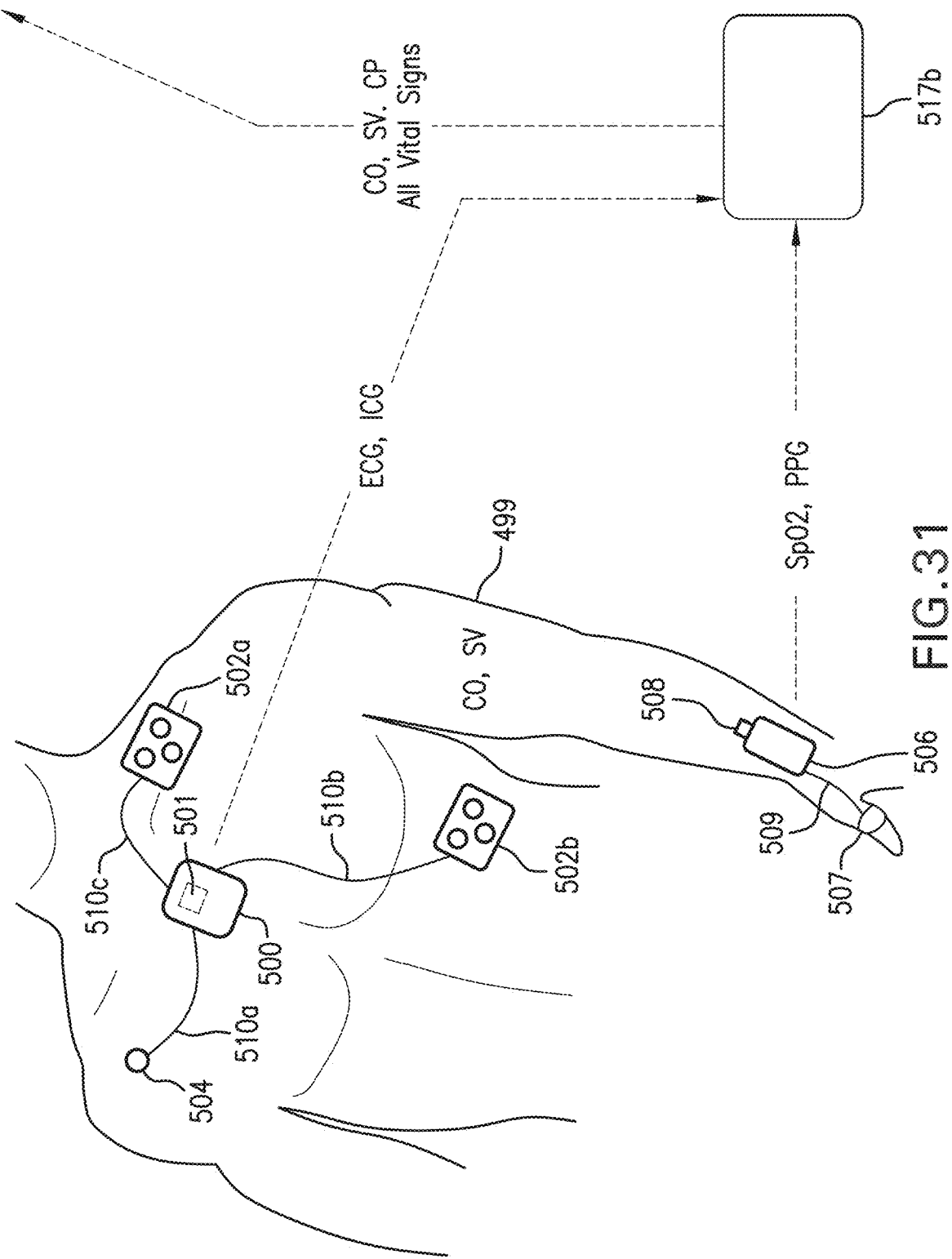

BODY-WORN SYSTEM FOR CONTINUOUS, NONINVASIVE MEASUREMENT OF CARDIAC OUTPUT, STROKE VOLUME, CARDIAC POWER, AND BLOOD PRESSURE

CROSS REFERENCES TO RELATED APPLICATIONS

This application claims priority from a Provisional Application entitled 'BODY-WORN SYSTEM FOR CONTINUOUS, NONINVASIVE MEASUREMENT OF CARDIAC OUTPUT, STROKE VOLUME, AND BLOOD PRESSURE', U.S. Ser. No. 61/427,756, filed Dec. 28, 2010, which is hereby incorporated by reference in its entirety.

STATEMENT REGARDING FEDERALLY SPONSORED RESEARCH OR DEVELOPMENT

Work for some of the components described in this patent application was sponsored by the Department of Defense under contract W81XWH-11-2-0085.

BACKGROUND OF THE INVENTION

Field of the Invention

The present invention relates to medical devices for monitoring cardiovascular properties, e.g. cardiac output (CO), stroke volume (SV), and continuous non-invasive blood pressure (cNIBP).

Description of the Related Art

CO is typically measured in a hospital setting and, informally, indicates how efficiently a patient's heart pumps blood through their arterial tree. More specifically, CO, with units of liters/minute, describes the time-dependent volume of blood ejected from the left ventricle into the aorta; it indicates how well the patient's heart delivers blood-borne oxygen, nutrients, and other substances to the cells in the body. CO is the product of heart rate (HR) and SV, where SV is defined as the mathematical difference between left ventricular end diastolic volume (EDV) and end systolic volume (ESV), i.e.:

$$CO = SV \times HR \quad (1)$$

Combining CO and mean arterial blood pressure (MAP) into a single value, called 'cardiac power' (CP), provides a particularly valuable prognostic variable for monitoring patients suffering from cardiac conditions such as congestive heart failure (CHF), and is an independent predictor of mortality that can be measured non-invasively using cardiopulmonary exercise testing. Specifically, CP is defined as:

$$CP = CO \times MAP \quad (2)$$

Measuring CO and SV in a continuous, non-invasive manner with high clinical accuracy has often been considered a 'holy grail' of medical-device monitoring. Most existing techniques in this field require in-dwelling catheters, which in turn can harm the patient, are inherently inaccurate in the critically, and require a specially trained operator. For example, current 'gold standards' for this measurement are thermodilution cardiac output (TDCO) and the Fick Oxygen Principal (Fick). However both TDCO and Fick are highly invasive techniques that can cause infection and other complications, even in carefully controlled hospital environments. In TDCO, a pulmonary artery catheter (PAC), also known as a Swan-Ganz catheter, is typically inserted into the right portion of the patient's heart. Procedurally a bolus (typically 10 ml) of glucose or saline that is cooled to a known temperature is injected through the PAC. A temperature-measuring device within the PAC, located a known distance away (typically 6-10 cm) from where fluid is injected, measures the progressively increasing temperature of the diluted blood. CO is then estimated from a measured time-temperature curve, called the 'thermodilution curve'. The larger the area under this curve, the lower the cardiac output. Likewise, a smaller the area under the curve implies a shorter transit time for the cold bolus to dissipate, hence a higher CO.

Fick involves calculating oxygen consumed and disseminated throughout the patient's blood over a given time period. An algorithm associated with the technique incorporates consumption of oxygen as measured with a spirometer with the difference in oxygen content of centralized blood measured from a PAC and oxygen content of peripheral arterial blood measured from an in-dwelling cannula.

Both TD and Fick typically measure CO with accuracies between about 0.5-1.0 l/min, or about +/−20% in the critically ill.

Several non-invasive techniques for measuring SV/CO/CP have been developed with the hope of curing the deficiencies of Fick and TD. For example, Doppler-based ultrasonic echo (Doppler/ultrasound) measures blood velocity using the well-known Doppler shift, and has shown reasonable accuracy compared to more invasive methods. But both two and three-dimensional versions of this technique require a specially trained human operator, and are thus, with the exception of the esophageal Doppler technique, impractical for continuous measurements. CO/SV can also be measured with techniques that rely on electrodes placed on the patient's torso that inject and then collect a low-amperage, high-frequency modulated electrical current. These techniques, based on electrical bioimpedance and called 'impedance cardiography' (ICG), 'electrical cardiometry velocimetry' (ECV), and 'bioreactance' (BR), measure a time-dependent electrical waveform that is modulated by the flow of blood through the patient's thorax. Blood is a good electrical conductor, and when pumped by the heart can further modulate the current injected by these techniques in a manner sensitive to the patient's CO. During a measurement, ICG, ECV, and BR each extract properties called left ventricular ejection time (LVET) and pre-injection period (PEP) from time-dependent ICG and ECG waveforms. A processor then analyzes the waveform with an empirical mathematical equation, shown below in Eq. 2, to estimate SV. CO is then determined from the product of SV and HR, as described above in Eq. 1.

ICG, ECV, and BR all represent a continuous, non-invasive alternative for measuring CO/SV, and in theory can be conducted with an inexpensive system and no specially trained operator. But the medical community has not embraced such methods, despite the fact that clinical studies have shown them to be effective with some patient populations. In 1992, for example, an analysis by Fuller et al. analyzed data from 75 published studies describing the correlation between ICG and TD/Fick (Fuller et al., *The validity of cardiac output measurement by thoracic impedance: a meta-analysis*; Clinical Investigative Medicine; 15: 103-112 (1992)). The study concluded using a meta analysis wherein, in 28 of these studies, ICG displayed a correlation of between r=0.80-0.83 against TDCO, dye dilution and Fick CO. Patients classified as critically ill, e.g. those suffering from acute myocardial infarction, sepsis, and excessive lung fluids, yielded worse results. Further impeding commercial acceptance of these techniques is the tendency of ICG monitors to be relatively bulky and similar in both size and complexity to conventional vital signs monitors. This means two large and expensive pieces of monitoring equipment may need to be located bedside in order to monitor a patient's vital signs and CO/SV. For this and other reasons, impedance-based measurements of CO have not achieved widespread commercial success.

ICG-based methodologies for measuring CO/SV have evolved since Fuller's analysis. For example, it has recently been shown that the dimensionless peak rate of change of the trans-thoracic electrical impedance pulse variation, which is defined as the maximum value of the derivative of the ICG waveform $(dZ/dt)_{max}$ divided by the base impedance ($Z_o$), is an acceleration analog (with units of $1/s^2$). When subjected to square root transformation this yields ohmic mean velocity $[(dZ/dt)_{max}/Zo]^{0.5}$. These parameters are described in detail in U.S. Pat. Nos. 7,740,590 and 7,261,697, the contents of which are fully incorporated herein by reference. Reasonable facsimiles of SV can be obtained when this value is multiplied by LVET and a volume conductor ($V_c$) allometrically related by body mass to the intrathoracic blood volume. As compared to CO measured with TDCO and transesophageal echocardiography, good to high correlation and limits of agreement within +/−30% are reported.

While most ICG measurements are conducted on the thorax, there is good evidence in the literature implying that left ventricular SV can be obtained from the upper extremity, and specifically the brachium. For example, Chemla et al. showed that peak aortic blood acceleration is highly correlated with peak brachial artery blood acceleration (r=0.79) (see, e.g., Chemla et al., *Blood flow acceleration in the carotid and brachial arteries of healthy volunteers: respective contributions of cardiac performance and local resistance*; Fundam Clin Pharmacol; 10: 393-399 (1996)). This study also demonstrated that, while brachial blood velocity is affected by downstream vasoactivity, peak brachial blood acceleration is solely affected by the upstream β-adrenergic influences of cardiac impulse formation. This suggests that square root transformation of brachial $(dZ/dt)_{max}/Z_o$ may yield accurate estimations of SV when multiplied by LVET and a Vc of appropriate magnitude. Stanley et al. showed that the maximum early systolic upslope of the transthoracic and brachial impedance changes ($\Delta Z$) are identical, indicating that they are linearly correlated (see, e.g. Stanley et al., *Multi-channel electrical bioimpedance: a new noninvasive method to simultaneously measure cardiac and peripheral blood flow*; J Clin Monit Comput; 21: 345-51 (2007)). This implies that, despite being of different magnitudes, the peak rate of change of the trans-thoracic and trans-brachial impedance changes can both be used to calculate SV. Finally, Wang et al. demonstrated that impedance changes ($\Delta Z(t)$) in the forearm are highly correlated with Doppler-derived SV, showing a correlation coefficient of r=0.86 (see, e.g. Wang et al., *Evaluation of changes in cardiac output from the electrical impedance waveform in the forearm*; Physiol Meas; 28: 989-999 (2007)).

CO/SV can also be estimated from a time-dependent arterial blood pressure waveform measured, e.g., with a tonometer or in-dwelling arterial catheter. Algorithms can be used to extract pulse pressure (PP) and other contour-related features from these waveforms, which are then processed to estimate CO/SV. Unfortunately both the heart and its associated vessels can function independently and sometimes paradoxically, so changes in parameters like PP may both reflect and mask changes in CO/SV. In other words, measurements of CO using time-dependent arterial waveforms represent a combination of cardiac and vascular function.

Pulse arrival time (PAT), defined as the transit time for a pressure pulse launched by a heartbeat in a patient's arterial system, has been shown in a number of studies to correlate to both systolic (SYS) and diastolic (DIA) blood pressures. In these studies, PAT is typically measured with a conventional vital signs monitor that includes separate modules to determine both an electrocardiogram (ECG) and a value for pulse oximetry (SpO2). During a PAT measurement, multiple electrodes typically attach to a patient's chest to determine a time-dependent component of the ECG waveform characterized by a sharp spike called the 'QRS complex'. The QRS complex indicates an initial depolarization of ventricles within the heart and, informally, marks the beginning of the heartbeat and a pressure pulse that follows. SpO2 is typically measured with a bandage or clothespin-shaped sensor that attaches to a patient's finger, and includes optical systems operating in both red and infrared spectral regions. A photodetector measures radiation emitted from the optical systems that transmits through the patient's finger. Other body sites, e.g., the ear, forehead, and nose, can also be used in place of the finger. During a measurement, a microprocessor analyses both red and infrared radiation measured by the photodetector to determine time-dependent waveforms corresponding to the different wavelengths, each called a photoplethysmogram waveform (PPG). From these a SpO2 value is calculated Time-dependent features of the PPG waveform indicate both pulse rate and a volumetric absorbance change in an underlying artery (e.g., in the finger) caused by the propagating pressure pulse.

Typical PAT measurements determine the time separating a maximum point on the QRS complex (indicating the peak of ventricular depolarization) and a portion of the PPG waveform (indicating the arrival of the pressure pulse). PAT depends primarily on arterial compliance, the propagation distance of the pressure pulse (which is closely approximated by the patient's arm length), and blood pressure. To account for patient-specific properties, such as arterial compliance, PAT-based measurements of blood pressure are typically 'calibrated' using a conventional blood pressure cuff. Typically during the calibration process the blood pressure cuff is applied to the patient, used to make one or more blood pressure measurements, and then removed. Going forward, the calibration measurements are used, along with a change in PAT, to determine the patient's blood pressure and blood pressure variability. PAT typically relates inversely to blood pressure, i.e., a decrease in PAT indicates an increase in blood pressure.

A number of issued U.S. Patents describe the relationship between PAT and blood pressure. For example, U.S. Pat. Nos. 5,316,008; 5,857,975; 5,865,755; and 5,649,543 each describe an apparatus that includes conventional sensors that measure ECG and PPG waveforms, which are then processed to determine PAT.

SUMMARY OF THE INVENTION

The invention provides a small-scale, body-worn monitor for measuring SV/CO/CP, along with cNIBP, HR, respiratory rate (RR), SpO2, and body temperature (TEMP), motion, and posture. Measurements of CO/SV are based on a measurement technique called 'transbrachial electro-velocimetry' (TBEV), which is described in detail below. TBEV measurements yield two time-dependent waveforms: Zo, which represents a base impedance in the brachial region, and is sensitive to slowly varying properties such as blood volume; and $\Delta Z(t)$, which features heartbeat-induced pulses that vary in contour as blood flows through the brachium during both systole and diastole. These waveforms are measured from the patient's brachium, a region that is somewhat immune to pulmonary ventilatory affects that can complicate conventional ICG measurements obtained from the thorax. Collectively, an algorithm running on a microprocessor within the body-worn monitor analyzes features analysis of both Zo and ΔZ(t) to determine values for each TBEV measurement. More specifically, to determine SV/CO/CP values, the monitor relies on a 'hybrid measurement' that collectively processes combinations of time-dependent PPG, ECG, and TBEV waveforms, along with physiological parameters (e.g. blood pressure values) extracted from these waveforms, measured by the body-worn monitor. From these waveforms parameters such as LVET and PEP can be estimated and used in a mathematical relationship to continuously and accurately estimate SV/CO/CP values, as described in detail below. Once determined, they are combined with conventional vital signs, and wirelessly transmitted by the body-worn monitor to a central station to effectively monitor the patient.

The TBEV waveform is measured with a small module that connects to a first set of adhesive electrodes worn in the patient's clavicle/brachial (CB) region. This region roughly extends from areas near the tip of the shoulder (proximal to the axilla) to the elbow (proximal to the antecubital fossa). ECG waveforms are measured with a small module that connects to second set of adhesive electrodes that are typically worn on the patient's thorax in a conventional Einthoven's triangle configuration. Both the TBEV and ECG modules also include a 3-axis accelerometer that measures acceleration waveforms (ACC) that are sensitive to motion. Both accelerometers measure, for example, breathing-induced chest wall excursions that can be processed to estimate RR, as well as larger scale motion that can be processed to determine motion-related properties such as activity level, posture, degree/magnitude of motion, and frequency of motion.

During a measurement, the TBEV and ECG modules transmit waveforms and numerical information through either a wired or wireless connection to a wrist-worn transceiver. The transceiver also connects to an optical sensor, worn on the patient's thumb, that measures PPG waveforms generated with optical systems featuring red (~600 nm) and infrared (~900 nm) light-emitting diodes (LEDs). These waveforms can be processed to determine values of SpO2. The wrist-worn transceiver also includes an internal accelerometer that measures ACC waveforms associated with hand motions. Both PPG waveforms, along with the ECG waveforms, can be processed to determine cNIBP values.

The TBEV component of the hybrid measurement is measured by injecting a high-frequency, low-amperage alternating current (AC) field along the course of the brachial artery in the CB region, followed by simultaneously sensing and signal processing voltage changes produced within the current field. The fundamental rational for TBEV derives from the direct proportionality and high correlation observed between peak ascending aortic and peak brachial artery blood flow acceleration. This technique is in diametric opposition to the generally accepted volumetric theory, an alternative approach that suggests it is the velocity-induced peak rate of change in the specific resistance of axially-directed flowing blood that causes a time-dependent change in the measured impedance. Computationally, TBEV-determined SV is obtained by taking the square root of the peak rate of change of electrical impedance pulse variation divided by the base impedance as measured in the CB region, i.e. $[(dZ/dt)_{max}/Zo]^{0.5}$. This parameter is then multiplied by LVET and a constant $V_c$ to yield SV.

The body-worn monitor simultaneously provides a technique for measuring cNIBP, based on either PAT, pulse transit time (PTT) or vascular transit time (VTT), as described in more detail in the above-referenced patent applications. These documents describe cNIBP measurements made using the 'Composite Method', described in detail below, which features a number of improvements over conventional PAT and PTT measurements.

Upon completion of a measurement, the body-worn monitor wirelessly transmits waveforms, vital signs, and SV/CO/CP values to a remote monitor, such as a personal computer (PC), workstation at a nursing station, tablet computer, personal digital assistant (PDA), or cellular telephone. Typically the wireless transmitter is within the wrist-worn transceiver, which also displays and further analyzes this information. Both the remote monitor and the wrist-worn transceiver can additionally include a barcode scanner, touch screen display, camera, voice and speaker system, and wireless systems that operate with both local-area networks (e.g. 802.11 or 'WiFi' networks) and wide-area networks (e.g. the Sprint network).

In one aspect, for example, the invention provides a system for measuring both SV and CO from a patient. The system features an impedance sensor, connected to at least two patient-worn electrodes, and featuring an impedance circuit that processes signals from the at least two electrodes to measure an impedance signal from the patient. An optical sensor within the system connects to an optical probe, and features an optical circuit that measures at least one optical signal from the patient. A body-worn processing system operably connects to both the impedance sensor and the optical sensor and receives and processes the impedance signal to determine a first value of SV and CO. It then receives the optical signal and processes it to determine a second value of these parameters. Finally, the processing system collectively processes both the first and second values of SV and CO to determine a third value of these parameters, which it then reports to a display device.

In another aspect, the invention provides a similar system that also features an ECG sensor, connected to at least two body-worn electrodes, and featuring an ECG circuit. The ECG circuit is configured to process signals from the electrodes to measure an ECG waveform and HR value. A processing system connects to the impedance, optical, and ECG sensors, and receives time-dependent waveforms from each of these systems. It then collectively processes the ECG and optical signals to determine a blood pressure value, and then processes the blood pressure value to estimate SV and CO.

In another aspect, the invention provides a similar system that features ECG, impedance, and optical sensors. Collectively these sensors generate signals that are processed to determine a collection of SV 'estimators'. The various estimators are then processed with a variety of algorithms to estimate stroke volume.

In another aspect the invention provides a method for determining SV that features the following steps: (a) measuring an impedance signal with an impedance sensor operably connected to the body-worn monitor; (b) measuring an optical signal with an optical sensor; (c) processing the impedance signal to determine a value of $(dZ/dt)_{max}$; (d) processing the optical signal to determine a value of SFT; and (e) collectively processing $Z_0$, $(dZ/dt)_{max}$ and SFT to determine the SV.

In another aspect, the invention provides a method of determining cardiac power, which as described in detail below is the product of CO and MAP. Here, CO is determined by processing an ECG waveform to determine a heart rate value, and a combination of impedance and optical waveforms to determine SV. MAP is then calculated from a PAT value determined from PPG and ECG waveforms. Alternatively, MAP is calculated from a VTT value determined from TBEV and PPG waveforms. In both cases, the Composite Method processes either PAT or PTT to determine MAP.

In another aspect, the invention provides a body-worn system for measuring a SV value from a patient. The body-worn system features a TBEV module that includes an electrical circuit configured to inject a current proximal to the patient's brachium. The circuit's bottom portion includes a pair of electrical connectors that are configured to snap into a pair of mated connectors disposed on a first electrode, with a first connector configured to inject the current into a first portion of the electrode, and a second connector configured to measure signals from a second portion of the electrode that relate to a voltage. An analog circuit then processes the signals from the second connector to generate a voltage value. A processor interfaced to the analog circuit converts the voltage value, or a value calculated therefrom, into a time-dependent resistance value, and then converts the time-dependent resistance value into a SV value.

In yet another aspect, the invention provides a method for determining SV from a patient that includes the following steps: (a) measuring a motion waveform with a first motion sensor; (b) processing the motion waveform with a motion algorithm to determine a motion-related parameter; (c) comparing the motion-related parameter to a pre-determined threshold parameter to determine if the patient's motion exceeds an acceptable level; (d) measuring an impedance waveform from the patient with an impedance sensor if the patient's motion does not exceed an acceptable level; and (e) calculating a SV value from the impedance waveform if the patient's motion does not exceed an acceptable level.

The Composite Method for cNIBP is described in detail in the following patent application, the contents of which are fully incorporated herein by reference: BODY-WORN SYSTEM FOR MEASURING CONTINUOUS NON-INVASIVE BLOOD PRESSURE (cNIBP), U.S. Ser. No. 12/650,354, filed Nov. 15, 2009. It includes both pressure-dependent and pressure-free measurements, and is based on the discovery that PAT and the PPG waveform used to determine it are strongly modulated by an applied pressure. During a pressure-dependent measurement, also referred to herein as an 'indexing measurement', two events occur as the pressure gradually increases to the patient's systolic pressure: 1) PAT increases, typically in a non-linear manner, once the applied pressure exceeds diastolic pressure; and 2) the magnitude of the PPG's amplitude systematically decreases, typically in a linear manner, as the applied pressure approaches systolic pressure. The applied pressure gradually decreases blood flow and consequent blood pressure in the patient's arm, and therefore induces the pressure-dependent increase in PAT. Each of the resulting pairs of PAT/blood pressure readings measured during the period of applied pressure can be used as a calibration point. Moreover, when the applied pressure equals SYS, the amplitude of the PPG waveform is completely eliminated, and PAT is no longer measurable. Collectively analyzing both PAT and the PPG waveform's amplitude over a suitable range, along with the pressure waveform using techniques borrowed from conventional oscillometry, yields the patient's SYS, DIA, and MAP, along with a patient-specific slope relating PAT and MAP. From these parameters the patient's cNIBP can be determined without using a conventional cuff.

A combination of several algorithmic features improves the efficacy of the Composite Method over conventional PAT measurements of cNIBP. For example, sophisticated, real-time digital filtering removes high-frequency noise from the PPG waveform, allowing its onset point to be accurately detected. When processed along with the ECG waveform, this ensures measurement of an accurate PAT and, ultimately, cNIBP value. The pressure-dependent indexing method, which is made during inflation of the arm-worn cuff, yields multiple data points relating PAT and blood pressure during a short (~60 second) measurement. Processing of these data points yields an accurate patient-specific slope relating PAT to cNIBP. Inclusion of multiple accelerometers yields a variety of signals that can determine features like arm height, motion, activity level, and posture that can be further processed to improve accuracy of the cNIBP calculation, and additionally allow it to be performed in the presence of motion artifacts. And a model based on femoral blood pressure, which is more representative of pressure in the patient's core, can reduce effects such as 'pulse pressure amplification' that can elevate blood pressure measured at a patient's extremities.

The Composite Method can also include an 'intermediate' pressure-dependent measurement wherein the cuff is partially inflated. This partially decreases the amplitude of the PPG waveform in a time-dependent manner. The amplitude's pressure-dependent decrease can then be 'fit' with a numerical function to estimate the pressure at which the amplitude completely disappears, indicating systolic pressure.

For the pressure-dependent measurement, a small pneumatic system attached to the cuff inflates the bladder to apply pressure to an underlying artery according to the pressure waveform. The cuff is typically located on the patient's upper arm, proximal to the brachial artery, and time-dependent pressure is measured by an internal pressure sensor, such as an in-line Wheatstone bridge or strain gauge, within the pneumatic system. The pressure waveform gradually ramps up in a mostly linear manner during inflation, and then slowly rapidly deflates through a 'bleeder valve' during deflation. During inflation, mechanical pulsations corresponding to the patient's heartbeats couple into the bladder as the applied pressure approaches DIA. The mechanical pulsations modulate the pressure waveform so that it includes a series of time-dependent oscillations. The oscillations are similar to those measured with an automated blood pressure cuff using oscillometry, only they are measured during inflation rather than deflation. They are processed as described below to determine a 'processed pressure waveform', from which MAP is determined directly, and SYS and DIA are determined indirectly.

Pressure-dependent measurements performed on inflation have several advantages to similar measurements performed on deflation, which are convention. For example, inflation-based measurements are relatively fast and comfortable compared to those made on deflation. Most conventional cuff-based systems using deflation-based oscillometry take roughly four times longer than the Composite Method's pressure-dependent measurement. Inflation-based measurements are possible because of the Composite Method's relatively slow inflation speed (typically 5-10 mmHg/second) and high sensitivity of the pressure sensor used within the body-worn monitor. Moreover, measurements made during inflation can be immediately terminated once systolic blood pressure is calculated. In contrast, conventional cuff-based measurements made during deflation typically apply a pressure that far exceeds the patient's systolic blood pressure; pressure within the cuff then slowly bleeds down below DIA to complete the measurement.

Pressure-free measurements immediately follow the pressure-dependent measurements, and are typically made by determining PAT with the same optical and electrical sensors used in the pressure-dependent measurements. Specifically, the body-worn monitor processes PAT and other properties of the PPG waveform, along with the patient-specific slope and measurements of SYS, DIA, and MAP made during the pressure-dependent measurement, to determine cNIBP.

The invention in general, and particularly the hybrid measurement for SV/CO/CP, features many advantages over conventional techniques used to measure these properties. Compared to TDCO and Fick, for example, the body-worn monitor facilitates continuous, noninvasive measurement of these values that is highly accurate and has a low-risk of detrimental complications, such as infection and pulmonary artery vessel perforation. And unlike measurements based on TDCO, Fick, and Doppler, the hybrid measurement does not require a specially trained observer. TBEV measurements are performed at the brachium, which by itself has several advantages over conventional ICG measurements made from the thorax. For example, complications in the pulmonary system, i.e. intra-thoracic liquids and pulmonary edema, do not affect SV/CO/CP values measured from this region. Similarly, the baseline trans-brachial quasi-static impedance, Zo is not affected by medical equipment sometimes present in the thorax, such as chest tubes, external pacemaker wires, and central venous lines. Typically thoracic ICG measurements require 8 separate electrodes, whereas the TBEV measurement described herein only requires 2 separate electrodes. Finally, without the influence of pulmonary ventilation and pulmonary artery pulsations, the signal-to-noise ratio of waveforms measured from the brachium is relatively high.

These and other advantages of the invention will be apparent for the following detailed description, and from the claims.

BRIEF DESCRIPTION OF THE DRAWINGS

FIG. 5 shows a schematic drawing of a body-worn monitor that performs the hybrid measurement shown in FIG. 1;

FIG. 6A shows a schematic drawing of an alternate embodiment of the body-worn monitor that performs the hybrid measurement shown in FIG. 1;

FIG. 6B shows a three-dimensional drawing of the TBEV module and custom electrode used in the alternate embodiment shown in FIG. 6A;

FIGS. 13A-13D show time-dependent plots of, respectively, a TBEV waveform, a derivative of the TBEV waveform showing fiducial points near a pulse maximum used to determine the pulse's onset, a derivative of the TBEV waveform showing a shaded region indicating where Weissler's regression is used to estimate LVET, and a derivative of the TBEV waveform where SFT is determined;

FIGS. 20A-C show time-dependent plots of, respectively, an unfiltered TBEV waveform showing both cardiac and respiratory events, a TBEV waveform filtered with a 0.5 to 15 Hz band-pass filter showing only cardiac events, and a TBEV waveform filtered with a 0.001 to 1 Hz band-pass filter showing only respiration events;

FIG. 22A shows a time-dependent plot of TBEV and ECG waveforms measured during a period of no motion;

FIG. 22B shows a time-dependent plot of ACC waveforms, measured simultaneously with the TBEV and ECG waveforms of FIG. 22A, during the period of no motion;

FIG. 23A shows time-dependent plots of TBEV and ECG waveforms measured during a period of motion;

FIG. 23B shows a time-dependent plot showing ACC waveforms, measured simultaneously with the TBEV and ECG waveforms of FIG. 22A, during the period of motion;

DETAILED DESCRIPTION OF THE INVENTION

Measurement Overview

Figure 1:
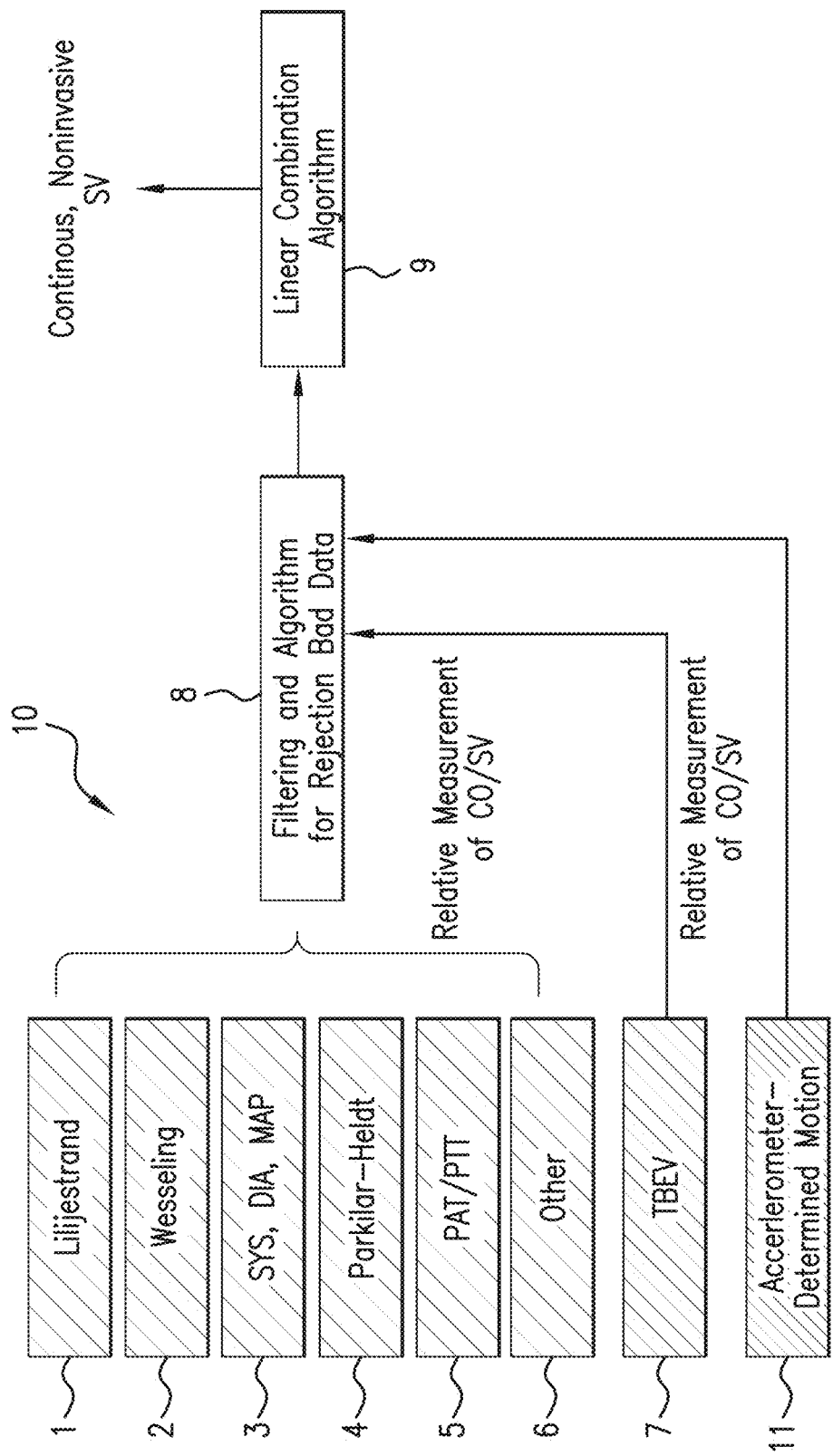
FIG. 1 shows a schematic drawing of an algorithm that performs the hybrid measurement for determining SV/CO/CP values according to the invention.

Referring to FIG. 1, the invention described herein features a body-worn monitor that continuously and non-invasively determines SV from TBEV measurements 7 collected from a patient's CB region, along with a series of SV 'estimators' 1-6 made calculated from cNIBP measurements. The body-worn monitor is described, for example, in the following patent applications, the contents of which are incorporated herein by reference: BODY-WORN VITAL SIGN MONITOR, U.S. Ser. No. 12/560,077, filed Sep. 15, 2009; and BODY-WORN VITAL SIGN MONITOR, U.S. Ser. No. 12/762,726, filed Apr. 19, 2009. SV measurements made using TBEV 7 and the estimators 1-6 can be incorporated into a 'hybrid measurement' 10, operating on a microprocessor within the body-worn monitor, that determines SV and ultimately CO and CP.

TBEV is a variation of conventional bioimpedance techniques, such as ICG, and measures waveforms from the CB region to determine time-dependent parameters such as systolic flow time (SFT), $(dZ/dt)_{max}$, and Zo. These parameters feed into Eq. 3, below, where they are coupled with a static parameter $V_c$ to determine SV.

$$SV = V_C \sqrt{\frac{(dZ/dt)_{max}}{Z_0}} SFT \qquad (3)$$

Here, SV is obtained by taking the square root of the peak rate of change of each TBEV pulse divided by the transbrachial base impedance, Zo. This parameter is then multiplied by SFT and a constant-magnitude $V_c$ to yield SV. The derivation of Eq. 3 is described in detail in U.S. Pat. No. 6,511,438 and in the following reference, the contents of which are fully incorporated herein by reference: Bernstein et al., *Stroke Volume Obtained By Electrical Interrogation of the Brachial Artery: Transbrachial Electrical Bioimpedance Velocimetry. Unpublished manuscript*, submitted 2012. Eq. 3 assumes that $(dZ/dt)_{max}/Z_o$ represents a dimensionless acceleration of blood (with units of $1/s^2$), which is the ohmic analog of peak aortic blood acceleration ($cm/s^2$). Forceful systolic ejection of blood from the left ventricle of the heart aligns the erythrocytes in parallel during systolic flow to generate a pulsatile increase in conductivity. For this model, $V_c$ is estimated entirely from weight, and is independent of any factors that depend on electrode separation.

Along with SV, the body-worn monitor simultaneously measures cNIBP values (SYS, DIA, MAP, and PP) using a cuffless technique called the 'Composite Method', which is described in detail above. According to the hybrid method, SV is determined explicitly from the TBEV waveforms, and can be estimated from the cNIBP values. From these parameters multiple estimators 1-7 are determined which the algorithm 10 collectively processes to determine SV. Additionally, the body-worn monitor features multiple accelerometers that generate time-dependent ACC waveforms, which are then further processed by a motion algorithm 11 to estimate the patient's level of motion. A function for filtering and rejecting bad data 8 processes information from both the estimators 1-7 and the motion algorithm 11 to determine a collection of valid data points, which are then linearly combined with another function 9 to determine final values of SV. The valid data points, for example, are relatively uncorrupted by motion artifacts; they are determined when the motion algorithm 11 compares a parameter extracted from an ACC waveform to a pre-determined 'motion threshold' value. If the parameter exceeds the pre-determined threshold value, the function 8 rejects the corresponding SV values. On the other hand, if the parameter is lower than the pre-determined threshold value, the function 8 approves the corresponding SV value, and it is passed into the linear combination algorithm 9, where it will be processed to determine a final value for SV.

Different threshold values can be applied for SV calculated from TBEV 7, a measurement that is particularly sensitive to motion, and SV estimated from estimators related to blood pressure 1-6, which are less sensitive to motion. For example, the motion algorithm 11 may determine that a small amount of motion is present, and thus the linear combination algorithm 9 relies completely on SV values determined from the estimators related to blood pressure 1-6. Or it may determine that a large amount of motion is present, and in response the linear combination algorithm 9 will not report an SV value. If the motion algorithm 11 determines that no motion is present, the linear combination algorithm 9 typically reports a SV value determined entirely from TBEV 7.

In embodiments, the linear combination algorithm 9 combines different estimators using a simple average or weighted average to determine a single value of SV. More sophisticated approaches can also be used to process the estimators. For example, specific estimators can be selected based on a patient's physiological condition or biometric parameters, e.g. their age, gender, weight, or height.

Once SV is determined, it can be further processed as defined in Eqs. 1, 2 to determine both CO and CP.

Upon completion of a measurement, the body-worn monitor wirelessly transmits SV/CO/CP values, along with conventional vital signs, to a remote processing system. For example, these data may flow through a hospital-based wireless network to a central computer interfaced to an electronic medical records system. From there, medical professionals, such as doctors, nurses, and first responders, can evaluate a constellation of physiological values corresponding to the patient to make a diagnosis. Typically, patients wear the body-worn monitor as they transition from the ambulance, into the hospital, and ultimately to the home.

A TBEV measurement, described in detail below, injects a low-amperage, high-frequency current into the patient's CB region, and monitors a voltage which relates to the time-dependent resistance encountered by the current through Ohm's Law ($V = I \times R$). It is based on the assumption that the brachial artery, which is the only major artery in the CB region, undergoes little volumetric expansion during systole, and thus changes in resistance are due exclusively to acceleration-induced alignment of erythrocytes within this artery. Stated another way, as blood flows through the artery with each heartbeat, the diameter of the brachial artery stays relatively constant, but acceleration of the blood causes the erythrocytes to align. This physiological process consequently increases conductivity, and decreases resistance, in the artery. The time-dependent resistance in the artery is manifested as a first waveform, called $\Delta Z(t)$, which features a series of pulses, each corresponding to a unique heartbeat. A second TBEV waveform, $Z_0$, is filtered to only reflect the baseline impedance of the artery, and is sensitive to relatively low-frequency processes, such as blood volume, interstitial fluids, and occasionally respiration rate.

Estimators for determining SV from blood pressure values include the Lilijestrand 1, Wesseling 2, MAP 3, and Herd 4 estimators. These depend linearly on blood pressure values, and are shown below in Table 1. In this table $SYS_{area}$ refers to the area under the PPG waveform during systole, $\Delta P_n$ is the beat-to-beat blood pressure change, $T_n$ is the duration of the cardiac cycle, and $\tau_n$ is a time constant that governs the intra-cycle dynamics of the Windkessel model.

These estimators are summarized in detail in the following reference, among other places, the contents of which are incorporated herein by reference: Chen, *Cardiac Output Estimation from Arterial Blood Pressure Waveforms using the MIMIC II Database*; Thesis for Masters Degree submitted to the Massachusetts Institute of Technology; (2009); and Parlikar et al., *Model-Based Estimation of Cardiac Output and Total Peripheral Resistance*; unpublished manuscript available lcp.mit.edu/pdf/Parlikar07.pdf. Estimators based on blood pressure can be determined using the Composite Method, or alternatively with a conventional cuff-based method, such as oscillometry or auscultation.

TABLE 1

Estimators for CO

| CO ESTIMATOR | CO FORMULA (CO = k * equation below) |
|---|---|
| Lilijestrand | [(PP/(SYS + DIA)] * HR |
| Wesseling | (163 + HR − 0.48 * MAP) * $SYS_{area}$ * HR |
| MAP | MAP |
| SYS | $SYS_{area}$ * HR |
| ParlikarHeldt | ($\Delta P_n/T_n$ + MAP/$\tau_n$) |
| Herd | (MAP − DIA) * HR |
| Windkessel | PP * HR |

Figure 26:
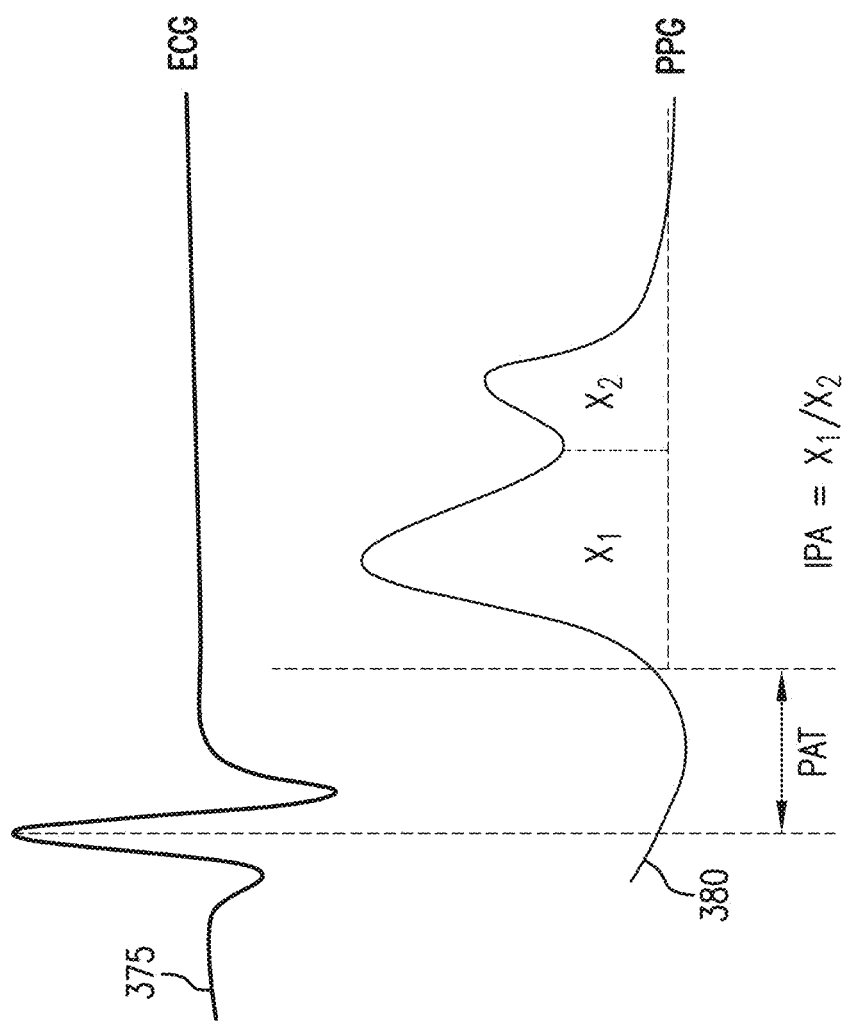
FIG. 26 shows a schematic drawing of ECG and PPG waveforms, and how the PAT determined from these waveforms and the contours of the PPG waveforms can be collectively analyzed to determine an estimator for SV.

Other SV estimators that can be processed by the algorithm include those based on PAT 5, which is determined using PPG and ECG waveforms measured by the body-worn monitor, and is described in the following reference, the contents of which are incorporated by reference: Wang et al., *The non-invasive and continuous estimation of cardiac output using a photoplethysmogram and electrocardiogram during incremental exercise*; Physiol. Meas.; 31: 715-726 (2010). FIG. 26 and Eq. 4, below, indicate Wang's methodology for analyzing PAT, ECG 375, and PPG 380 waveforms to determine a relative value of CO.

$$CO = D \times [C - \ln(PAT)] \times (1 - IPA) \times (1 + IPA)^{-1} \quad (4)$$

In the equation D and C are constants defined in the Wang reference, and IPA is shown schematically in FIG. 26. This theory assumes that the PPG waveform 380 includes a well-defined dichrotic notch allowing the parameters $X_1$, $X_2$, and ultimately IPA to be determined. Integration of an area under the PPG before the notch yields $X_1$, while integration of an area under the PPG after the notch yields $X_2$. IPA is defined as the ratio of $X_1$ to $X_2$. Once determined, PAT and IPA are used in Eq. 4 to yield another estimator of SV/CO/CP.

The PPG waveform, taken by itself, can be analyzed and used as an 'other' estimator 6 for algorithm 10. This waveform represents a time-dependent volumetric expansion of the underlying artery from which it is measured, and is thus different than a traditional cNIBP waveform, such as that measured using an in-dwelling arterial catheter, which represents the time-dependent pressure in the artery. However, PPG and cNIBP waveforms share a similar morphology, particularly over relatively long time periods, and can be analyzed to estimate both blood flow dynamics and hence SV. The following reference, the contents of which are incorporated herein by reference, describes an analysis method for processing waveforms to extract these parameters: Lu et al., *Continuous cardiac output monitoring in humans by invasive and noninvasive peripheral blood pressure waveform analysis*; J Appl Physiol 101: 598-608 (2006).

In still other embodiments, an 'other' estimator 6 for the SV/CO/CP measurement can be based on a measurement technique performed by an external sensor that connects to the body-worn monitor. Such a connection can be made using either wired or wireless means. For example, a technique such as near-infrared spectroscopy (NIRS) can be used to estimate SV as described in the following references, the contents of which are incorporated herein by reference: Soller et al., *Noninvasively determined muscle oxygen saturation is an early indicator of central hypovolemia in humans*; J Appl Physiol 104: 475-481 (2008). A sensor incorporating a NIRS measurement can thus be integrated with the body-worn monitor and attached to the patient's body during a measurement. Values for SV calculated with this sensor are sent to the monitor through the wired or wireless connection, and can be incorporated in the algorithm 10 to further improve the accuracy of the continuous, non-invasive determination of SV. In all cases, the collection of estimators 1-6 relate to CO through a calibration factor (k in Table 1) determined from an absolute measurement of SV, which in the algorithm 10 is provided by the TBEV measurement 7. Typically TBEV determines SV to within about +/−20%. Perhaps more importantly, the estimators 1-6 and TBEV measurement 7 determine SV with completely different methodologies and from different locations on the body. Thus it is possible that combining the measurements into a single algorithm 10 may reduce error caused by well-known physiological effects that are typically isolated to these locations.

Figure 2:
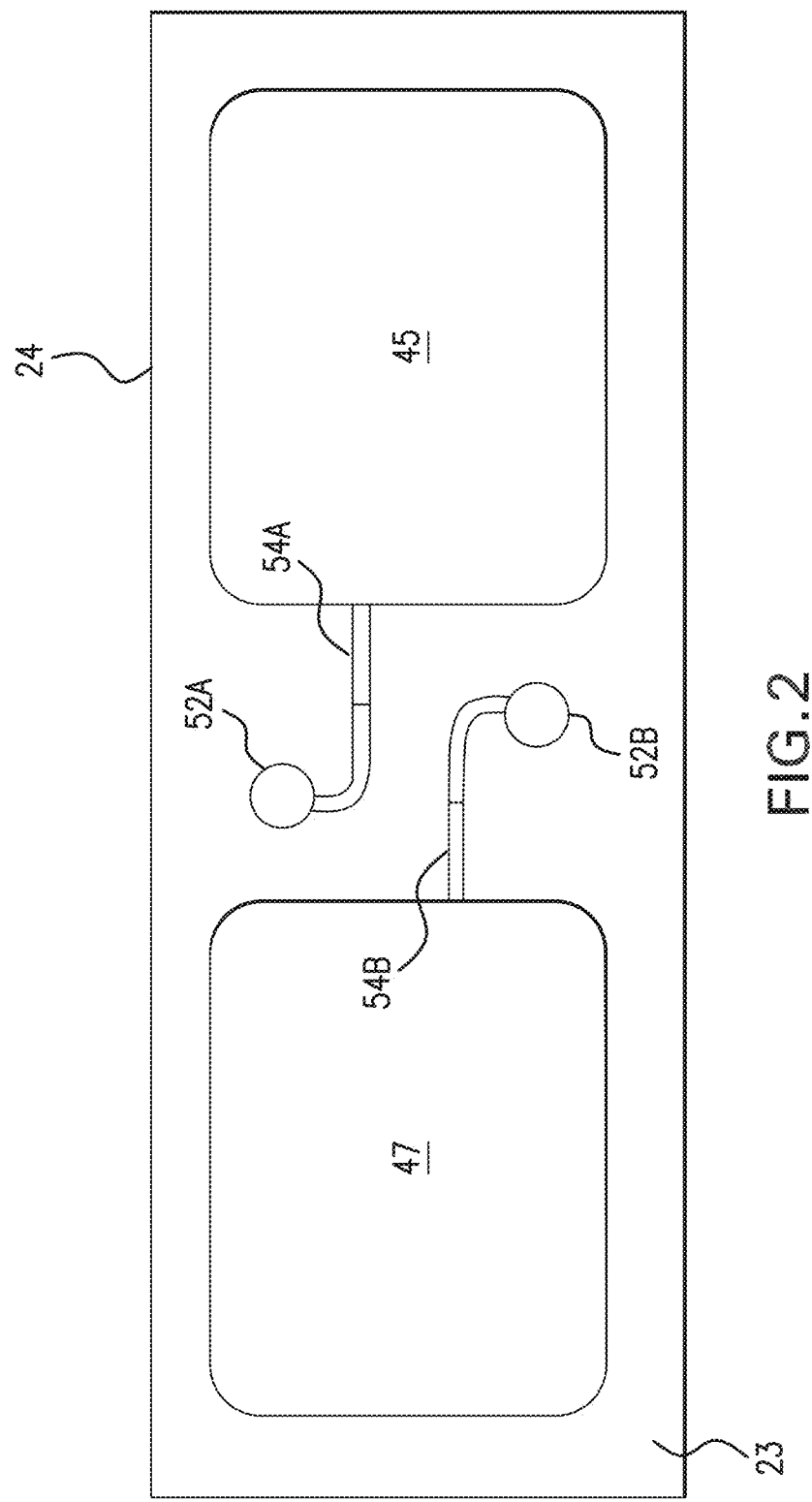
FIG. 2 shows a schematic drawing of the custom electrode patch used to perform TBEV measurements described in FIG. 1.

As shown in FIG. 2, TBEV measurements are typically made with a pair of custom electrodes 24, each featuring two conductive regions 45, 47. The outer conductive region 45 (i.e. the region furthest removed from the CB region) of each electrode 24 injects a low-amperage (<5 mA), high frequency (50-100 kHz) current into the patient's CB region. The inner conductive region 47 then measures the time-dependent voltage across the artery. As described above, variations in this voltage are due to resistance changes caused by blood flowing through the brachial artery, and more specifically due to acceleration-induced alignment of erythrocytes occurring with each heartbeat. This physiology provides a basis for the mathematical model shown above in Eq. 3.

Each conductive region 45 and 47 typically consists of a conductive 'liquid gel' material that roughly matches the impedance properties of human skin. The liquid gel is deposited on top of a conductive substrate coated with a large-area Ag:AgCl film that, in turn, is deposited on top of a flexible substrate 23. The liquid gel, for example, can be a sponge-like material saturated with a conductive gel or fluid. The neighboring conductive regions 45, 47 are electrically isolated from each other, and individually connect through a pair of individual conductive traces 54A, B to a pair of electrical leads 52A, B adhered to the flexible substrate 23. The electrical leads 52A, B, for example, can be metal rivets or posts that easily snap into a corresponding female connector. An insulating adhesive layer (not shown in the figure) dispersed between the conductive regions 45 and 47 electrically isolates these portions of the electrode 24, and is coated with an adhesive that enables it to be securely attached to the patient during a measurement.

Figure 3:
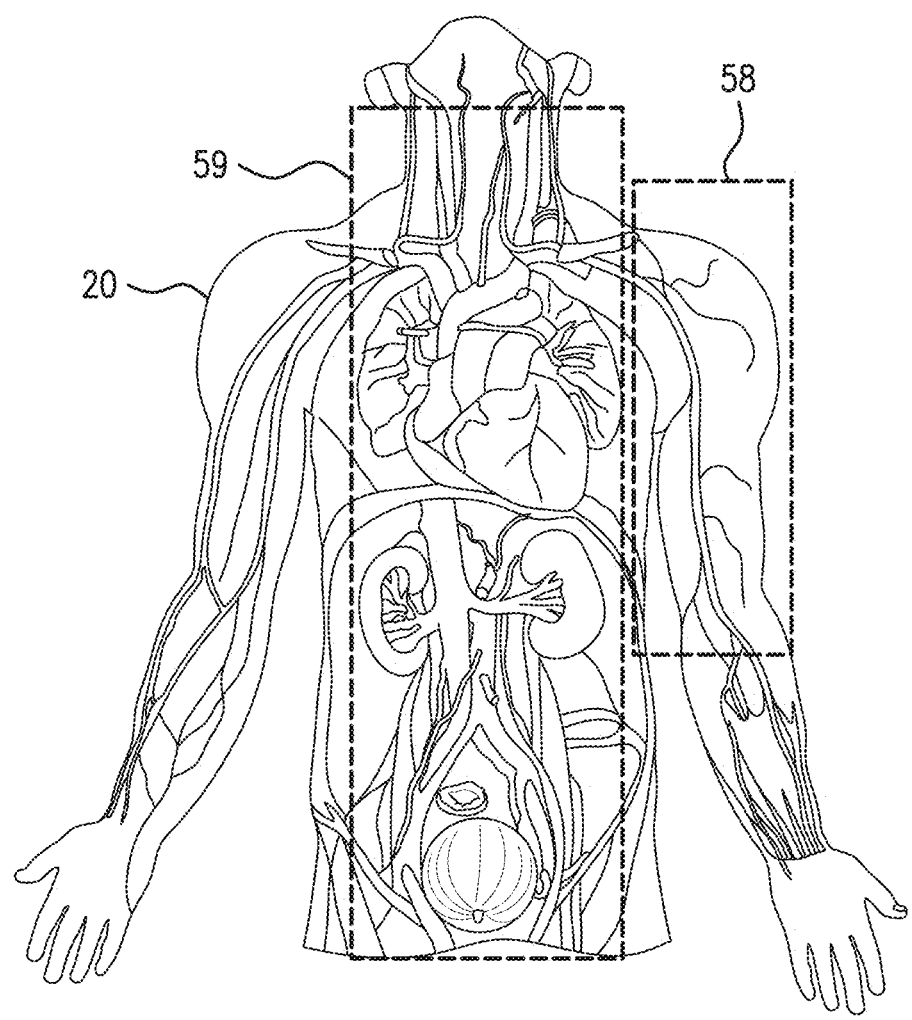
FIG. 3 shows a schematic drawing of the human body's circulatory system indicating regions where both conventional ICG and TBEV measurements are made.
Figure 4:
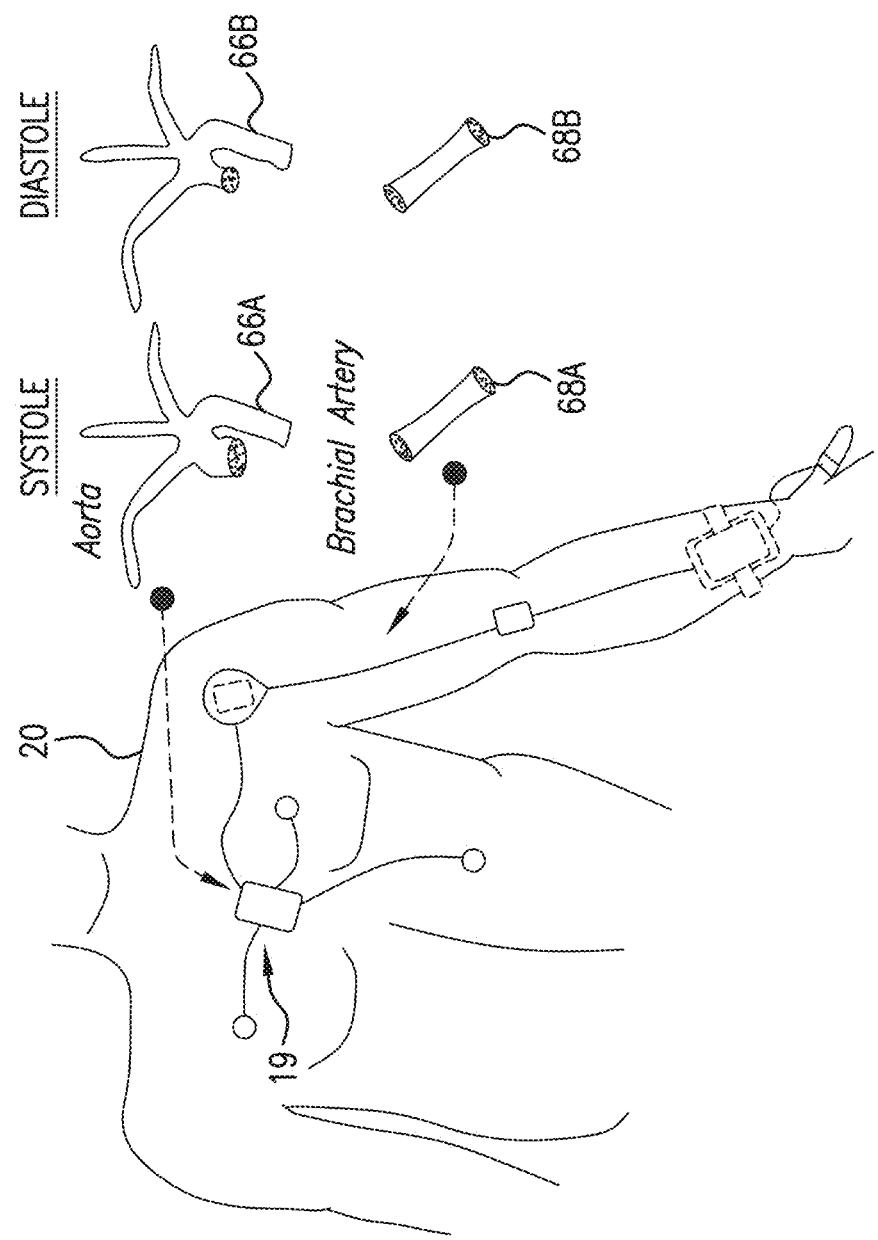
FIG. 4 shows a schematic diagram showing the body-worn monitor of the invention positioned relative to both the aorta and brachial arteries, and how these vessels change in diameter during systole and diastole.

FIGS. 3 and 4 indicate some of the advantages of TBEV measurements, which are made in the CB region 58 of the patient 20, as compared to conventional ICG measurements, which are made in the thorax 59. As is clear from FIG. 3 (with the underlying image borrowed from Gray's Anatomy), the thorax 59 features a vast and complicated collection of arteries and veins, as well as most of the patient's vital organs, such as their lungs, heart, kidneys, liver, stomach, and gastro-intestinal track. Each of these systems, and most particularly the lungs and large arteries stemming from the left side of the heart, contain conductive fluids (e.g. blood and lung fluids) that will influence conventional ICG waveforms. For example, physiological processes such as excess lung fluids, pulmonary edema, and pulmonary injury can alter the time-dependent impedance characteristics of the patient's thorax. Thus, the resulting waveforms measured therefrom are no longer reflective of the true hemodynamic state. In stark contrast is the brachium 58, which is physically removed from pulmonary affects and features only one large artery—the brachial artery—which influences the TBEV measurement. Ultimately this simplifies the morphology of the TBEV waveform and lessens its patient-to-patient variability, thereby simplifying the calculation of SV.

Importantly, previous studies have indicated a strong correlation between peak blood acceleration in the aorta, where the SV is first manifested, and peak blood acceleration in the brachium, where TBEV measures a signal used to estimate SV by square root transformation. Insofar as velocities are concerned, peak aortic blood velocity is roughly 80-124 cm/s (mean ~100 cm/s), while that in the brachial artery is roughly 30-70 cm/s (mean ~50 cm/s). Experiments that measured these parameters are described in the following references, the contents of which are incorporated herein by reference: Gardin J M et al., *Evaluation of blood flow velocity in the ascending aorta and main pulmonary artery of normal subjects by Doppler echocardiograpy*. Am. Heart J. 1984; 107:310; Wilson S et al., *Normal intracardiac and great artery blood velocity measurements by pulsed Doppler echocardiography*. Br. Heart J. 1985; 53:451; Fronek A., *Non invasive diagnostics in vascular disease*. McGraw-Hill, N.Y. 1989, pp 117; Green D, et al., *Assessment of brachial artery blood flow across the cardiac cycle: retrograde flows during bicycle ergometry*. J. Appl. Physiol 2002; 93:361. These references indicate that, to a first approximation, the average blood velocity in the aorta is roughly twice that in the brachial artery.

FIG. 4 indicates how TBEV signals are further reduced in complexity as compared to ICG signals. Without being bound to any theory, this is likely because of the relatively complex time-dependent properties of vasculature in the thorax (e.g. the aorta 66A, 66B), as compared to those in the CB region (e.g. the brachium 68A, 68B). More specifically, the figure shows the location of the body-worn monitor 19 on a patient, along with schematic drawings of the patient's aorta 66A, 66B and brachial artery 68A, 68B. During systole, the left ventricle contracts to force blood into the aorta 66A, with the volume of ejection defined as the SV. This process creates two simultaneous processes in the aorta as the cardiac cycle moves from diastole to systole: 1) a volumetric increase as the aorta's arterial walls, which are highly elastic and expand to an enlarged state 66A during systole and then recoil to a relaxed state 66B during diastole; and 2) an acceleration-induced alignment of erythrocytes within the arterial lumen, causing these cells to move from a random orientation during diastole to an aligned parallel orientation during systole. Without being bound by any theory, it is likely that both the volumetric and acceleration-induced alignment processes take place in the aorta during the cardiac cycle. Both processes affect the conductivity of blood in the aorta in a patient-specific manner, thereby complicating the pulsatile component of the ICG signal, and making it difficult for a single mathematical equation to characterize a large set of patients. Historically parameters extracted from ICG signals are fed into the well-known Sramek-Bernstein equation, shown below in Eq. 5, is based on the volumetric expansion model:

$$SV = \delta \frac{L^3}{4.25} \frac{(dZ/dt)_{max}}{Z_0} LVET \qquad (6)$$

In Eq. 5 $\delta$ represents compensation for body mass index, $Z_0$ is the base impedance, and L is estimated from the distance separating the current-injecting and voltage-measuring electrodes on the thorax. This equation and several mathematical derivatives are described in detail in the following reference, the contents of which are incorporated herein by reference: Bernstein, *Impedance cardiography: Pulsatile blood flow and the biophysical and electrodynamic basis for the stroke volume equations*; J Electr Bioimp; 1: 2-17 (2010). Eq. 5 depends on LVET, which is estimated from each pulse in the ICG waveform, as is described in more detail below. Both the Sramek-Bernstein Equation and an earlier derivative of this, called the Kubicek Equation, feature a 'static component', $Z_0$, and a 'dynamic component', $\Delta Z(t)$, which relates to LVET and a $(dZ/dt)_{max}/Z_o$ value, calculated from the derivative of the raw ICG signal, $\Delta Z(t)$. These equations assume that $(dZ/dt)_{max}/Z_o$ represents a radial velocity (with units of $\Omega/s$) of blood due to volume expansion of the aorta.

In contrast to the aorta, the brachial artery is a relatively muscular vessel that undergoes little expansion during systole 68A and recoil during diastole 68B; its arterial volume, as shown in FIG. 4, thus remains relatively constant during the cardiac cycle. Time-dependent changes in the arterial waveform are thus due nearly exclusively to periodic, sinusoidal, heartbeat-induced parallel alignment of the erythrocytes within the artery. Ultimately this means that, to develop an underlying mathematical model for the brachial artery, it is not necessary to estimate the relative contributions of volumetric expansion and erythrocyte alignment, which as described above may vary with each patient.

Sensor Configurations

Referring to FIGS. 5 and 6, in a preferred embodiment the body-worn monitor 19 is distributed on a patient 20 to measure SV/CO/CP. The monitor features a TBEV module 22, worn near the CB region, which is attached to the patient 20 using a first two-part electrode 24 shown in FIG. 2. A second two-part electrode 28 attaches to the patient 20 near the elbow. As described above, the outer conductive area in the first two-part electrode injects a high-frequency, low-amperage current into the patient's CB region, while the outer conductive area in the second two-part electrode serves as a sink for this current. Simultaneously, the inner electrodes measure a voltage that describes resistance encountered by the propagating current according to Ohm's Law. Each electrode in the first two-part electrode 24 features a rivet or post that snaps into a mated female component in the TBEV module, thereby connecting these components directly to analog circuitry therein. Similarly, electrodes in the second two-part electrode 28 connect to snaps embedded in a cable 26 that connects the first 24 and second 28 electrodes. The cable 26 includes conductors for transmitting digital data through the control area network (CAN) protocol. Use of this protocol is described in detailed in the following patent application, the contents of which have been previously incorporated herein by reference: BODY-WORN VITAL SIGN MONITOR, U.S. Ser. No. 12/560,077, filed Sep. 15, 2009. The cable 26 additionally includes conductors for transmitting analog signals to the TBEV module 22 to measure the above-described voltage. An analog-to-digital converter (not shown in the figure) within the module digitizes the TBEV waveforms to form $\Delta Z(t)$ and $Z_o$, which are then analyzed with a microprocessor (also not shown in the figure) as described above to determine a value for SV.

An ECG module 40 worn on the patient's thorax connects to the TBEV module 22 through a similar cable 27 that only includes conductors for transmitting digital signals according to the CAN protocol. The ECG module 40 connects to a trio of disposable ECG electrodes 42A-C, disposed on the patient's thorax in a conventional 'Einthoven's triangle' configuration, through a corresponding trio of ECG leads 44A-C. During a measurement, the ECG module 40 measures analog signals from each electrode 42A-C and lead 44A-C, and performs a differential amplification of these signals according to known techniques in the art to generate an ECG waveform. An analog-to-digital converter (not shown in the figure) digitizes the ECG waveform, and a microprocessor (also not shown in the figure) analyzes the well-known QRS complex within this waveform with a beat-picking algorithm to determine a HR value. Digital representations of these data are sent within CAN-formatted packets through the cable 27 to a CAN transceiver (not shown in the figure) within the TBEV module 22. There, the packets are combined with corresponding packets that include the TBEV waveform and SV values, which are calculated as described above. These packets pass through CAN conductors in the cable 26, past the second two-part electrode 28, and then through a third cable 29 to a wrist-worn transceiver 30 that connects to the patient's wrist using a plastic cradle 32 and Velcro strap 34. These components are described in more detail in the following co-pending patent applications, the contents of which have been previously incorporated by reference: BODY-WORN VITAL SIGN MONITOR, U.S. Ser. No. 12/560,077, filed Sep. 15, 2009; and BODY-WORN VITAL SIGN MONITOR, U.S. Ser. No. 12/762,726, filed Apr. 19, 2009. The wrist-worn transceiver 30 additionally connects through a short cable 38 that carries only analog signals measured by a thumb-worn optical sensor 36. Within the wrist-worn transceiver is a pulse oximetry circuit (not shown in the figure) that converts signals measured by the optical sensor 36 to generate PPG waveforms and corresponding values of SpO2. A microprocessor within the wrist-worn transceiver 30 processes PPG and ECG waveforms to generate a value of PAT, or alternatively TBEV and PPG waveforms to generate a value of VTT. These transit times are converted into cNIBP values using the Composite Method, as described above. The cNIBP values, in turn, are converted into SV estimators using the algorithm shown in FIG. 1. From there, corresponding values of CO are determined using SV and ECG-determined values of HR, while values of CP are determined using MAP and CO.

Technically, TBEV-based measurements of SV only require an isolated TBEV waveform, and can be performed without an ECG waveform. However, this signal, which is relatively easy to measure and denotes the beginning of the cardiac cycle associated with each heartbeat, can be used to 'gate' the relatively weak TBEV signal to make it easier to extract the properties described above in Eq. 3. More specifically, the above-described software beat picker can detect the QRS complex within the ECG waveform, which is associated with the onset of an individual heartbeat. Relevant portions of the TBEV waveform typically follow the QRS complex by a few hundred milliseconds. Analysis of these portions of the TBEV waveforms yields properties such as SFT, $(dZ/dt)_{max}$, and Zo that are used to calculate SV as described above. Gating the TBEV waveform in this manner can be particularly effective in analyzing these properties when noise is present in the TBEV waveform, e.g. during periods of motion.

HR, determined from the ECG waveform, is used to convert SV into CO and CO into CP, as described in Eqs. 1 and 2, above. Typically HR is determined from the time period separating neighboring QRS complexes in the ECG waveform; alternatively it can be estimated from neighboring pulses in either the PPG or TBEV waveform.

The ECG module 40 can additionally connect to 5 leads, and alternatively 12 leads. It is typically hard-wired into the TBEV module 22. The third cable 29 plugs into the wrist-worn transceiver 30 using a detachable connector 31 that allows it to be easily removed. In other embodiments the order of the ECG module 40 and TBEV module 22 can be reversed so that the TBEV module 22 is closer to the thorax, and the ECG module 40 is closer to the CB region. In still other embodiments, the TBEV module 22 can be disposed on the third cable 29 and attach directly to the second electrode 28, and the ECG module 40 can be disposed in the original location of the TBEV module 22, and be encapsulated by a housing that attaches to the first electrode 24 and feeds analog signals into the TBEV module 22. In general, multiple configurations of the various modules, cables, and electrodes shown in FIG. 6 are within the scope of the invention.

An alternate embodiment of the invention is shown in FIGS. 6A, B. Here, the ECG module 40 is worn on the patient's CB region, and the TBEV module 22 is worn near the elbow. Both the ECG 40 and TBEV 22 modules are attached to the patient with two-part electrodes 24, 28, with the TBEV electrode 24 shown in more detail in FIG. 6B. The two-part electrode 24 features a pair of female snaps 62A, B disposed on a flexible substrate 64 that connects to underlying conductive regions 63A, B. Each conductive region 63A, B features a solid gel material, chosen to match the electrical impedance characteristics of human skin, deposited on a thin Ag/AgCl film. The flexible substrate 64 features an underlying adhesive layer that during use securely attaches the electrode 24 to the patient's CB region. The female snaps 62A, B are chosen to geometrically match a pair of metal rivets 61A, B that attach to a bottom portion of a TBEV circuit board 60. During use the rivets 61A, B snap into the female snaps 62A, B, thus securing the TBEV module 22 to the patient. The rivet 61B furthest away from the CB region connects to the TBEV circuit and injects a current through the corresponding conducting region 63B, while the rivet 61A closest to the region measures a corresponding voltage. A plastic housing 65 covers the TBEV circuit board 60 and shields it from liquids and other materials present in the hospital. Note that in the figure the female snaps 62A, B are disposed on the electrode 28, and the metal rivets 61A, B are disposed on the circuit board 60. However in an alternate embodiment these components can be reversed, i.e. the female snaps 62A, B can be disposed on the bottom of the circuit board and the metal rivets 61A, B can be disposed on the top of the electrode 28.

The ECG module 40 is attached to a second electrode 24 with a geometry similar to that shown in FIG. 6B. Here, however, the electrode 24 is not electrically connected to an internal ECG circuit, but rather is used exclusively to hold the ECG module 40 in place. The electrode's conductive regions connect through electrical leads within the module 40 that are not connected to the ECG circuit, and then through a cable 68 to the TBEV module 22. There, the module 22 receives and collectively processes signals from the first 28 and second 24 electrode to measure a time-dependent voltage as described above. This voltage is then converted into a time-dependent resistance to form the TBEV waveform, which is then processed to determine SV and ultimately CO. The cable 68 also includes conductors for sending packets containing digitized ECG waveforms and HR according to the CAN protocol. These packets pass through CAN transceivers in the TBEV module 22, through the third cable 29, and ultimately to the wrist-worn transceiver 30 for further processing and display.

In FIG. 6A the individual ECG electrodes 42A-C are disposed on a single chest-worn patch 67 that attaches near the middle of the patient's thorax. The patch 67 connects to the ECG module 40 through a single cable 69 that includes individual conductors corresponding to each electrode 42A-C. These conductors port analog signals to the ECG module 40, where they are analyzed as described above to determine ECG waveforms and HR.

Within the body-worn monitor 19 are three three-axis accelerometers that measure ACC waveforms corresponding to x, y, and z-axes. The accelerometers, which are not shown in the figure, are disposed within the ECG module 40, the TBEV module 22, and the wrist-worn transceiver 30. During a measurement, ACC waveforms generated by the accelerometers are processed by microprocessors within each of the above-mentioned components to determine a motion-related parameter. Measurements of SV (or any vital sign, for that matter) are rejected if the parameter, or a secondary parameter derived therefrom, is lower than the pre-determined threshold value. Algorithms for such calculations are described, for example, in the following co-pending patent application, the contents of which are incorporated herein by reference: VITAL SIGN MONITORING SYSTEM FEATURING 3 ACCELEROMETERS, U.S. Ser. No. 12/469,094 (filed May 20, 2009).

Figure 7A:
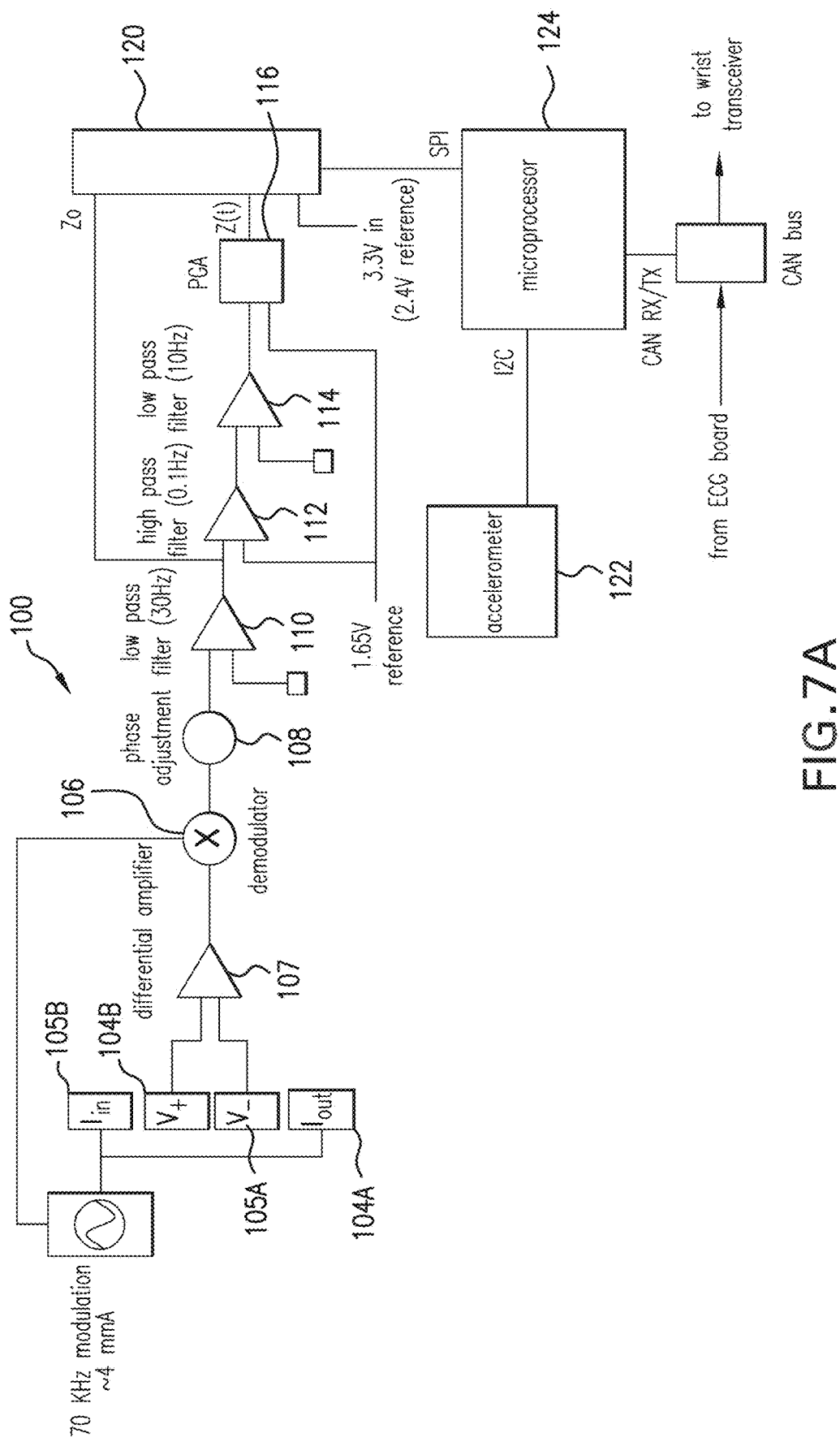
FIG. 7A shows a schematic diagram of analog and digital circuits used to make a TBEV measurement according to the invention.
Figure 7B:
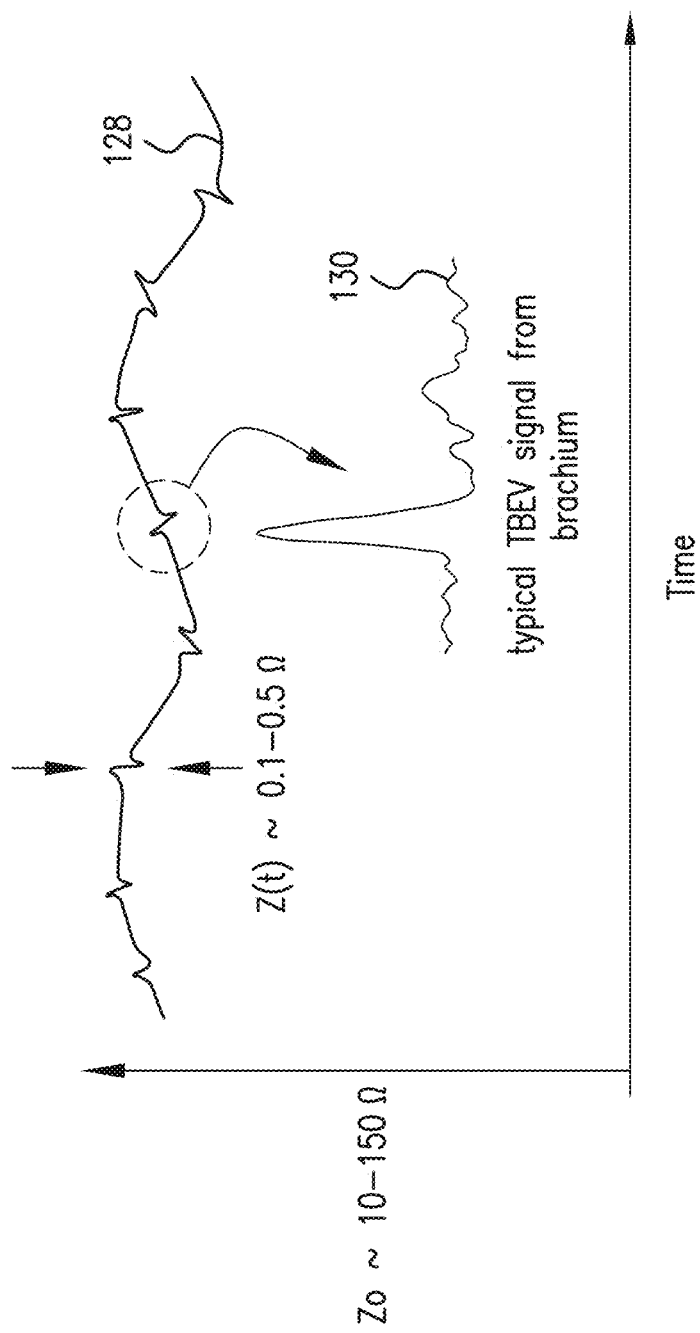
FIG. 7B shows a TBEV waveform and a highpass filtered portion thereof.

Within the TBEV module is an analog circuit 100, shown in FIG. 7, that performs the TBEV measurement according to the invention. The figure shows just one embodiment of the circuit 100; similar electrical results can be achieved using a design and collection of electrical components that differ from those shown in the figure.

The circuit 100 features a first electrode 105B that injects a high-frequency, low-amperage current ($I_{in}$) into the patient's brachium. This serves as the current source. Typically a current pump 102 provides the modulated current, with the modulation frequency typically being between 50-100 KHz, and the current magnitude being between 0.1 and 10 mA. Preferably the current pump 102 supplies current with a magnitude of 4 mA that is modulated at 70 kHz through the first electrode 105B. A second electrode 104A serves as the current drain ($I_{out}$).

A pair of electrodes 104B, 105A measure the time-dependent voltage encountered by the propagating current. These electrodes are indicated in the figure as V+ and V−. As described above, using Ohm's law (V=I×R), the measured voltage divided by the magnitude of the injected current yields a time-dependent resistance to ac (i.e. impedance) that relates to blood flow in the brachial artery. As shown by the waveform 128 in the figure, the time-dependent resistance features a slowly varying dc offset, characterized by Zo, that indicates the baseline impedance encountered by the injected current; for TBEV this will depend, for example, on the amount of fat, bone, muscle, and blood volume in the brachium of a given patient. Zo, which typically has a value between about 10 and 150Ω, is also influenced by low-frequency, time-dependent processes such as respiration. Such processes affect the inherent capacitance near the brachial region that TBEV measures, and are manifested in the waveform by low-frequency undulations, such as those shown in the waveform 128. A relatively small (typically 0.1-0.5Ω) ac component, ΔZ(t), lies on top of Zo and is attributed to changes in resistance caused by the heartbeat-induced blood that propagates in the brachial artery, as described in detail above. ΔZ(t) is processed with a high-pass filter to form a TBEV signal that features a collection of individual pulses 130 that are ultimately processed to ultimately determine stroke volume and cardiac output.

Voltage signals measured by the first electrode 104B (V+) and the second electrode 105A (V−) feed into a differential amplifier 107 to form a single, differential voltage signal which is modulated according to the modulation frequency (e.g. 70 kHz) of the current pump 102. From there, the signal flows to a demodulator 106, which also receives a carrier frequency from the current pump 102 to selectively extract signal components that only correspond to the TBEV measurement. The collective function of the differential amplifier 107 and demodulator 106 can be accomplished with many different circuits aimed at extracting weak signals, like the TBEV signal, from noise. For example, these components can be combined to form a 'lock-in amplifier' that selectively amplifies signal components occurring at a well-defined carrier frequency. Or the signal and carrier frequencies can be deconvoluted in much the same way as that used in conventional AM radio using a circuit features one or more diodes. The phase of the demodulated signal may also be adjusted with a phase-adjusting component 108 during the amplification process. In one embodiment, the ADS1298 family of chipsets marketed by Texas Instruments may be used for this application. This chipset features fully integrated analog front ends for both ECG and impedance pneumography. The latter measurement is performed with components for digital differential amplification, demodulation, and phase adjustment, such as those used for the TBEV measurement, that are integrated directly into the chipset.

Once the TBEV signal is extracted, it flows to a series of analog filters 110, 112, 114 within the circuit 100 that remove extraneous noise from the Zo and $\Delta Z(t)$ signals. The first low-pass filter 1010 (30 Hz) removes any high-frequency noise components (e.g. power line components at 60 Hz) that may corrupt the signal. Part of this signal that passes through this filter 110, which represents Zo, is ported directly to a channel in an analog-to-digital converter 120. The remaining part of the signal feeds into a high-pass filter 112 (0.1 Hz) that passes high-frequency signal components responsible for the shape of individual TBEV pulses 130. This signal then passes through a final low-pass filter 114 (10 Hz) to further remove any high-frequency noise. Finally, the filtered signal passes through a programmable gain amplifier (PGA) 116, which, using a 1.65V reference, amplifies the resultant signal with a computer-controlled gain. The amplified signal represents $\Delta Z(t)$, and is ported to a separate channel of the analog-to-digital converter 120, where it is digitized alongside of Zo. The analog-to-digital converter and PGA are integrated directly into the ADS1298 chipset described above. The chipset can simultaneously digitize waveforms such as Zo and $\Delta Z(t)$ with 24-bit resolution and sampling rates (e.g. 500 Hz) that are suitable for physiological waveforms. Thus, in theory, this one chipset can perform the function of the differential amplifier 107, demodulator 108, PGA 116, and analog-to-digital converter 120. Reliance of just a single chipset to perform these multiple functions ultimately reduces both size and power consumption of the TBEV circuit 100.

Digitized Zo and $\Delta Z(t)$ waveforms are received by a microprocessor 124 through a conventional digital interface, such as a SPI or I2C interface. Algorithms for converting the waveforms into actual measurements of SV and CO are performed by the microprocessor 124. The microprocessor 124 also receives digital motion-related waveforms from an on-board accelerometer 122, and processes these to determine parameters such as the degree/magnitude of motion, frequency of motion, posture, and activity level.

Figure 8:
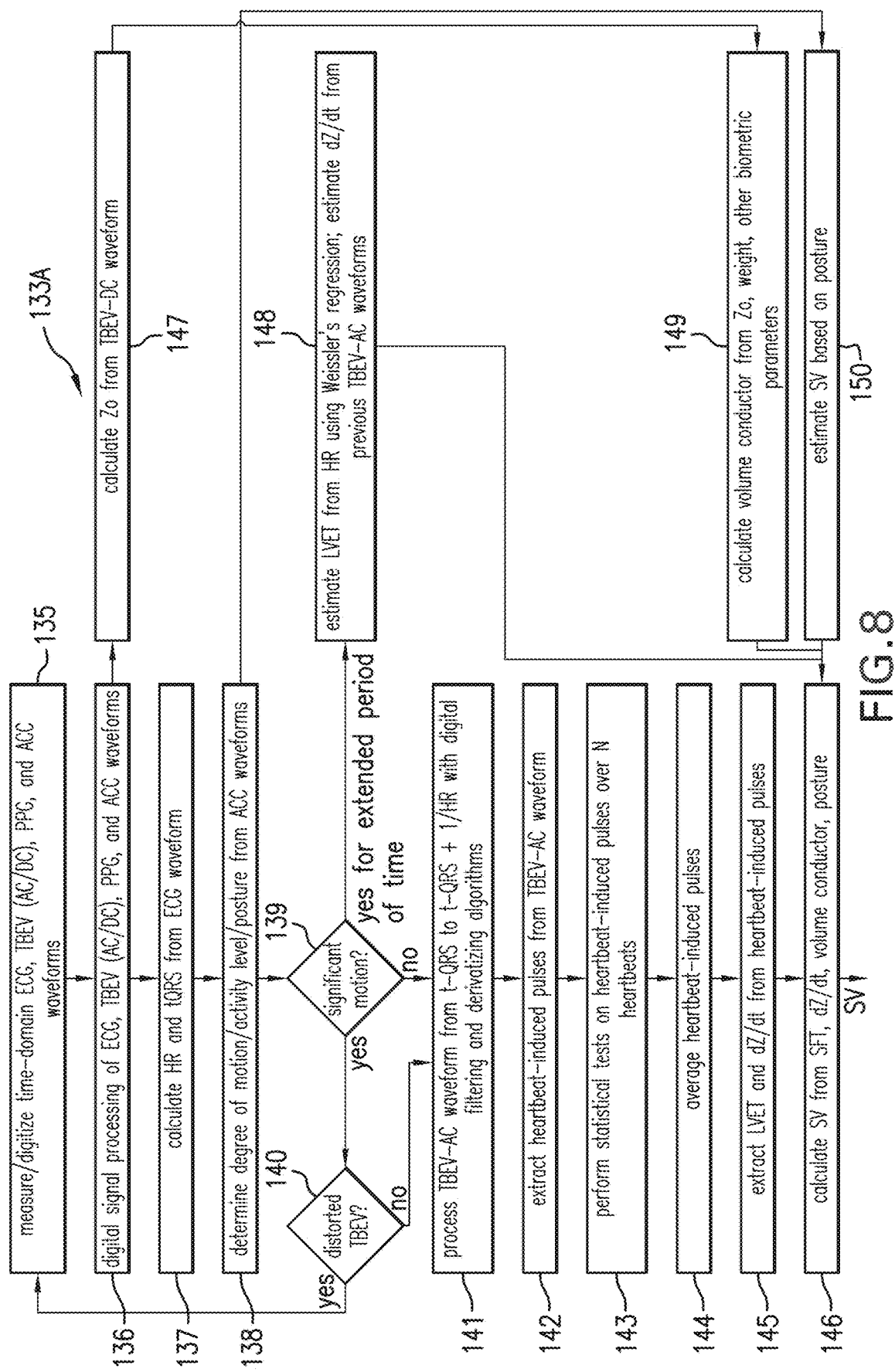
FIG. 8 shows a flow chart of an algorithm for calculating SV where systolic flow time (SFT) is determined using Weissler's regression.
Figure 9:
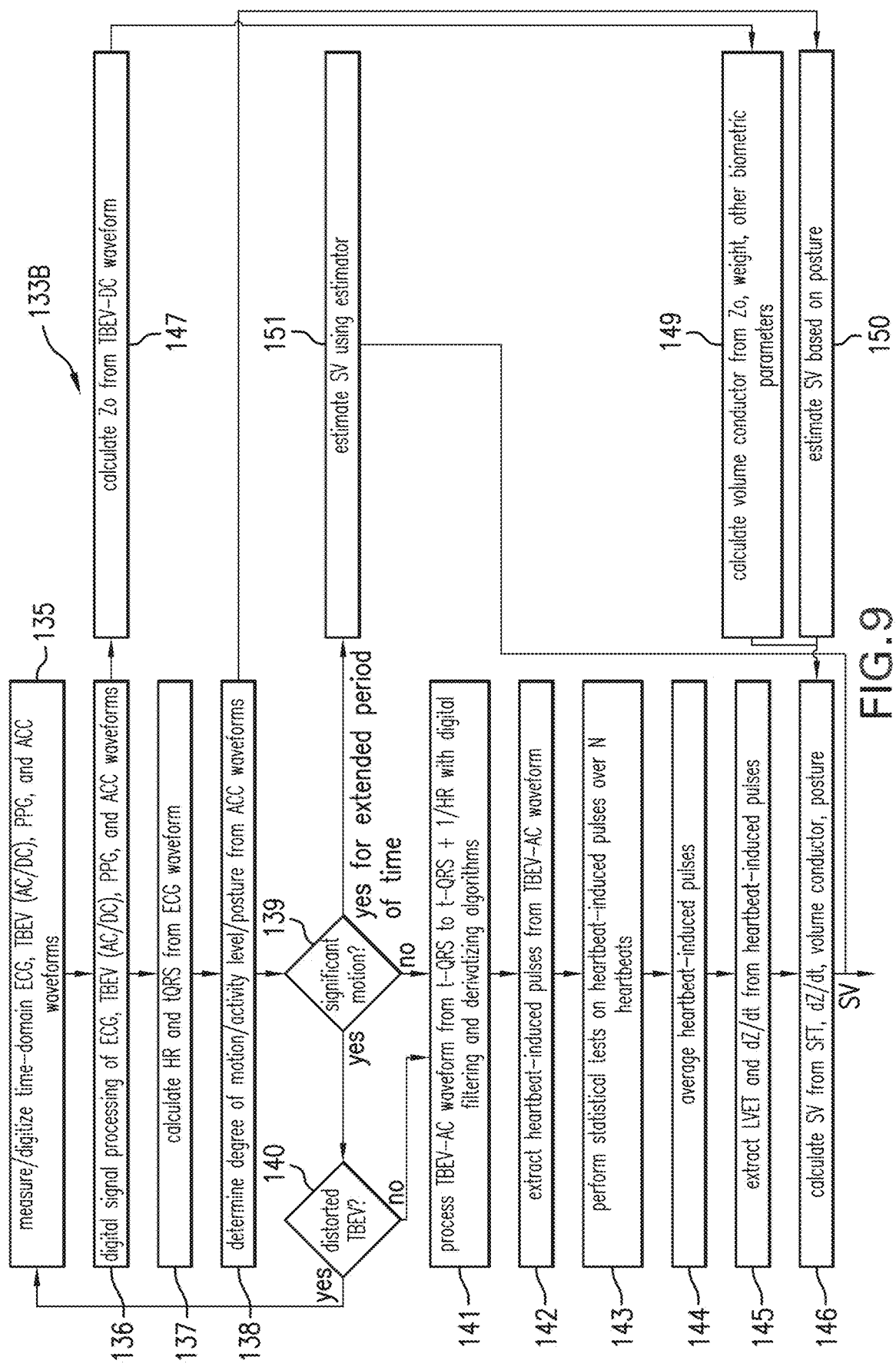
FIG. 9 shows a flow chart of an algorithm for calculating SV using the SV estimators shown in FIG. 1.

FIGS. 8 and 9 show flow charts of algorithms 133A, B that function using compiled computer code that operates, e.g., on the microprocessor 124 shown in FIG. 7. The compiled computer code is loaded in memory associated with the microprocessor, and is run each time a TBEV measurement is converted into a numerical value for CO and SV. The microprocessor typically runs an embedded real-time operating system. The compiled computer code is typically written in a language such as C, C++, or assembly language. Each step 135-151 in the different algorithms 133A, B is typically carried out by a function or calculation included in the compiled computer code.

Wrist-Worn Transceiver

Figure 10:
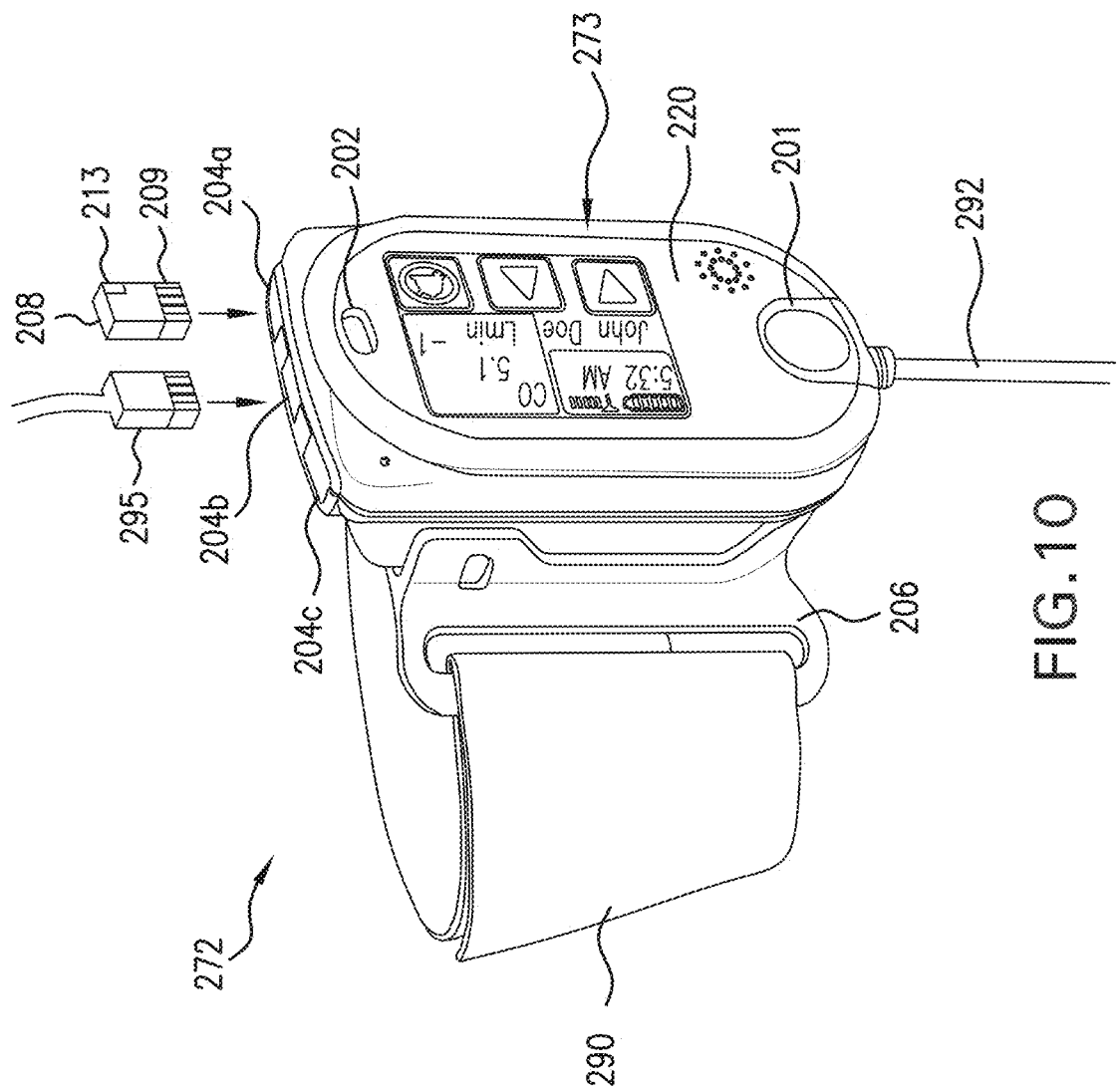
FIG. 10 shows a three-dimensional image of a wrist-worn transceiver, which is part of the body-worn monitor shown in FIGS. 5 and 6A.

The wrist-worn transceiver 272 used to perform the hybrid measurement method of SV according to the invention is shown in more detail in FIG. 10. It features an embedded microprocessor (not shown in the figure) for making these calculations, and a touch panel interface 273 that displays CO/SV along with other properties described above. A flexible wrist strap 290 affixes the transceiver 272 to the patient's wrist like a conventional wristwatch. Connected to the transceiver 272 is an analog cable 292 that terminates with an optical sensor (not shown in the figure) that wraps around the base of the patient's thumb to measure PPG waveforms. During the measurement, the optical sensor generates a series of time-dependent PPG waveforms (measured with both red and infrared wavelengths) that a microprocessor in the transceiver processes along with a TBEV and ECG to measure cNIBP, SpO2, and provide waveforms to the hybrid measurement for SV/CO/CP.

As described above, the wrist-worn transceiver attaches to the patient's wrist using a flexible strap 290 which threads through two D-ring openings in a plastic housing 206. The transceiver 272 features a touch panel display 220 that renders a GUI 273 that is altered depending on the viewer (typically the patient or a medical professional). Specifically, the transceiver 272 includes a small-scale infrared barcode scanner 202 that, during use, can scan a barcode worn on a badge of a medical professional. The barcode indicates to the transceiver's software that, for example, a nurse or doctor is viewing the user interface. In response, the GUI 273 displays vital sign data and other medical diagnostic information appropriate for medical professionals. Using this GUI 273, the nurse, doctor, or medical professional, for example, can view the vital sign information, set alarm parameters, and enter information about the patient (e.g. their demographic information, medication, or medical condition). For example, for the SV/CO/CP measurement described above, the clinician can enter the patient's gender, height, weight, and age. These parameters may be used in the calculations described in Eq. 3, above, to estimate the Vc used in Eq. 3 to calculate SV. Once entered, the clinician can press a button on the GUI 273 indicating that these operations are complete and that the appropriate data for the SV measurement has been entered. At this point, the display 220 renders an interface that is more appropriate to the patient, such as one that simply displays the time of day and battery power.

The transceiver 272 features three CAN connectors 204a-c on the side of its upper portion, each which supports the CAN protocol and wiring schematics, and relays digitized data to the transceiver's internal CPU. Digital signals that pass through the CAN connectors include a header that indicates the specific signal (e.g. TBEV, ECG, ACC, or numerical values calculated from these waveforms) and the sensor from which the signal originated. In alternative embodiments some of these are sent from the chest-worn module through Bluetooth, which maintains the CAN structure of the packets. This allows the CPU to easily interpret signals that arrive through the CAN connectors 204a-c, such as those described above corresponding to TBEB and ECG waveforms, and means that these connectors are not associated with a specific cable. Any cable connecting to the transceiver can be plugged into any connector 204a-c.

As shown in FIG. 10, one embodiment of the invention features a first connector 204a that receives a Bluetooth 'dongle' 208 that features an embedded antenna 213 and a connector 209 which snaps into and mates with any one of the CAN connectors 204a-c. During operation the dongle 208 is automatically paired with the Bluetooth transceiver in the chest-worn sensor, and then receives a digital data stream over Bluetooth with the antenna 213. An internal CAN transceiver formats the data stream into CAN-compliant packets, and then passes these through the connector 209 into the wrist-worn transceiver, where it is processed as described above.

The second CAN connector 204b receives the cable 295 that connects to another sensor, e.g. a pneumatic cuff-based system used to measure blood pressure values used in the Composite Method. This connector 204b receives a time-dependent pressure waveform delivered by the pneumatic system to the patient's arm, along with values for SYS, DIA, and MAP values determined during the Composite Method's indexing measurement. The cable 295 unplugs from the connector 204b once the indexing measurement is complete, and is plugged back in after approximately four hours for another indexing measurement.

The final CAN connector 204c can be used for an ancillary device, e.g. a glucometer, infusion pump, body-worn insulin pump, NIRS system, ventilator, or et-CO2 measurement system. As described above, digital information generated by these systems will include a header that indicates their origin so that the CPU can process them accordingly.

The transceiver 272 includes a speaker 201 that allows a medical professional to communicate with the patient using a voice over Internet protocol (VOIP). For example, using the speaker 201 the medical professional could query the patient from a central nursing station or mobile phone connected to a wireless, Internet-based network within the hospital. Or the medical professional could wear a separate transceiver similar to the shown in the figure, and use this as a communication device. In this application, the transceiver 272 worn by the patient functions much like a conventional cellular telephone or 'walkie-talkie': it can be used for voice communications with the medical professional and can additionally relay information describing the patient's vital signs and motion. The speaker can also enunciate pre-programmed messages to the patient, such as those used to calibrate the chest-worn accelerometers for a posture calculation, as described above.

Clinical Data from CO/SV Measurements

Figure 11A:
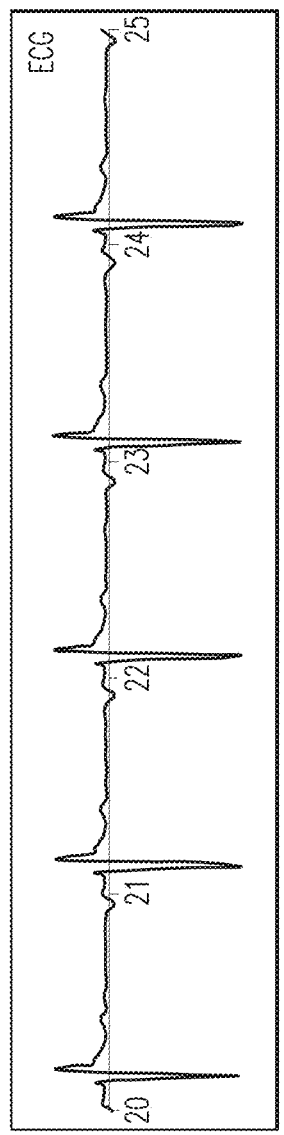
FIGS. 11A-E show time-dependent plots of, respectively, ECG, ICG, TBEV, d(ICG)/dt, and d(TBEV)/dt waveforms measured with the body-worn monitor of FIG. 5.
Figure 11B:
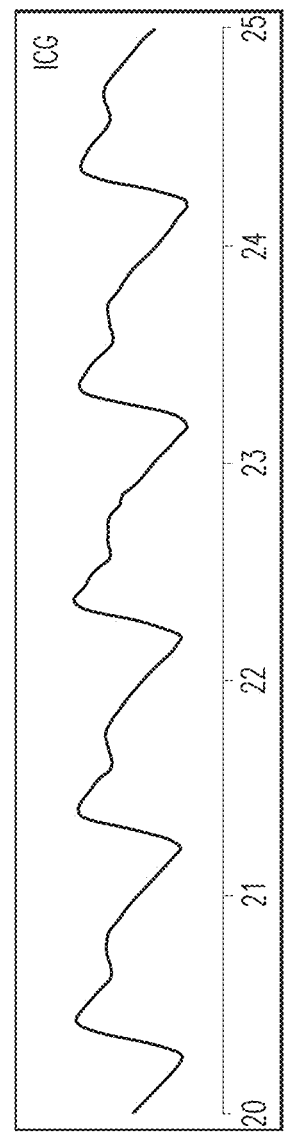
Figure 11C:
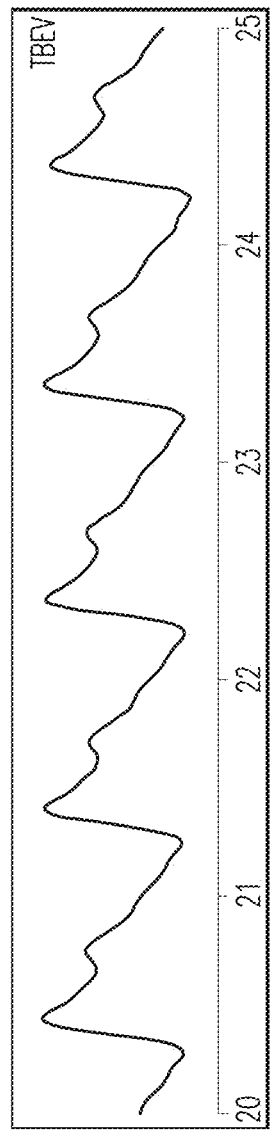
Figure 11D:
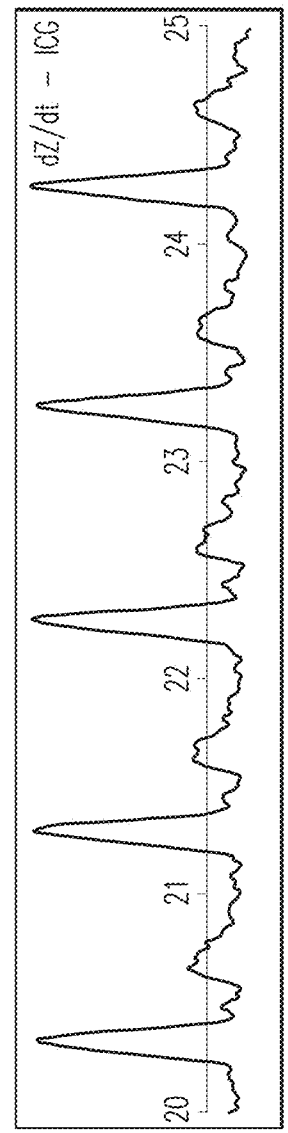
Figure 11E:
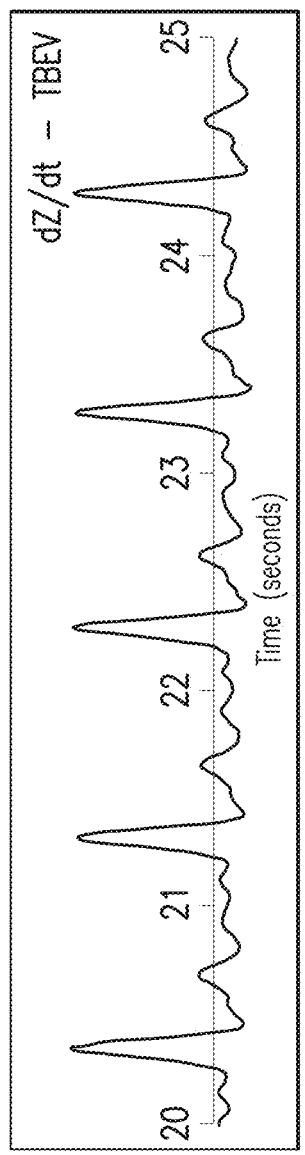

FIGS. 11A-E shows examples of ECG, ICG, and TBEV waveforms, along with time-dependent derivatives of the both ICG (d(ICG)/dt) and TBEV (d(TBEV)/dt) waveforms. These data were simultaneously measured from a human subject over a 5-second period with a body-worn monitor similar to that shown in FIG. 5. Each waveform features a heartbeat-induced 'pulse' indicating a unique physiologic process. For example, the ECG waveform shown in FIG. 11A is measured with conventional ECG electrodes and circuitry described above. It features a conventional QRS complex indicating rapid depolarization of the heart's right and left ventricles. Informally, the ECG waveform denotes the onset of the cardiac cycle. The ICG waveform (FIG. 11B) is measured from the thorax using a conventional ICG monitor and configuration of chest-worn electrodes as described above, and its derivatized form (FIG. 11D) yields parameters used above in Eq. 5 to calculate SV. Specifically, from the derivatized waveform a computer program calculates parameters such as $(dZ/dt)_{max}$ and SFT, which as described above corresponds to the time period from opening of the aortic valve, heralding the onset of ejection, to closure of the aortic valve, signifying the end of ejection. The TBEV waveform (FIG. 11C) and its time-dependent derivative (FIG. 11E) are measured from the brachium using a configuration of arm-worn electrodes similar to that shown in FIG. 5. The derivatized TBEV waveform, like the derivatized ICG waveform, yields similar impedance parameters such as $(dZ/dt)_{max}$ and SFT, and features a signal-to-noise ratio similar to that shown for the ICG waveform, despite the fact that its genesis is the much smaller brachial artery.

Figure 12A:
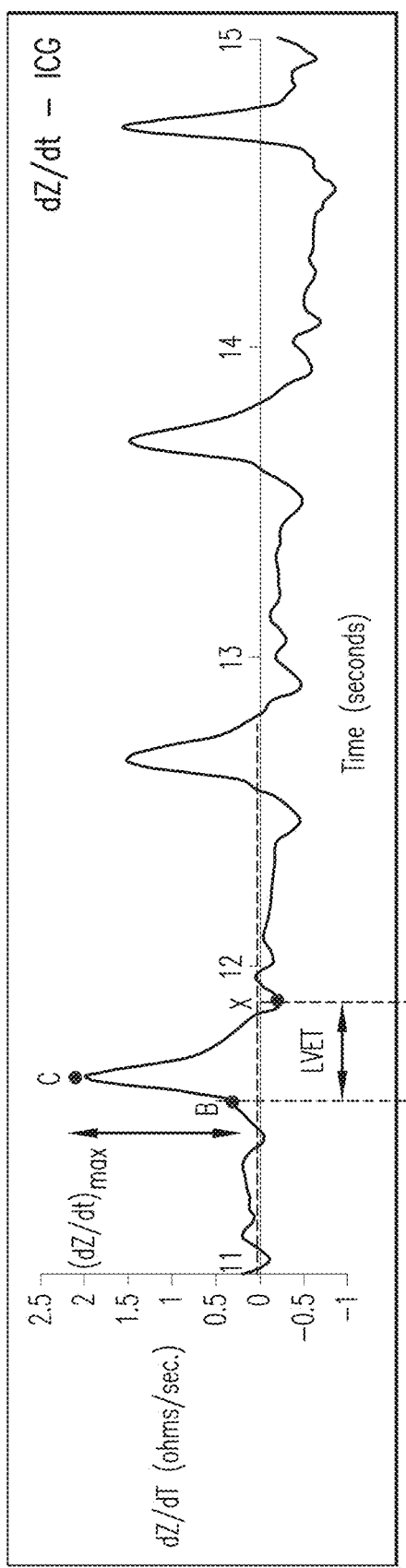
FIGS. 12A-B show time-dependent plots of dZ/dt waveform measured from, respectively, the thorax and brachium.
Figure 12B:
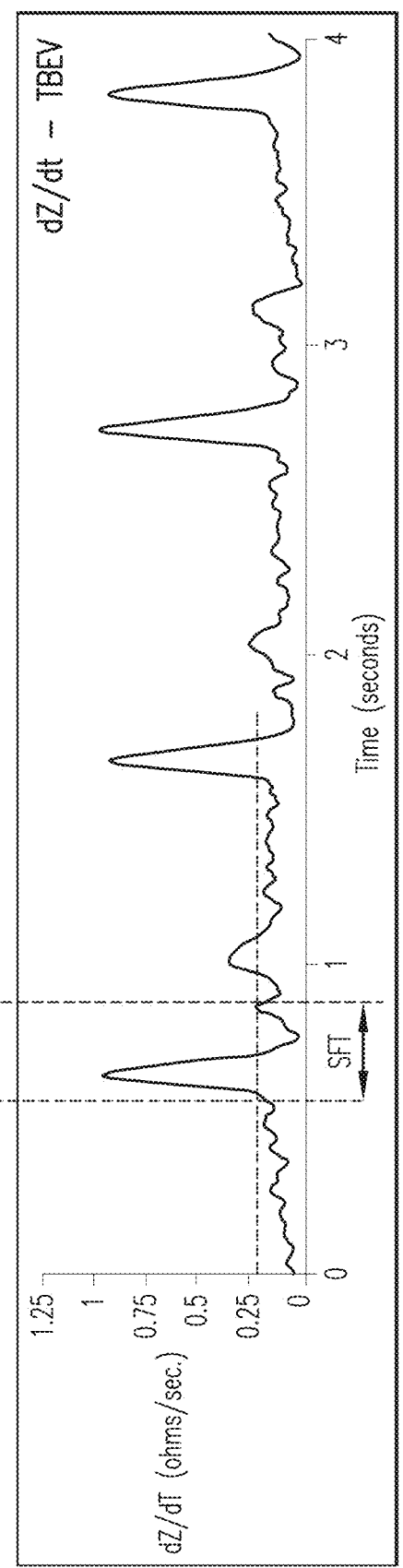

FIGS. 12A, 12B indicate how LVET and SFT are extracted, respectively, from both the derivatized ICG and TBEV waveforms. As shown in FIG. 12A, the derivatized ICG waveform features consecutive pulses, each characterized by three points: a 'B' point on the pulse's upswing indicating opening of the aortic valve; an X point on the pulse's nadir indicating closing of the aortic valve; and a 'C' point on its maximum value indicating the maximum slope of the $\Delta Z(t)$ pulse's upswing, which is equivalent to $(dZ/dt)_{max}$. LVET is typically calculated from the time differential between the B and X points. However, due to the subtle nature of these fiducial markers, even low levels of noise in the waveforms can make them difficult to determine. Ultimately such noise adds errors to the calculated LVET and resulting SV.

Determining SFT from the derivatized TBEV waveform shown in FIG. 12B is relatively easier. Here, there are no complicated B and X points. The initial upswing, or onset of the pulse, indicates the onset of flow, corresponding to opening of the aortic valve. And the second zero crossing point after $dZ/dt_{max}$, occurring later in time, indicates when acceleration of the erythrocytes is temporarily ceased. The second zero crossing indicates the end of systolic forward flow, corresponding to closing of the valve. Computationally, using a computer algorithm, such a determination of SFT can be easily done by following the progression of the pulse and recording the appropriate zero-point crossings.

FIGS. 13A-D indicate a technique for determining both an onset 90 and dichrotic notch 91, 95 in a pulse contained in a TBEV waveform. As described above, such fiducial markers can sometimes be obscured by baseline noise (caused, e.g., by motion or low signal levels), making them difficult to determine. In the derivatized waveform in FIG. 13B, a pair of data points 92 near the peak of the pulse can be selected and fit with a simple line 96, with the point at which the line 96 intersects a zero value (shown in the figure by the dashed line 90) indicating the pulse's onset. Once this point is determined, the zero-point crossing indicating the dichrotic notch can be first initially estimated using an approximation for SFT, which is the time separating the pulse's onset and dichrotic notch. This is done using an equation known as 'Weissler's Regression', shown below in Eq. 6, that estimates LVET from HR.

$$LVET = -0.0017 \times HR + 0.413 \quad (6)$$

Figure 14:
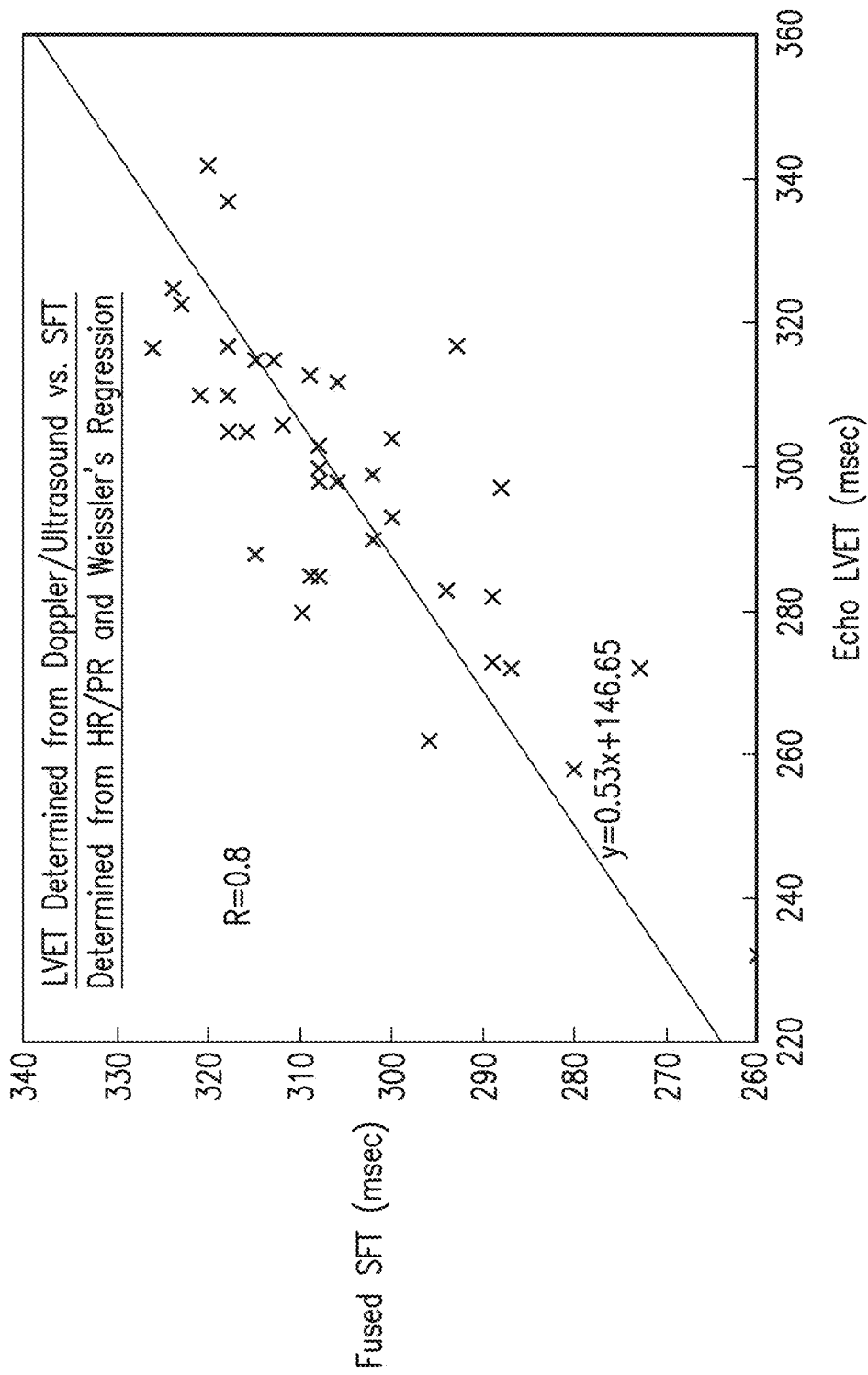
FIG. 14 shows a correlation plot comparing SFT measured using a 'fused' approach that relies partially on HR, pulse rate (PR) and Weissler's regression, and LVET measured with Doppler/ultrasound.

Weissler's Regression allows LVET, equivalent to SFT 94, 95, to be estimated from HR determined from either the ECG waveform, or alternatively from PR determined from the PPG waveform. FIG. 13C depicts a derivative of the TBEV waveform showing a shaded region 93 indicating where Weissler's regression is used to estimate LVET. LVET determined from Weissler's relationship is also shown as a vertical line in FIGS. 13A and 13D. FIG. 14 shows a correlation plot of a 'fused' SFT determined from HR and PR and compared to LVET from the Doppler/ultrasound for a 38-subject study. Here, Doppler/ultrasound represents a gold standard for determining LVET. As is clear from these data, strong correlation (r=0.8) exists between these two methods, indicating that Eq. 6 is a reasonable way to determine SFT. This method can thus be used along with parameters extracted from TBEV signals measured at the brachium to estimate SV.

Figure 15A:
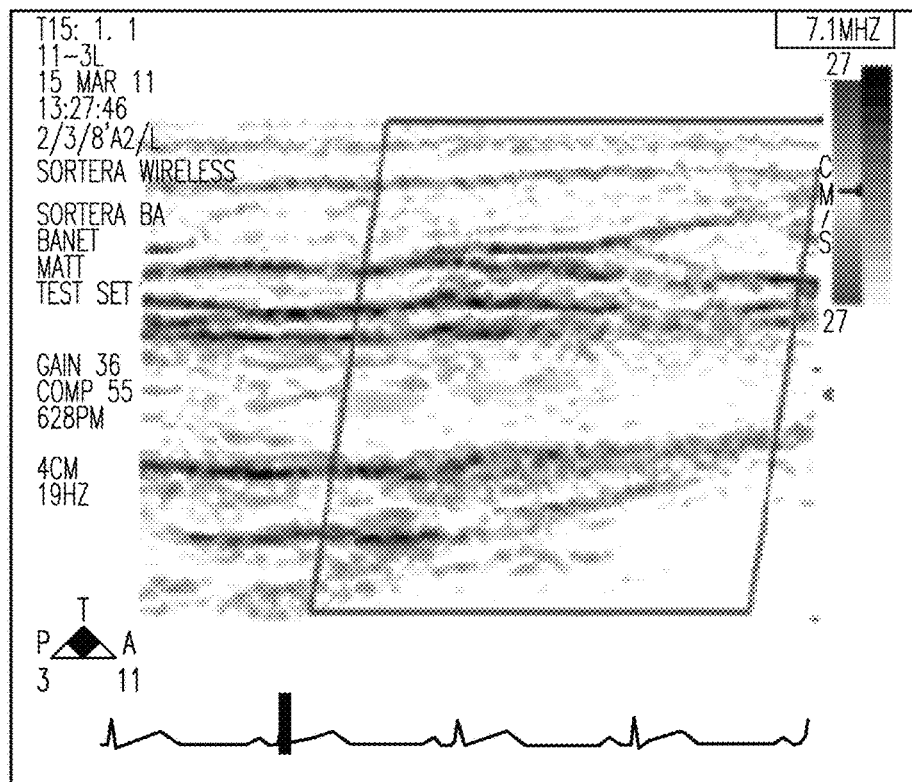
FIGS. 15A-E show two-dimensional Doppler/ultrasound images of the brachial artery measured during systole (FIGS. 15A-C), and diastole (FIGS. 15D, E)
Figure 15B:
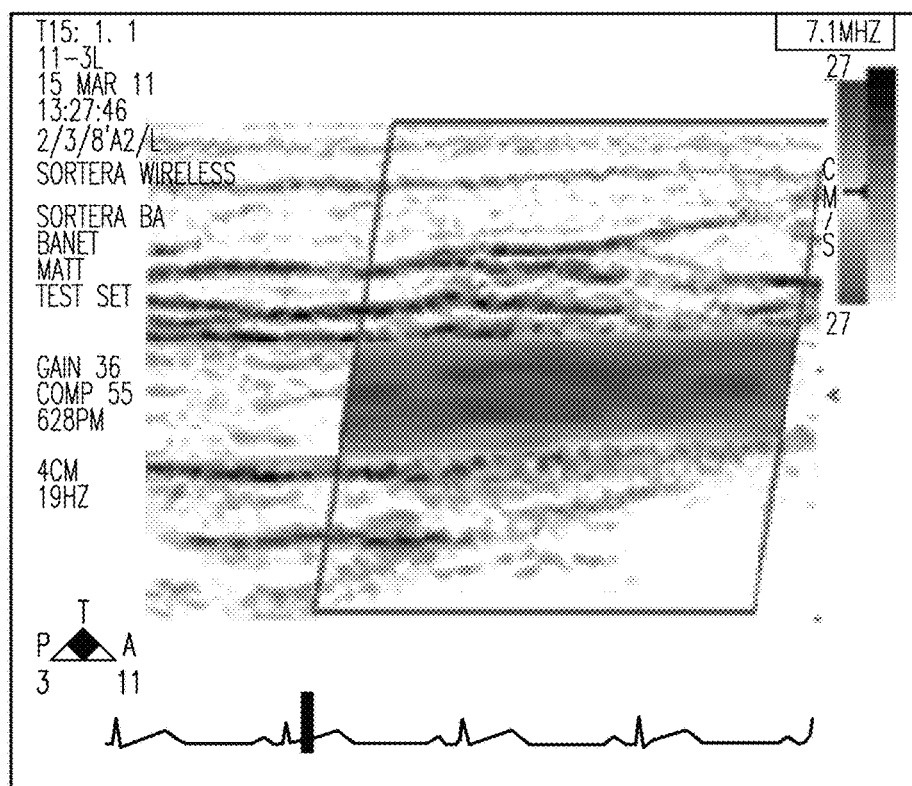
Figure 15C:
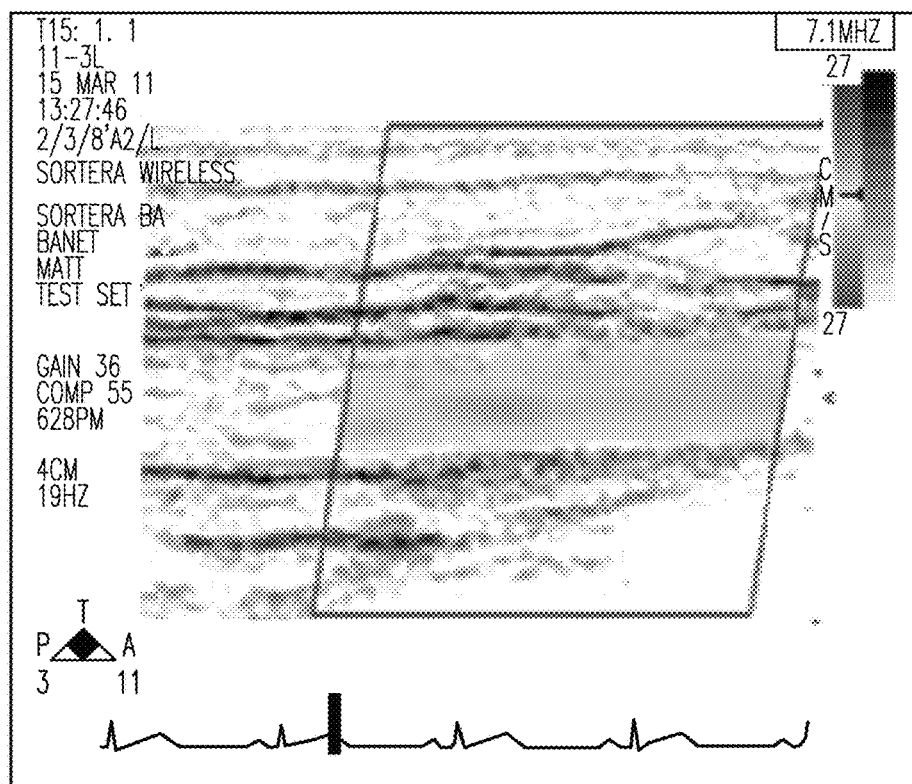
Figure 15D:
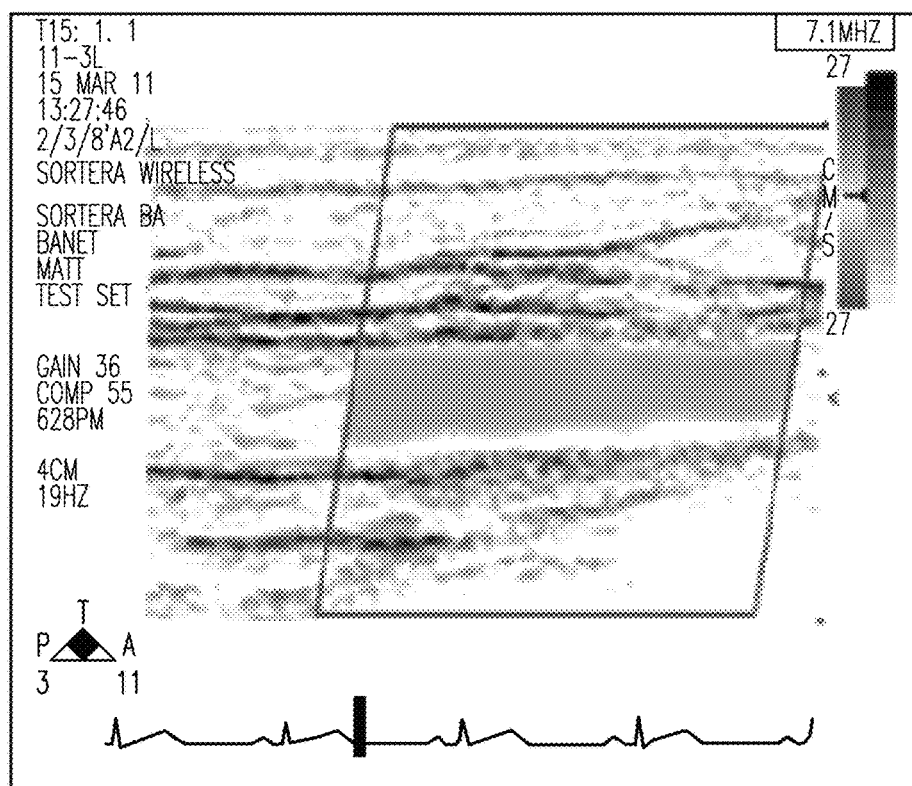
Figure 15E:
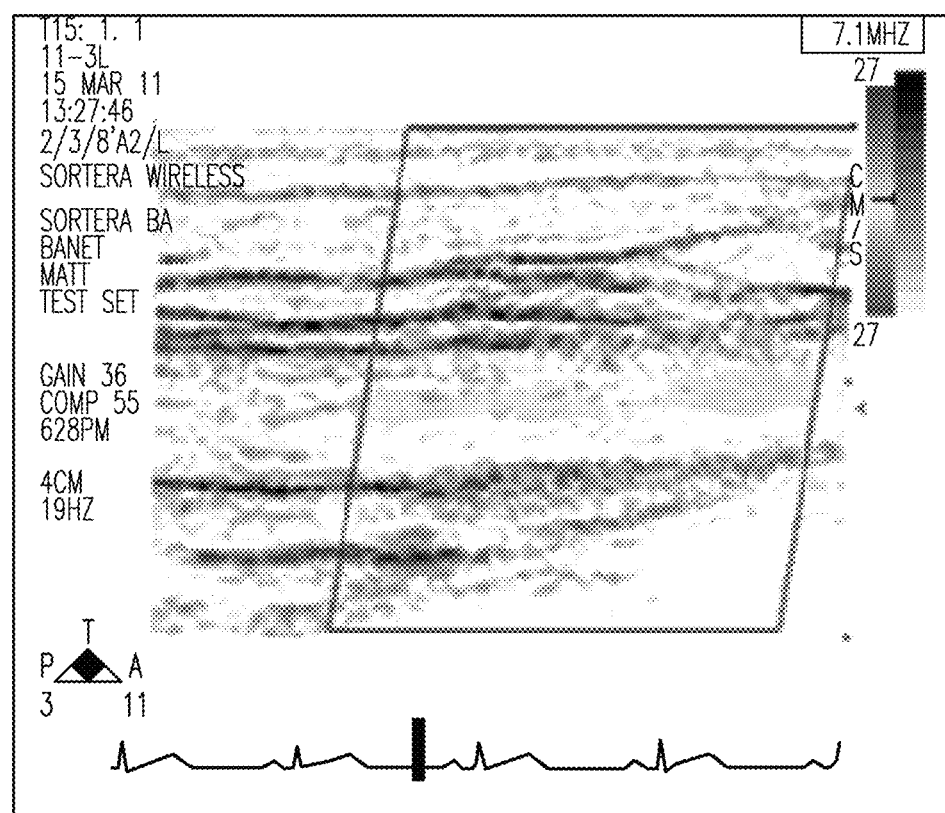
Figure 15F:
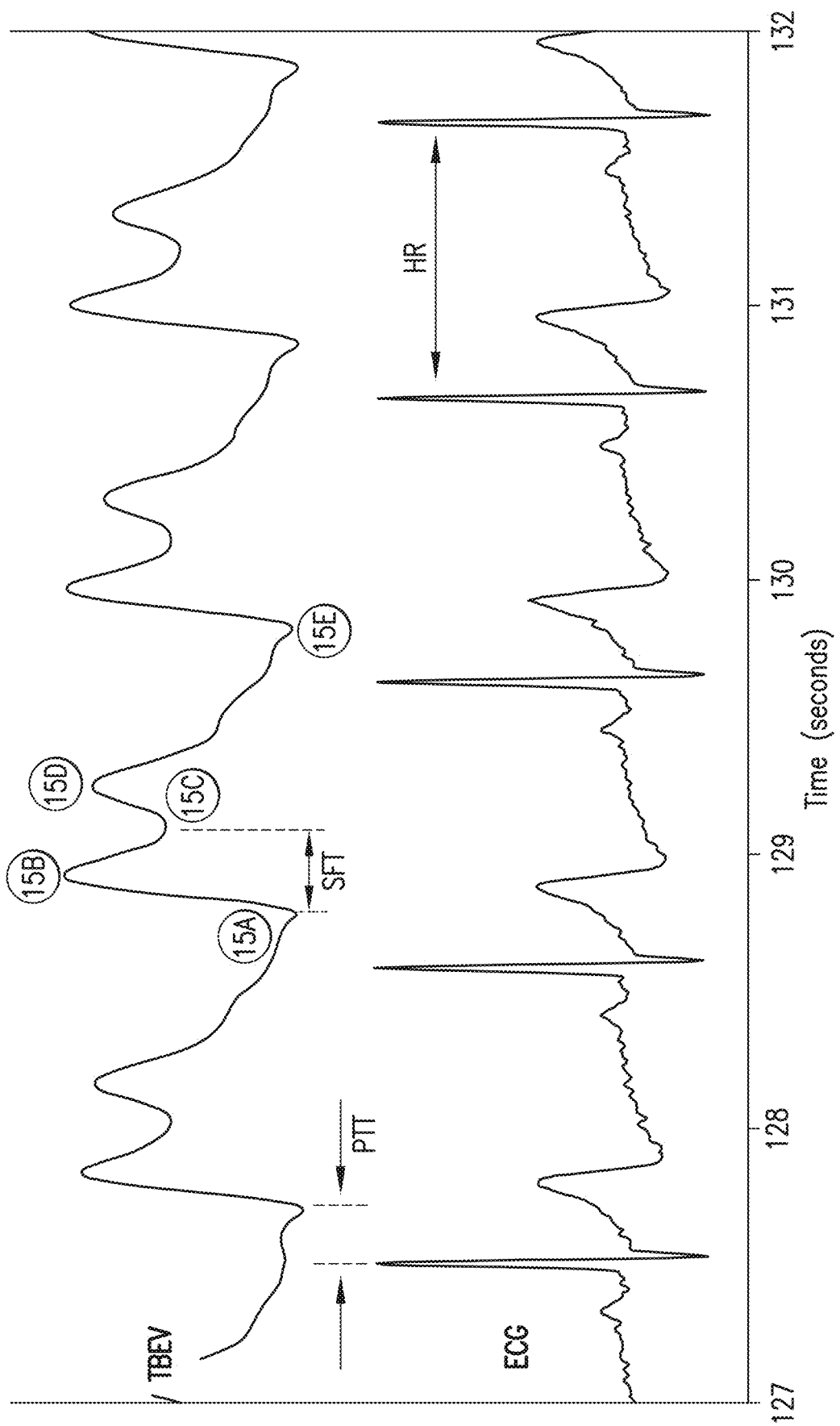
FIG. 15F shows a time-dependent plot of an ECG waveform and a TBEV waveform that corresponds to the two-dimensional images shown in FIGS. 15A-E.

To further support this point, FIGS. 15A-E show Doppler/ultrasound images measured from the brachial artery, and FIG. 15F shows concurrently measured TBEV and ECG waveforms. These data indicate two important aspects of the TBEV measurement. First, the Doppler/ultrasound images confirm that, during a typical cardiac cycle, volumetric expansion in the brachial artery is minimal. The artery's diameter undergoes little to no measurable change during the cycle, meaning that heartbeat-induced changes in blood conductivity, as measured by TBEV, are mostly due to acceleration of blood and the consequent parallel alignment of erythrocytes. Second, the images also indicate that the dichrotic notch in the TBEV waveform does indeed correspond to a point in time when the acceleration of blood is temporarily zero, and thus SFT can be accurately calculated from this fiducial marker.

More specifically, the figures show Doppler/ultrasound images indicating forward blood velocity is zero prior to systole (FIG. 15A), thereby reducing conductivity and the corresponding amplitude of the TBEV waveform. This point marks the onset of the TBEV pulse. Opening of the aortic valve induces systole (FIG. 15B) and increases acceleration of blood and thus conductivity in the brachium, causing the TBEV waveform to rapidly increase in amplitude. Closure of the aortic valve, as characterized by SFT, marks the end of the systole (FIG. 15C) a temporary lull in acceleration, and consequently the appearance of the dichrotic notch. During diastole (FIG. 15D) flow is once again increased due to reflected waves, as well as blood remaining in the aorta, which is injected into the brachium, and eventually decays away until the cycle is repeated with a new heartbeat (FIG. 15E). This relatively simple physiology contrasts the complex, underlying physiological processes that take place in the thorax as mentioned above, which are the basis for ICG-based determination of SV.

Figure 16A:
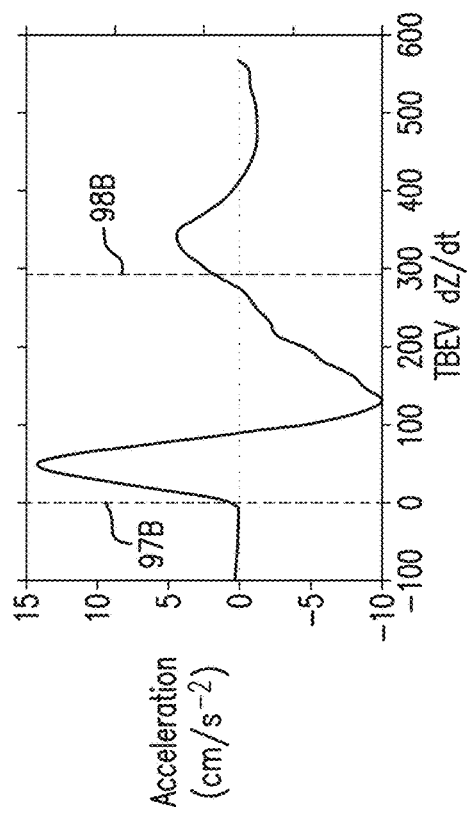
FIGS. 16A, B show time-dependent plots of, respectively, a waveform extracted from Doppler/ultrasound images taken from the brachium, similar to those shown in FIGS. 15A-E, and a simultaneously measured TBEV waveform.
Figure 16C:
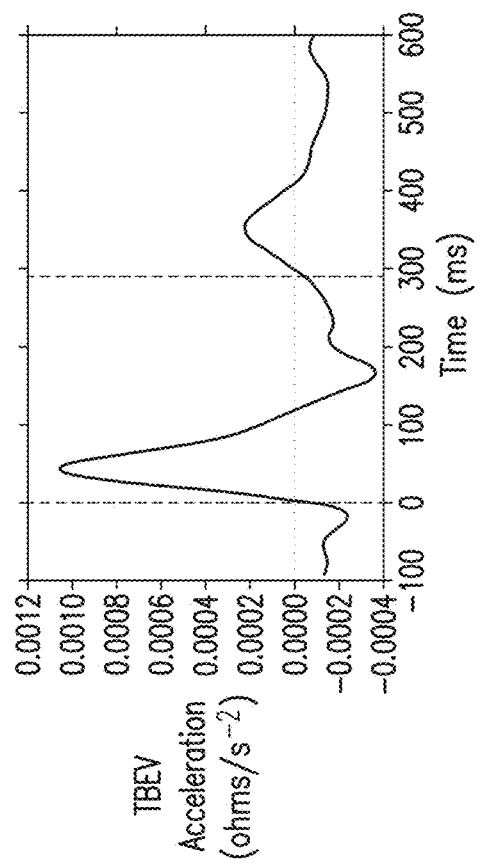
FIGS. 16C, D show plots of, respectively, the time-dependent derivatives of the waveforms shown in FIGS. 16A, B.
Figure 16B:
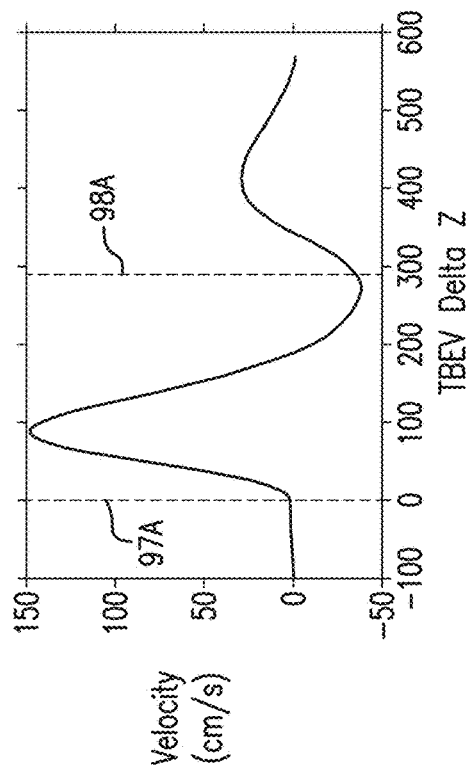
Figure 16D:
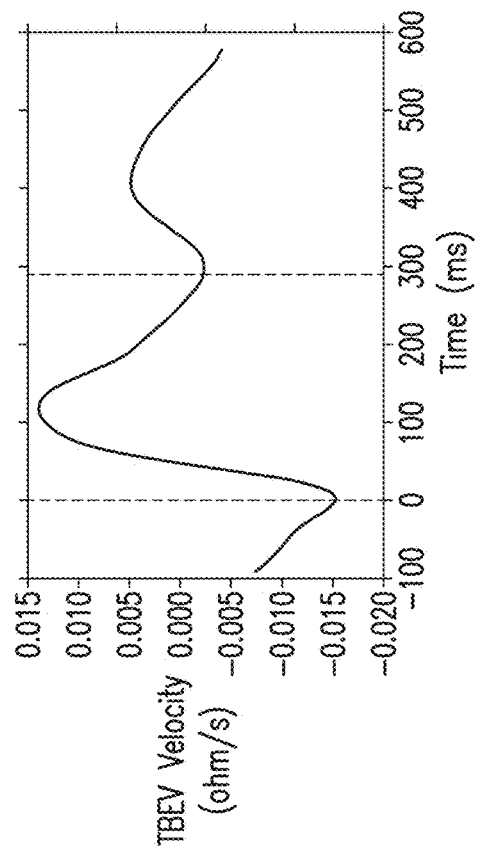

FIGS. 16A-D further illustrates how TBEV waveforms yield SFT in much the same way as Doppler/ultrasound yields LVET, which as described above represents a gold standard for this measurement. Here, FIG. 16A shows a time-dependent waveform extracted from a collection of two-dimensional Doppler/ultrasound images, such as those shown in FIGS. 15A-E. The waveform indicates time-dependent blood velocity, and its derivatized form is shown in FIG. 16C. Shown below these waveforms in FIGS. 16B and 16D are simultaneously measured TBEV waveforms (FIG. 16B) and its derivatized form (FIG. 16D). Dashed lines 97A, B, 98A, B in the figures show, respectively, the pulse onset (determined, e.g., as shown in FIG. 13) and the dichrotic notch from the two sets of waveforms. As is clear from the figure, these points coincide exactly, indicating that LVET determined explicitly from Doppler/ultrasound waveforms is nearly identical to SFT determined from TBEV waveforms.

Figure 17:
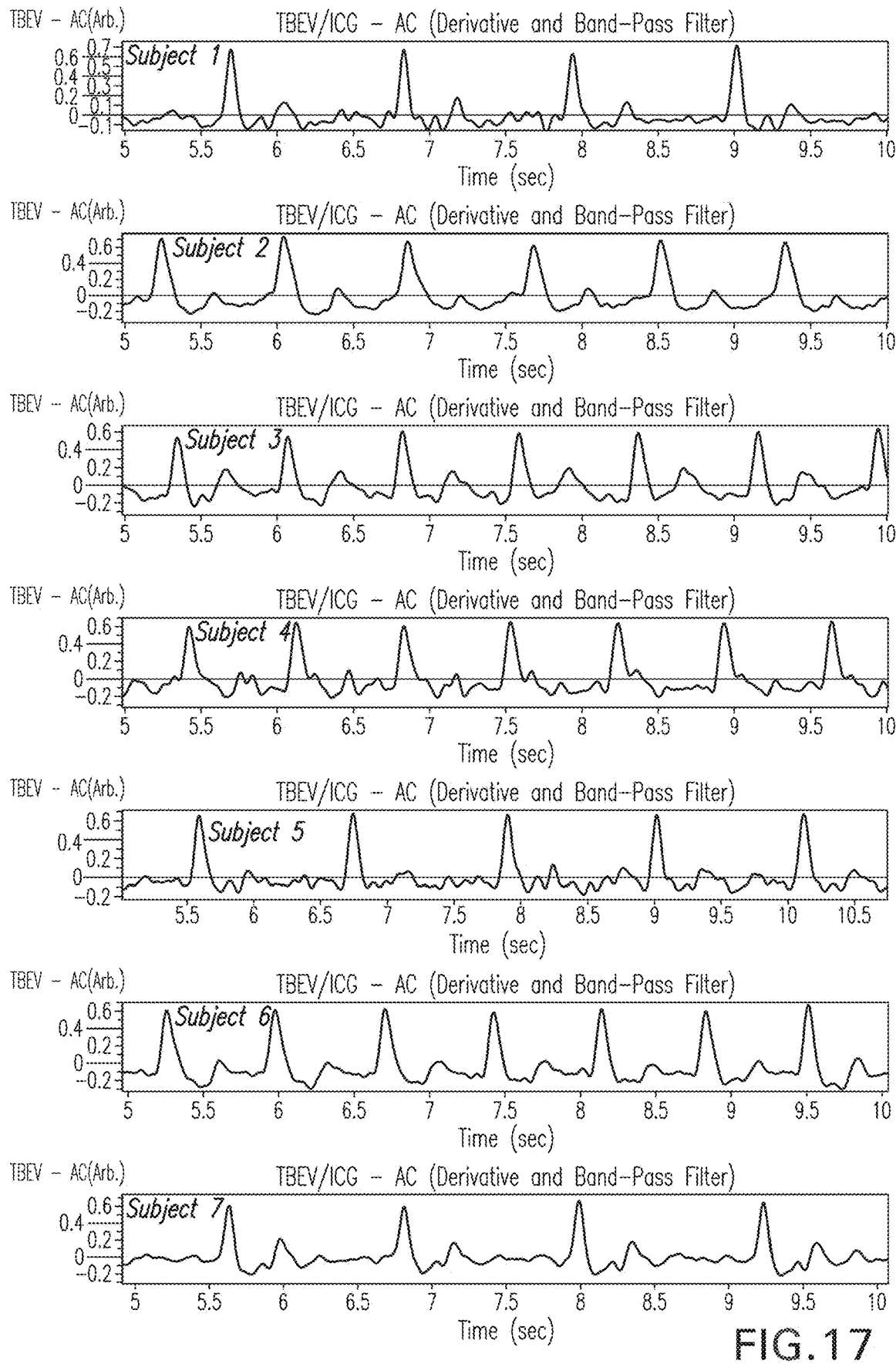
FIG. 17 shows derivatized TBEV waveforms measured from 7 unique subjects.

Another advantage of TBEV waveforms compared to those measured with conventional ICG is that they undergo little patient-to-patient variation, thus making their computer-based analysis relatively easy. FIG. 17 demonstrates this point by showing derivatized waveforms from 7 different subjects. Each waveform has roughly the same morphology, and in all cases the relevant fiducial makers (pulse onset, pulse maximum, zero-point crossing) are clear. This indicates that a simple computer algorithm can be used to extract $(dZ/dt)_{max}$ and SFT, which is then used as described above to calculate SV.

Figure 18A:
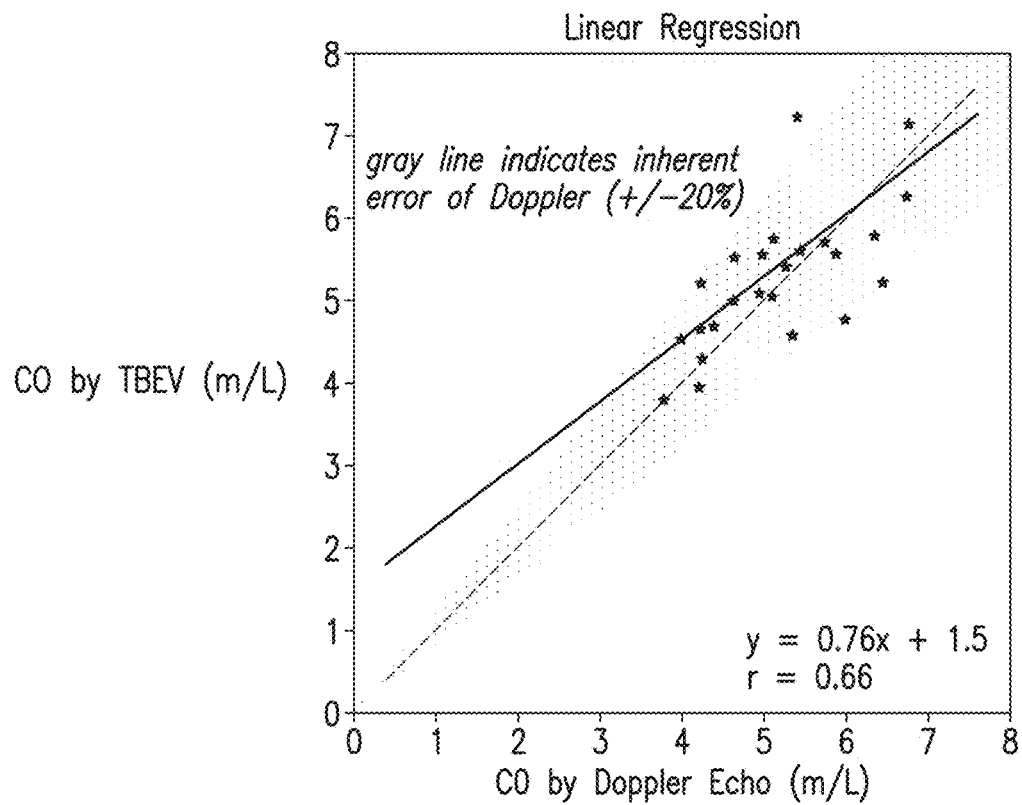
FIGS. 18A, B show, respectively, correlation and Bland-Altman plots comparing CO measured from of 23 subjects using Doppler/ultrasound and TBEV.
Figure 18B:
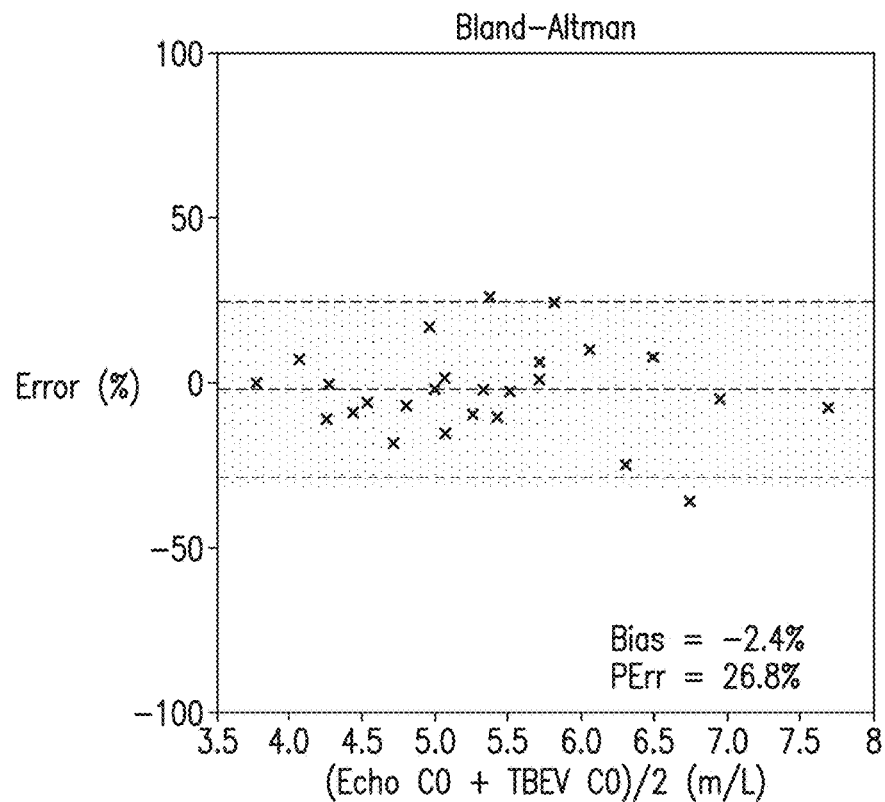

The analysis described above was used in a formal clinical study to test accuracy of determining CO using TBEV and Eq. 3 above, compared to CO determined using Doppler/ultrasound. Correlation and Bland-Altman plots are shown, respectively, in FIGS. 18A and 18B. The shaded gray area in the plots indicates the inherent errors associated with conventional Doppler/ultrasound measurements, which are about +/−20%. In total 23 subjects (11M, 12W) with ages ranging from 21-80 were measured for this study, and correlations for all but two of these subjects fell within the error of the Doppler/ultrasound measurements.

Figure 19B:
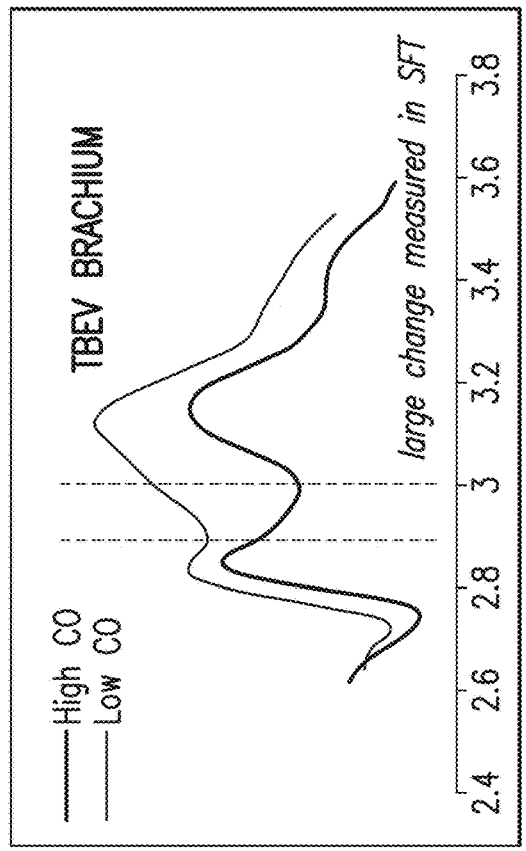
FIGS. 19A, B show time-dependent plots of, respectively, ICG and TBEV waveforms corresponding to high and low values of CO measured while a subject is wearing military anti-shock trousers (MAST)
Figure 19A:
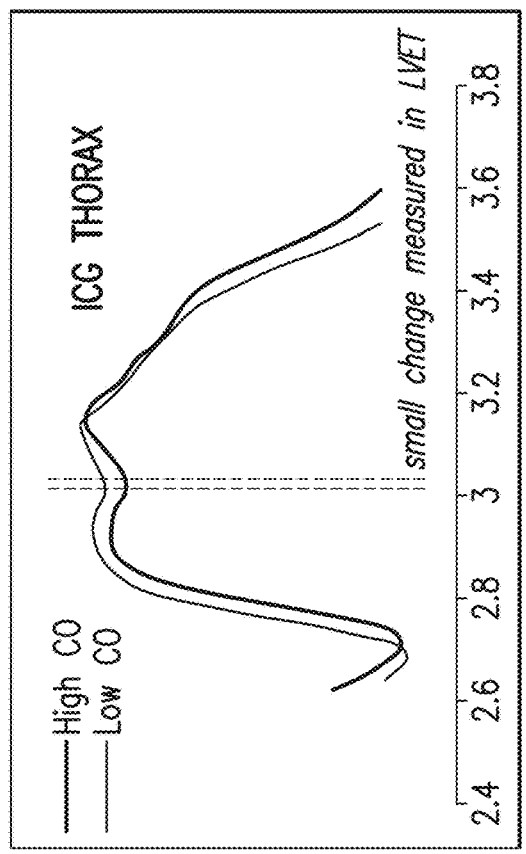

FIGS. 19A-B indicate that TBEV waveforms measured from the brachium may be a better determinant of CO than ICG waveforms measured from the thorax. Here, both waveforms were measured while a subject wore a 'MAST' suit, which is a pair of pressurized trousers used to force blood from the lower extremities toward the torso and the heart. A MAST suit thus simulates the reverse of hemorrhage, and thus causes CO/SV to increase. As shown in the figures by the dashed lines, LVET was determined from ICG, while SFT was determined using TBEV. Waveforms from these techniques were measured simultaneously from the thorax and brachium during period of high and low SV measurements. Increased SV is achieved when the MAST suit forces blood into the thorax. An increase in both LVET and SFT indicate an increase in SV. In the ICG waveforms (FIG. 19A) only a small increase in LVET was detected. In contrast, in the TBEV waveforms (FIG. 19B), a large increase in SFT was detected, indicating measurements made in this region of the body may be more sensitive to small changes in SV and CO.

Measuring Respiration Rate with TBEV

TBEV, like techniques such as impedance pneumography, injects small amounts of current into the patient's body, and measures resistance (i.e. impedance) encountered by the current to calculate a parameter of interest. During a TBEV measurement, heartbeat-induced blood flow results in the pulsatile component of $\Delta Z(t)$. Additionally, changes in capacitance due to breathing may also affect the impedance as measured by TBEV. FIGS. 20A-C illustrate this point. In FIG. 20A, for example, a TBEV waveform with no digital filtering shows both high-frequency cardiac components due to blood flow, as well as low-frequency undulations due to respiration rate. Both features can be extracted and analyzed using digital filtering. For example, as shown in FIG. 20B, processing the TBEV waveform shown in FIG. 20A with a first band-pass filter (0.5→15 Hz) removes the respiratory component, leaving only the cardiac component. Similarly, as shown in FIG. 20C, processing the TBEV waveform shown in FIG. 20A with a second band-pass filter (0.001→1 Hz) removes the cardiac component, leaving on the undulations due to respiration. In this latter case, the peaks in the waveform can be counted with a conventional breath-picking algorithm to determine respiration rate.

The algorithm for calculating respiration rate can be expanded to include processing of signal from the accelerometer within the TBEV module. For example, as shown in FIGS. 21A-D, these signals can be collectively processed to accurately determine respiration rate, even in the presence of motion. A similar technique is described in the following co-pending application, the contents of which are incorporated herein by reference: BODY-WORN MONITOR FOR MEASURING RESPIRATION RATE, U.S. Ser. No. 12/762,874, filed Apr. 14, 2010. More specifically, FIGS.

Figure 21A:
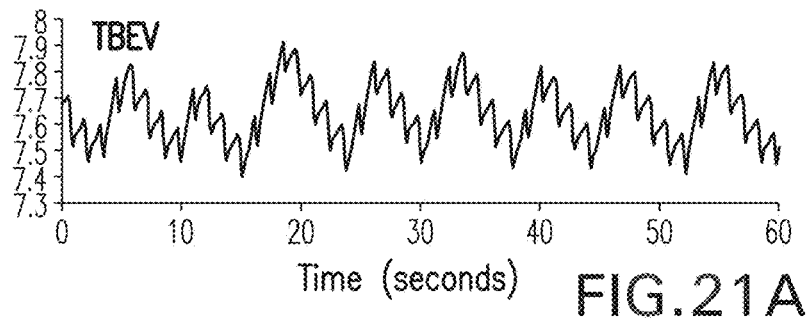
FIGS. 21A, B show time-dependent plots of, respectively, TBEV and ACC waveforms modulated by respiration events.
Figure 21B:
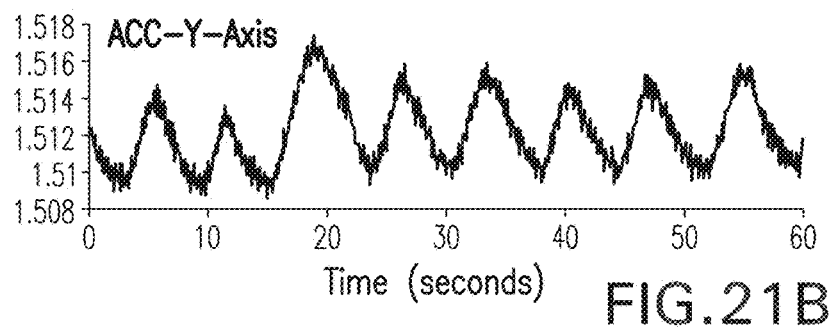
FIGS. 21C, D show frequency-domain power spectra of the time-dependent plots shown, respectively, in FIGS. 21A, B.
Figure 21C:
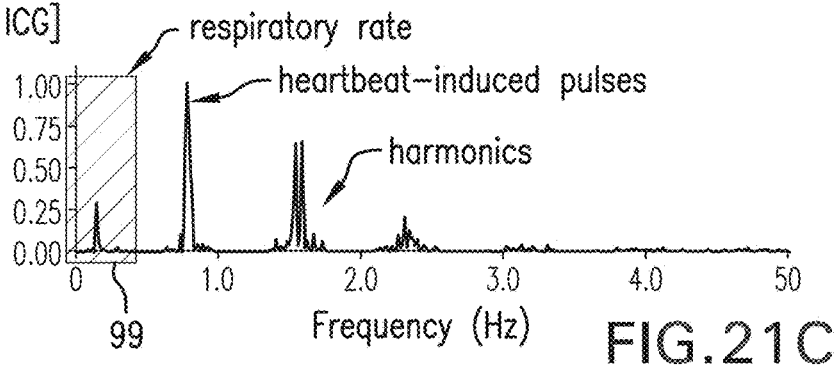
Figure 21D:
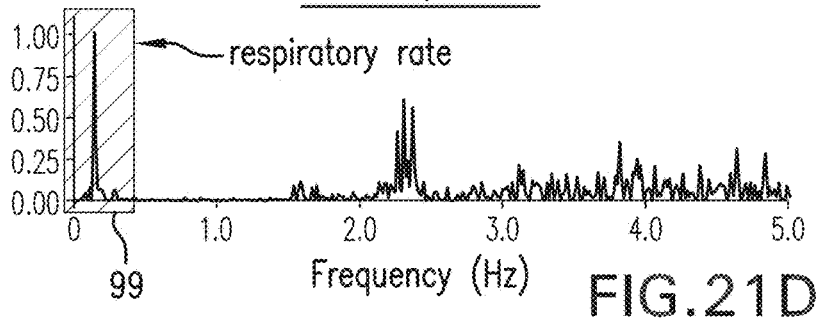

21A and 21B show time-domain TBEV and ACC waveforms measured simultaneously from a patient with the system similar to that described above. In the TBEV waveform, the slowly varying pulses occurring approximately every 7 seconds correspond to individual breaths, while the sharp peaks in the waveform correspond to heartbeat-induced pulses. FIGS. 21C and 21D show, respectively, frequency-domain power spectra of both the TBEV and ACC waveforms. Clearly shown in the power spectra of the TBEV waveform is a dominant peak near 0.8 Hz corresponding to the heartbeat-induced pulses. A much weaker peak corresponding to the patient's breathing rate is also evident near 0.15 Hz. As shown in the gray shaded region 99, the power spectra corresponding to the ACC waveform features only one well-defined peak near 1.5 Hz that includes nearly the exact same frequency components as the corresponding peak in the TBEV waveform. Further processing of these two spectra with a simple peak-finding algorithm yields the patient's actual RR, which corresponds to about 8 breaths/minute.

Measuring TBEV Waveforms in the Absence of Motion

FIGS. 22A, B and 23A, B indicate how different degrees of motion from a patient's arm can influence both ECG and TBEV waveforms, thereby affecting the accuracy of SV measurements. The ACC waveform is typically measured along the vertical axis of the accelerometer embedded in the TBEV module. The magnitude of the axes for ECG and TBEV waveforms are the same for all figures.

In FIG. 22B, for example, the ACC waveform is relatively flat and lacks any significant time-dependent features, indicating that the patient is not moving and is relatively still. Consequently the TBEV waveform in FIG. 22A, which is strongly affected by motion, features well-defined values for the pulse onset, indicated by marker 73, and $(dZ/dt)_{max}$, indicated by marker 74. Likewise the ECG waveform features a QRS complex, indicated by marker 72, which is undistorted. The fidelity of these features indicate that both HR and SV values can typically be accurately determined during periods of little or no motion, as indicated by the ACC waveform in FIG. 22B.

FIGS. 23A, B show the affects of a major amount of arm motion on both the ECG and TBEV waveforms. Here, the period of motion is indicated in both figures by the dashed box 80, which contrasts with the preceding period where motion is not present, as shown in the dashed box 81. The ACC waveform in FIG. 23B indicates that motion lasts for roughly one second, beginning and ending at times indicated, respectively, near markers 78 and 79. The motion is complex and peaks in intensity at marker 79. Even for major finger motion the ECG waveform and its QRS complex, indicated by marker 75, are relatively undistorted. But the TBEV measured during the period of motion is strongly distorted to the point that its peak value, indicated by marker 77, is relatively flat and basically immeasurable. This makes it difficult to accurately measure TBEV waveforms and the subsequent SV value calculated from this parameter. The peak onset, indicated by marker 76, is also distorted, but to a lesser degree than the corresponding peak value.

Data shown in FIGS. 22A, B and 22A, B indicate that motion can be detected and accounted for during TBEV measurements to minimize the occurrence of false alarms and, additionally, make accurate readings in the presence of motion. For example, during periods of motion SFT can be calculated using Weissler's Regression, and then used to Eq. 3 above to estimate SV. Or during such motion one of the various estimators shown in FIG. 1 could be used to estimate SV.

Processing ACC Waveforms to Determine Posture

A patient's posture may influence their values of SV/CO/CP, and thus knowing this parameter may improve the measurement described herein. To make this measurement, the body-worn monitor described above includes three 3-axis accelerometers as well as the ECG and TBEV circuits. In addition to determining SV/CO/CP, these sensors can generate time-dependent waveforms that when analyzed yield RR and the patient's motion-related properties, e.g. degree of motion, posture, and activity level.

Figure 25:
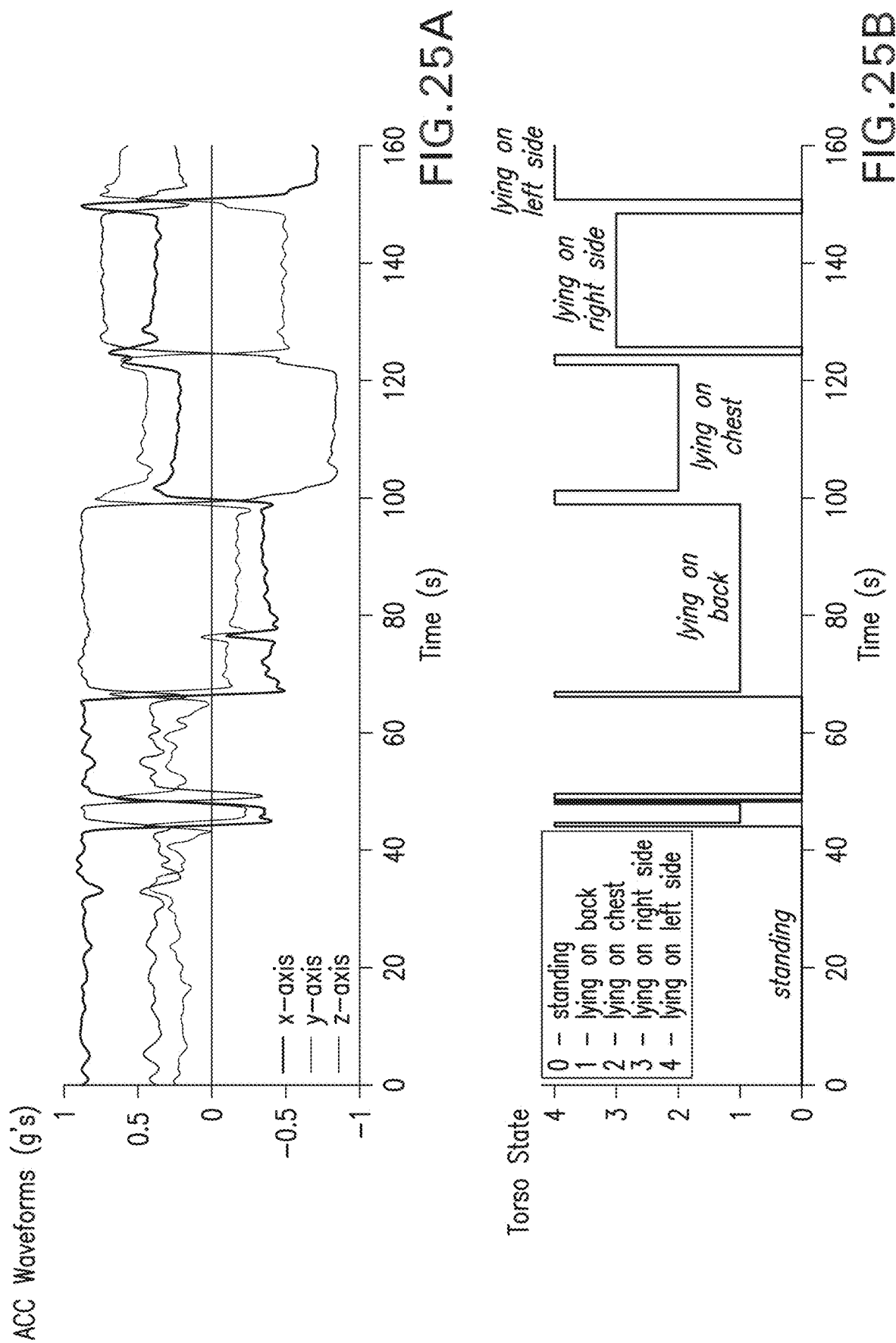
FIG. 25A shows a plot of time-dependent ACC waveforms measured from a patient's chest during different postures.
FIG. 25B shows a plot of time-dependent postures determined by processing the ACC waveforms of FIG. 25A with an algorithm and coordinate axis shown in FIG. 24.

FIGS. 25A-B show, for example, that the body-worn monitor can generate ACC waveforms that can be analyzed to accurately estimate the patient's posture. Specifically, FIG. 25A shows that the 3-axis accelerometer in the torso accurately measures ACC waveforms which correlate directly to the patient's position (e.g. standing, lying on back, lying on chest, lying on side) as indicated in FIG. 25B. This property, in turn, can be used along with the patient's SV/CO/CP value and a series of 'heuristic rules' to generate an alarm/alert value. For example, an alarm need not be sounded if the patient's SV/CO/CP value is low (e.g. below about 1.5 l/min. for CO), but analysis of the ACC waveforms indicates that the patient is standing or walking as shown in FIG. 25B. The assumption here is that a patient in this posture/activity level is not in need of medical assistance. In contrast, a combination of a low SV/CO/CP value and a patient that is either supine or, worse yet, recently fallen should trigger an alarm.

Figure 24:
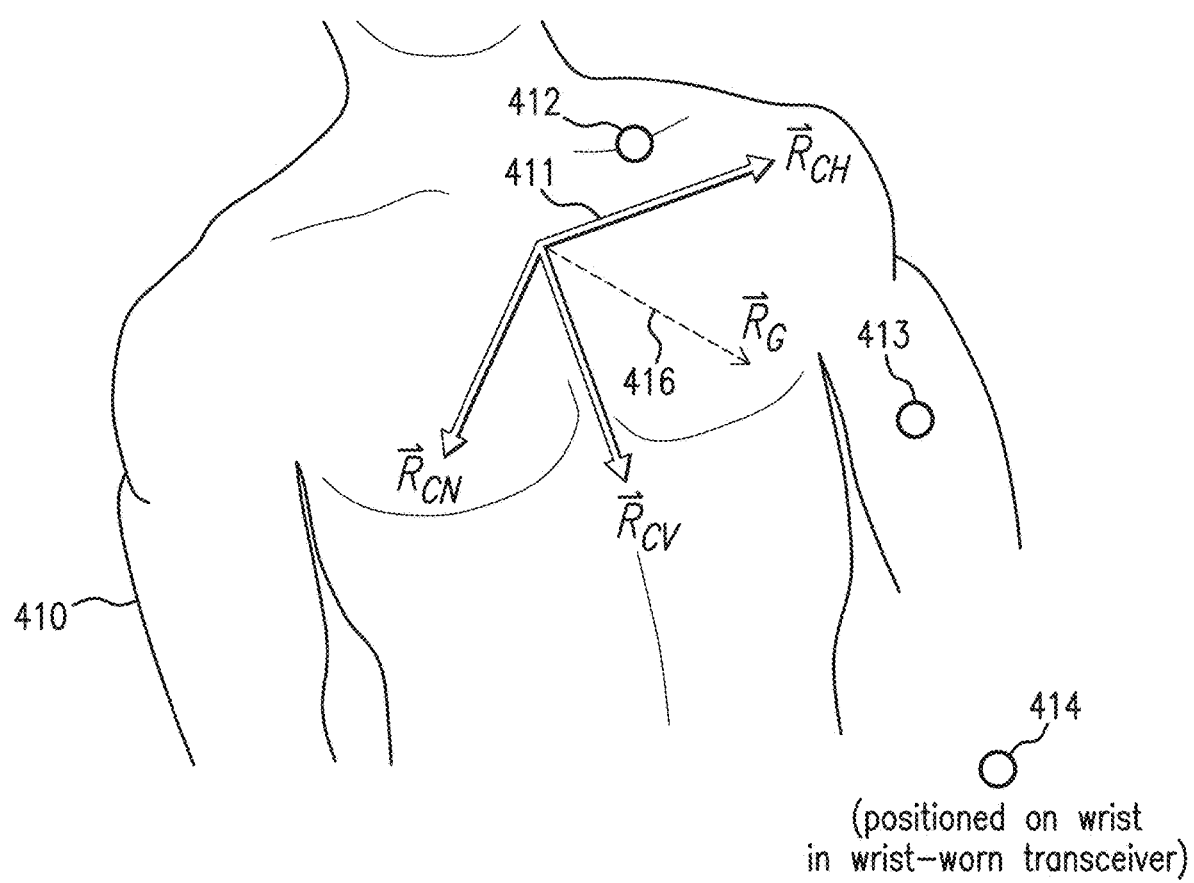
FIG. 24 shows a schematic drawing of a patient and an overlying coordinate axis used with an algorithm and ACC waveforms to determine the patient's posture.

FIG. 24 indicates how the body-worn monitor can determine motion-related parameters (e.g. degree of motion, posture, and activity level) from a patient 410 using time-dependent ACC waveforms continuously generated from the three accelerometers 412, 413, 414 worn, respectively, on the patient's chest, bicep, and wrist. Additionally, the height of the patient's arm can affect the cNIBP measurement, as blood pressure can vary significantly due to hydrostatic forces induced by changes in arm height. Moreover, this phenomenon can be detected and exploited to calibrate the cNIBP measurement, as described in detail in the above-referenced patent applications, the contents of which have been previously incorporated by reference. As described in these documents, arm height can be determined using DC signals from the accelerometers 413, 414 disposed, respectively, on the patient's bicep and wrist. Posture, in contrast, can be exclusively determined by the accelerometer 412 worn on the patient's chest. An algorithm operating on the wrist-worn transceiver extracts DC values from waveforms measured from this accelerometer and processes them with an algorithm described below to determine posture.

Specifically, torso posture is determined for a patient 410 using angles determined between the measured gravitational vector and the axes of a torso coordinate space 411. The axes of this space 411 are defined in a three-dimensional Euclidean space where $\vec{R}_{CV}$ is the vertical axis, $\vec{R}_{CH}$ is the horizontal axis, and $\vec{R}_{CN}$ is the normal axis. These axes must be identified relative to a 'chest accelerometer coordinate space' before the patient's posture can be determined.

The first step in determining a patient's posture is to identify alignment of $\vec{R}_{CV}$ in the chest accelerometer coordinate space. This can be determined in either of two approaches. In the first approach, $\vec{R}_{CV}$ is assumed based on a typical alignment of the body-worn monitor relative to a patient. During a manufacturing process, these parameters are then preprogrammed into firmware operating on the wrist-worn transceiver. In this procedure it is assumed that accelerometers within the body-worn monitor are applied to each patient with essentially the same configuration. In the second approach, $\vec{R}_{CV}$ is identified on a patient-specific basis. Here, an algorithm operating on the wrist-worn transceiver prompts the patient (using, e.g., video instruction operating on the wrist-worn transceiver, or audio instructions transmitted through a speaker) to assume a known position with respect to gravity (e.g., standing upright with arms pointed straight down). The algorithm then calculates $\vec{R}_{CV}$ from DC values corresponding to the x, y, and z-axes of the chest accelerometer while the patient is in this position. This case, however, still requires knowledge of which arm (left or right) the monitor is worn on, as the chest accelerometer coordinate space can be rotated by 180 degrees depending on this orientation. A medical professional applying the monitor can enter this information using the GUI, described above. This potential for dual-arm attachment requires a set of two pre-determined vertical and normal vectors that are interchangeable depending on the monitor's location. Instead of manually entering this information, the arm on which the monitor is worn can be easily determined following attachment using measured values from the chest accelerometer values, with the assumption that $\vec{R}_{CV}$ is not orthogonal to the gravity vector.

The second step in the procedure is to identify the alignment of $\vec{R}_{CN}$ in the chest accelerometer coordinate space. The monitor determines this vector in the same way it determines $\vec{R}_{CV}$ using one of two approaches. In the first approach the monitor assumes a typical alignment of the chest-worn accelerometer on the patient. In the second approach, the patient is prompted to the alignment procedure and asked to assume a known position with respect to gravity. The monitor then calculates $\vec{R}_{CN}$ from the DC values of the time-dependent ACC waveform.

The third step in the procedure is to identify the alignment of $\vec{R}_{CH}$ in the chest accelerometer coordinate space. This vector is typically determined from the vector cross product of $\vec{R}_{CV}$ and $\vec{R}_{CN}$, or it can be assumed based on the typical alignment of the accelerometer on the patient, as described above.

A patient's posture is determined using the coordinate system described above and in FIG. 24, along with a gravitational vector $\vec{R}_G$ 416 that extends normal from the patient's chest. The angle between $\vec{R}_{CV}$ and $\vec{R}_G$ is given by Eq. 7:

$$\theta_{VG}[n] = \arccos\left(\frac{\vec{R}_G[n] \cdot \vec{R}_{CV}}{\|\vec{R}_G[n]\|\|\vec{R}_{CV}\|}\right) \quad (7)$$

where the dot product of the two vectors is defined as:

$$\vec{R}_G[n] \cdot \vec{R}_{CV} = (y_{Cx}[n] \times r_{CVx}) + (y_{Cy}[n] \times r_{CVy}) + (y_{Cz}[n] \times r_{CVz}) \quad (8)$$

The definitions of the norms of $\vec{R}_G$ and $\vec{R}_{CV}$ are given by Eqs. 9 and 10:

$$\|\vec{R}_G[n]\| = \sqrt{(y_{Cx}[n])^2 + (y_{Cy}[n])^2 + (y_{Cz}[n])^2} \quad (9)$$

$$\|\vec{R}_{CV}\| = \sqrt{(r_{CVx})^2 + (r_{CVy})^2 + (r_{CVz})^2} \quad (10)$$

As indicated in Eq. 12, the monitor compares the vertical angle $\theta_{VG}$ to a threshold angle to determine whether the patient is vertical (i.e. standing upright) or lying down:

if $\theta_{VG} \leq 45°$ then Torso State=0, the patient is upright (11)

If the condition in Eq. 11 is met the patient is assumed to be upright, and their torso state, which is a numerical value equated to the patient's posture, is equal to 0. The patient is assumed to be lying down if $\theta_{VG} > 45$ degrees. Their lying position is then determined from angles separating the two remaining vectors, as defined below.

The angle $\theta_{NG}$ between $\vec{R}_{CN}$ and $\vec{R}_G$ determines if the patient is lying in the supine position (chest up), prone position (chest down), or on their side. Based on either an assumed orientation or a patient-specific calibration procedure, as described above, the alignment of $\vec{R}_{CN}$ is given by Eq. 11, where i, j, k represent the unit vectors of the x, y, and z axes of the chest accelerometer coordinate space respectively:

$$\vec{R}_{CN} = r_{CNx}\hat{i} + r_{CNy}\hat{j} + r_{CNz}\hat{k} \quad (12)$$

The angle between $\vec{R}_{CN}$ and $\vec{R}_G$ determined from DC values extracted from the chest ACC waveform is given by Eq. 13:

$$\theta_{NG}[n] = \arccos\left(\frac{\vec{R}_G[n] \cdot \vec{R}_{CN}}{\|\vec{R}_G[n]\|\|\vec{R}_{CN}\|}\right) \quad (13)$$

The body-worn monitor determines the normal angle $\theta_{NG}$ and then compares it to a set of predetermined threshold angles to determine which position in which the patient is lying, as shown in Eq. 14:

if $\theta_{NG} \leq 35°$ then Torso State=1, the patient is supine if $\theta_{NG} \geq 135°$ then Torso State=2, the patient is prone (14)

If the conditions in Eq. 14 are not met then the patient is assumed to be lying on their side. Whether they are lying on their right or left side is determined from the angle calculated between the horizontal torso vector and measured gravitational vectors, as described above.

The alignment of $\vec{R}_{CH}$ is determined using either an assumed orientation, or from the vector cross-product of $\vec{R}_{CV}$ and $\vec{R}_{CN}$ as given by Eq. 15, where i, j, k represent the unit vectors of the x, y, and z axes of the accelerometer coordinate space respectively. Note that the orientation of the calculated vector is dependent on the order of the vectors in the operation. The order below defines the horizontal axis as positive towards the right side of the patient's body.

$$\vec{R}_{CH} = r_{CVx}\hat{i} + r_{CVy}\hat{j} + r_{CVz}\hat{k} = \vec{R}_{CV} \times \vec{R}_{CN} \quad (15)$$

The angle $\theta_{HG}$ between $\vec{R}_{CH}$ and $\vec{R}_G$ is determined using Eq. 16:

$$\theta_{HG}[n] = \arccos\left(\frac{\vec{R}_G[n] \cdot \vec{R}_{CH}}{\|\vec{R}_G[n]\|\|\vec{R}_{CH}\|}\right) \quad (16)$$

The monitor compares this angle to a set of predetermined threshold angles to determine if the patient is lying on their right or left side, as given by Eq. 17:

if $\theta_{HG} \geq 90°$ then Torso State=3, the patient is on their right side if $\theta_{NG} < 90°$ then Torso State=4, the patient is on their left side (17)

Table 1 describes each of the above-described postures, along with a corresponding numerical torso state used to render, e.g., a particular icon on a remote computer:

TABLE 2 postures and their corresponding torso states

| Posture | Torso State |
| --- | --- |
| standing upright | 0 |
| supine: lying on back | 1 |
| prone: lying on chest | 2 |
| lying on right side | 3 |
| lying on left side | 4 |
| undetermined posture | 5 |

Data shown in FIGS. 25A, B were calculated using the above-mentioned approach. As the patient moves, the DC values of the ACC waveforms measured by the chest accelerometer vary accordingly, as shown in FIG. 25A. The body-worn monitor processes these values as described above to continually determine $\vec{R}_G$ and the various quantized torso states for the patient, as shown in FIG. 25B. The torso states yield the patient's posture as defined in Table 2. For this study the patient rapidly alternated between standing, lying on their back, chest, right side, and left side within a time period of about 160 seconds. Different alarm/alert conditions (e.g. threshold values) for vital signs can be assigned to each of these postures, or the specific posture itself may result in an alarm/alert. Additionally, the time-dependent properties of the graph can be analyzed (e.g. by counting changes in torso states) to determine, for example, how often the patient moves in their hospital bed. This number can then be equated to various metrics, such as a 'bed sore index' indicating a patient that is so stationary in their bed that lesions may result.

Alternate Embodiments

Figure 27:
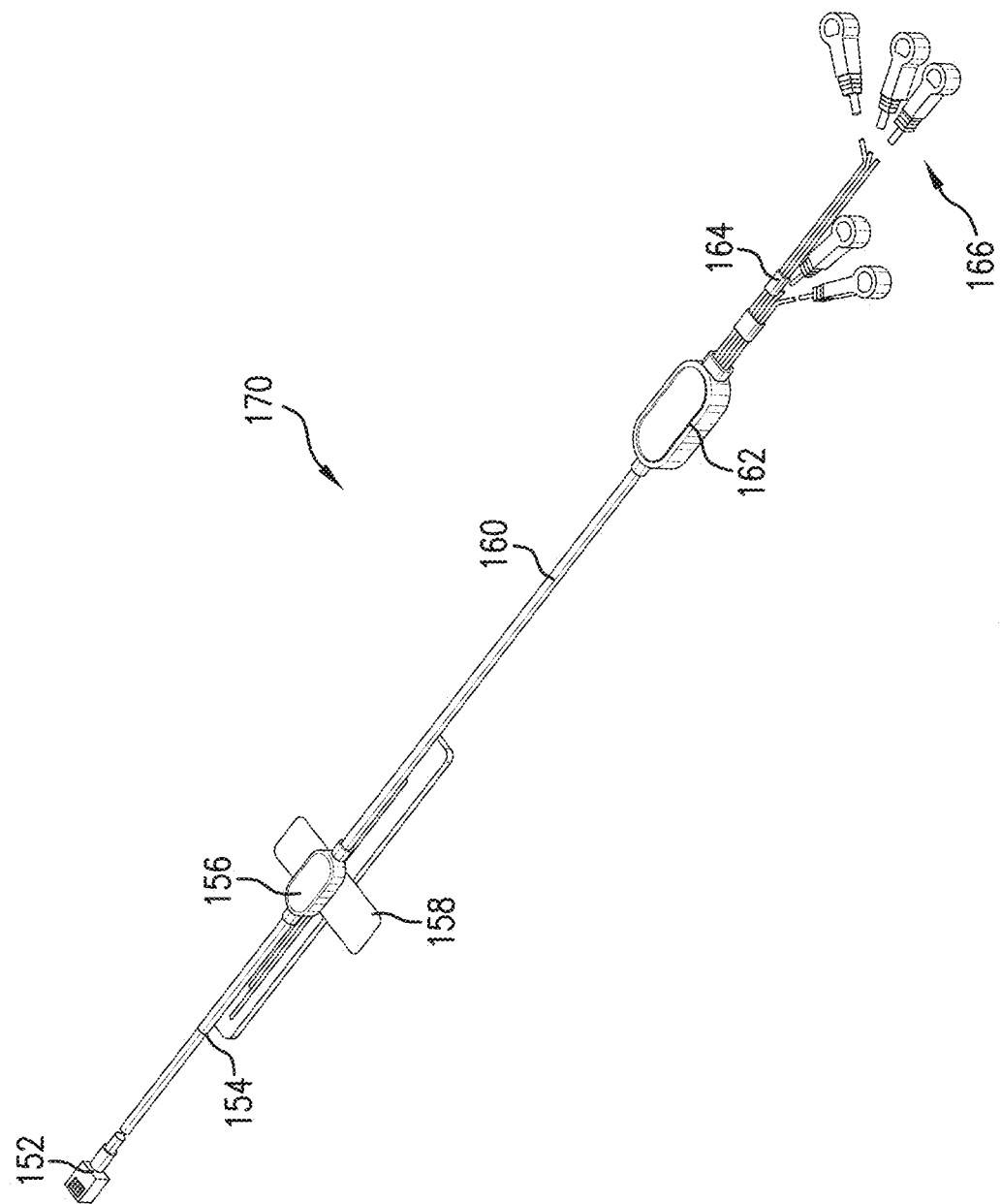
FIG. 27 shows a three-dimensional drawing of a harness used to make a TBEV measurement according to an alternate embodiment of the invention.

Other embodiments are within the scope of the invention. For example, the TBEV harness and its associated electrode can take on a variety of configurations. One of these is shown in FIG. 27. Here, the TBEV harness 170 features a TBEV module 156 disposed directly on top of a single TBEV electrode 158. The electrode 158 features four conductive regions (not shown in the figure): 1) a current source; 2) a current sink; and 3), 4) a pair of electrodes for measuring a voltage in the CB region. As described above, conductive regions for sourcing and draining the current are on an outer portion of the electrode 158, while those for measuring voltage are on an inner portion of the electrode. Each conductive region connects to analog circuitry within the TBEV module 156 with a single connector (not shown in the figure). The TBEV module 156 also includes a CAN transceiver (not shown in the figure) that sends digitized waveforms and CO/SV values through a first cable 154 to a connector 152 which plugs into the back panel of the wrist worn transceiver, such as that shown in FIG. 10. A second cable 160 connects to an ECG module 162, which in turn connects through a short third cable 164 to a collection of ECG leads 166. During a measurement, the ECG module 163 sends digitized versions of ECG waveforms, HR, and other information through the second cable 160 and to the TBEV module 156. Data are sent according to the CAN protocol. From there, data are relayed with the module's internal CAN transceivers through the second cable 154 and to the connector 152, which then passes the data onto the wrist transceiver.

Figure 28:
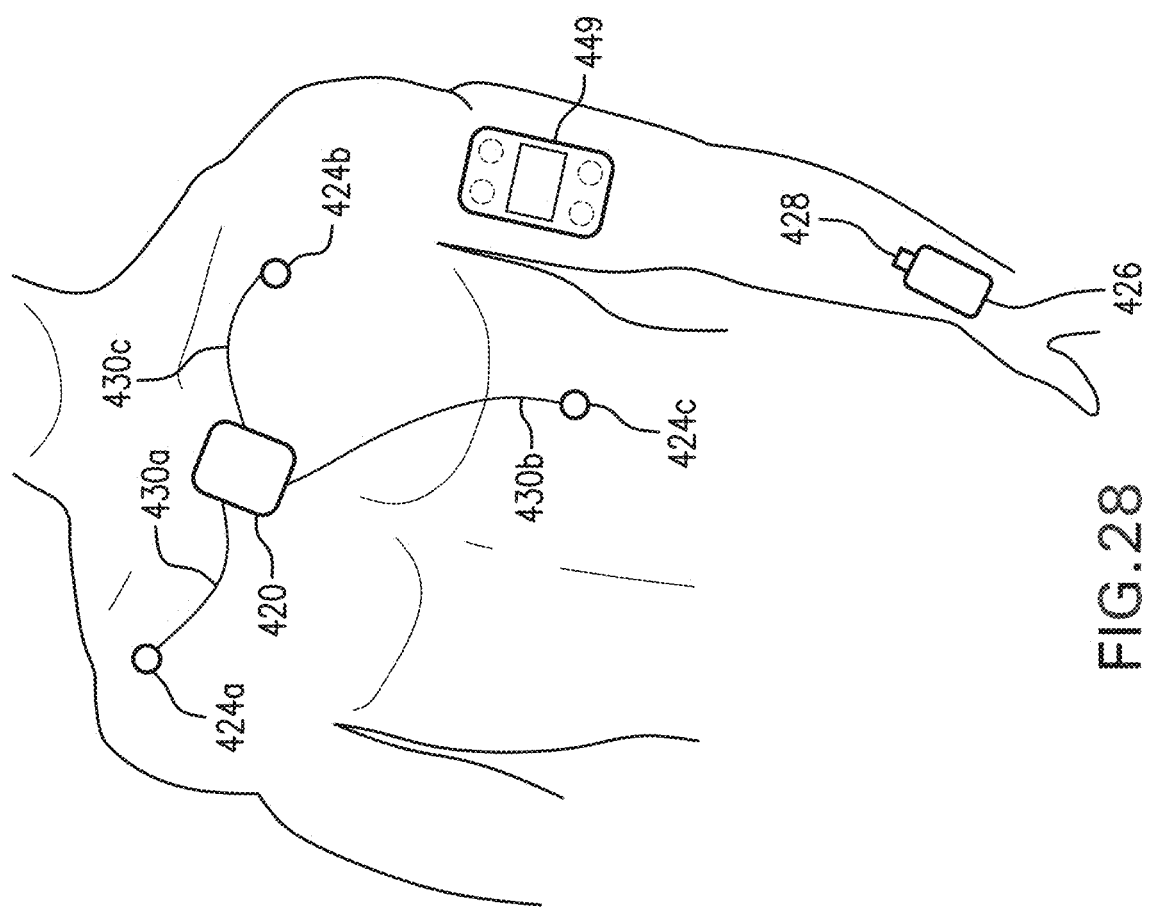
FIG. 28 shows a schematic drawing of an alternate embodiment of the invention wherein the TBEV circuit is contained within a module attached directly to the brachium and detached from the ECG circuit, which is worn on the chest.

FIG. 28 shows an alternate embodiment of the invention where TBEV 449 and ECG 420 modules are physically separated and connected through a wireless interface. Here, the ECG module 420 includes the ECG circuit, and attaches through cables 430a-c to ECG electrodes 424a-c. A second arm-worn module 449 includes four electrodes (two for injecting current; two for measuring voltage) dispersed on its upper and lower portions that connect to a central TBEV circuit to perform a measurement at the brachium as described above. Both the chest-worn module 420 and arm-worn module 449 include a unique Bluetooth transmitter that sends, respectively, ECG and TBEV waveforms to a paired Bluetooth transmitter 428 in the wrist-worn transceiver 426.

Figure 29:
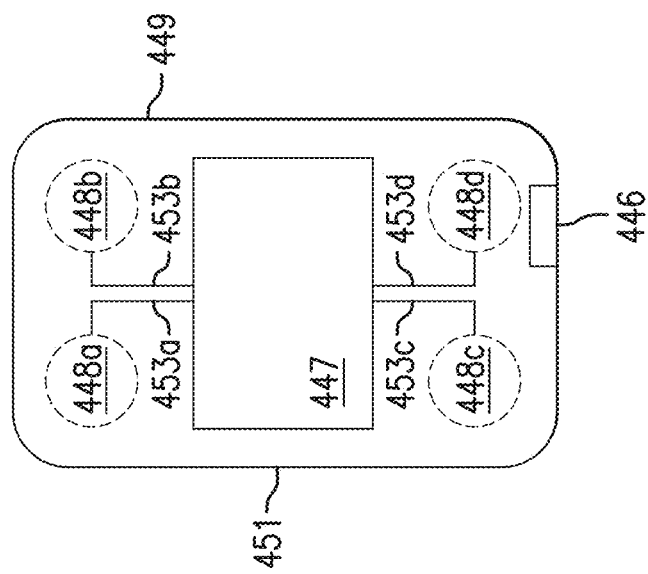
FIG. 29 shows a schematic drawing of the TBEV module shown in FIG. 28.

FIG. 29 shows the arm-worn module 449 in more detail. As described above, it includes four electrodes 448a-d that snap on to the back surface of a flexible substrate 451 that holds an TBEV circuit 447, located in the module's center in place. The electrodes 448a-d provide the current-injecting and voltage-measuring functions of the TBEV measurement as described above, and connect to the TBEV circuit 447 through a series of metal traces 453a-d embedded within the flexible substrate. The electrodes 448a-d also adhere to the patient's skin to hold the module 449 on the brachium. Once a TBEV waveform is measured, a Bluetooth transmitter 446 located at the bottom of the module sends it to the wrist-worn transceiver for processing, as described above.

Figure 30:
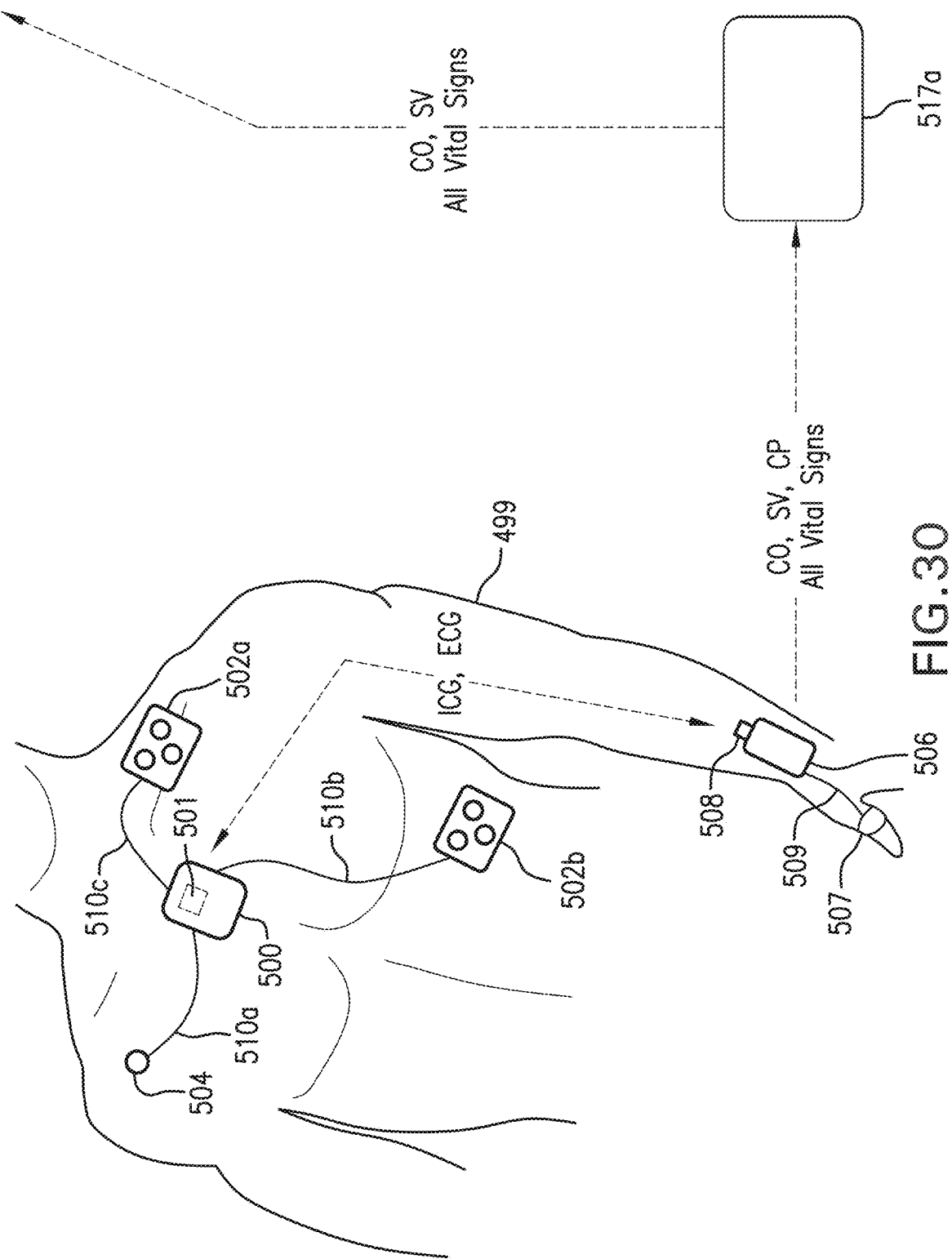
FIG. 30 shows a schematic drawing of an alternate embodiment of the invention wherein the body-worn monitor wirelessly transmits information between a chest-worn module and the wrist-worn transceiver, and from there to a remote monitor; and, FIG. 31 shows a schematic drawing of the body-worn monitor, similar to that shown in FIG. 30, that wirelessly transmits information between both a chest-worn module and the wrist-worn transceiver to the remote monitor.

FIGS. 30 and 31 show schematic drawings of an alternate embodiment of the invention, and indicate how data relating to SV/CP/CP can be wirelessly transmitted from the chest-worn sensor 500 and wrist-worn transceiver 506 to an external router (517 a in FIG. 30, 517 b in FIG. 31), and from there to an external network (e.g. the Internet). Multiple strategies can be used for this data-transfer process, two of which are shown in the figures. In FIG. 30, for example, the sensor 500 attaches through cables 510a-c to electrode patches 502 a, 502 b, and 504. ICG and ECG waveforms are measured from analog signals collected by electrode patches 502 a, 502 b, 504, and then wirelessly transmitted using Bluetooth module 501 from the chest-worn sensor 500 to the wrist-worn transceiver 506, where they are received using Bluetooth module 508 and then analyzed as described above to determine SV/CO/CP, along with all other vital signs. The wrist-worn transceiver 506 additionally connects through a short cable 509 that carries only analog signals measured by a thumb-worn optical sensor 507. These processed data are then sent from the transceiver 506 to the external router 517 a using Bluetooth, 802.11, or any other wireless protocol. Once the router 506 receives the data, it transmits it out using a wireless protocol (e.g. CDMA, GSM, iDEN) or wired protocol (e.g. Ethernet) to the external network. From there, for example, the data can be transferred to a hospital medical records systems, website, or sent through a web service to another application.

FIG. 31 shows an alternate approach where the external router 517b performs a higher degree of the computing load. In this case, the chest-worn sensor 500 processes analog signals measured by the electrode patches 502a, 502b, 504 to determine ECG and ICG waveforms, and then wirelessly transmits these in a digital form to the router 517*b*. At around the same time, the wrist-worn transceiver measures SpO2 and PPG waveforms and wirelessly transmits these to the router 517*b*. There, an embedded processor analyzes ECG waveforms to determine HR; ECG and PPG waveforms to determine PAT and cNIBP; and ECG, ICG, PPG waveforms and PAT to determine SV/CO/CP. These data are then transmitted as described above to the external network, and from there to another system.

In addition to those methods described above, the body-worn monitor can use a number of additional methods to calculate blood pressure and other properties from the optical and electrical waveforms. These are described in the following co-pending patent applications, the contents of which are incorporated herein by reference: 1) CUFFLESS BLOOD-PRESSURE MONITOR AND ACCOMPANYING WIRELESS, INTERNET-BASED SYSTEM (U.S. Ser. No. 10/709,015; filed Apr. 7, 2004); 2) CUFFLESS SYSTEM FOR MEASURING BLOOD PRESSURE (U.S. Ser. No. 10/709,014; filed Apr. 7, 2004); 3) CUFFLESS BLOOD PRESSURE MONITOR AND ACCOMPANYING WEB SERVICES INTERFACE (U.S. Ser. No. 10/810,237; filed Mar. 26, 2004); 4) VITAL SIGN MONITOR FOR ATHLETIC APPLICATIONS (U.S.S.N; filed Sep. 13, 2004); 5) CUFFLESS BLOOD PRESSURE MONITOR AND ACCOMPANYING WIRELESS MOBILE DEVICE (U.S. Ser. No. 10/967,511; filed Oct. 18, 2004); 6) BLOOD PRESSURE MONITORING DEVICE FEATURING A CALIBRATION-BASED ANALYSIS (U.S. Ser. No. 10/967,610; filed Oct. 18, 2004); 7) PERSONAL COMPUTER-BASED VITAL SIGN MONITOR (U.S. Ser. No. 10/906,342; filed Feb. 15, 2005); 8) PATCH SENSOR FOR MEASURING BLOOD PRESSURE WITHOUT A CUFF (U.S. Ser. No. 10/906,315; filed Feb. 14, 2005); 9) PATCH SENSOR FOR MEASURING VITAL SIGNS (U.S. Ser. No. 11/160,957; filed Jul. 18, 2005); 10) WIRELESS, INTERNET-BASED SYSTEM FOR MEASURING VITAL SIGNS FROM A PLURALITY OF PATIENTS IN A HOSPITAL OR MEDICAL CLINIC (U.S. Ser. No. 11/162,719; filed Sep. 9, 2005); 11) HAND-HELD MONITOR FOR MEASURING VITAL SIGNS (U.S. Ser. No. 11/162,742; filed Sep. 21, 2005); 12) CHEST STRAP FOR MEASURING VITAL SIGNS (U.S. Ser. No. 11/306,243; filed Dec. 20, 2005); 13) SYSTEM FOR MEASURING VITAL SIGNS USING AN OPTICAL MODULE FEATURING A GREEN LIGHT SOURCE (U.S. Ser. No. 11/307,375; filed Feb. 3, 2006); 14) BILATERAL DEVICE, SYSTEM AND METHOD FOR MONITORING VITAL SIGNS (U.S. Ser. No. 11/420,281; filed May 25, 2006); 15) SYSTEM FOR MEASURING VITAL SIGNS USING BILATERAL PULSE TRANSIT TIME (U.S. Ser. No. 11/420,652; filed May 26, 2006); 16) BLOOD PRESSURE MONITOR (U.S. Ser. No. 11/530,076; filed Sep. 8, 2006); 17) TWO-PART PATCH SENSOR FOR MONITORING VITAL SIGNS (U.S. Ser. No. 11/558,538; filed Nov. 10, 2006); and, 18) MONITOR FOR MEASURING VITAL SIGNS AND RENDERING VIDEO IMAGES (U.S. Ser. No. 11/682,177; filed Mar. 5, 2007).

Other embodiments are also within the scope of the invention. For example, other measurement techniques, such as conventional oscillometry measured during deflation, can be used to determine SYS for the above-described algorithms. Additionally, processing units and probes for measuring SpO2 similar to those described above can be modified and worn on other portions of the patient's body. For example, optical sensors with finger-ring configurations can be worn on fingers other than the thumb. Or they can be modified to attach to other conventional sites for measuring SpO2, such as the ear, forehead, and bridge of the nose. In these embodiments the processing unit can be worn in places other than the wrist, such as around the neck (and supported, e.g., by a lanyard) or on the patient's waist (supported, e.g., by a clip that attaches to the patient's belt). In still other embodiments the probe and processing unit are integrated into a single unit.

In other embodiments, a set of body-worn monitors can continuously monitor a group of patients, wherein each patient in the group wears a body-worn monitor similar to those described herein. Additionally, each body-worn monitor can be augmented with a location sensor. The location sensor includes a wireless component and a location-processing component that receives a signal from the wireless component and processes it to determine a physical location of the patient. A processing component (similar to that described above) determines from the time-dependent waveforms at least one vital sign, one motion parameter, and an alarm parameter calculated from the combination of this information. A wireless transceiver transmits the vital sign, motion parameter, location of the patient, and alarm parameter through a wireless system. A remote computer system featuring a display and an interface to the wireless system receives the information and displays it on a user interface for each patient in the group.

In embodiments, the interface rendered on the display at the central nursing station features a field that displays a map corresponding to an area with multiple sections. Each section corresponds to the location of the patient and includes, e.g., the patient's vital signs, motion parameter, and alarm parameter. For example, the field can display a map corresponding to an area of a hospital (e.g. a hospital bay or emergency room), with each section corresponding to a specific bed, chair, or general location in the area. Typically the display renders graphical icons corresponding to the motion and alarm parameters for each patient in the group. In other embodiments, the body-worn monitor includes a graphical display that renders these parameters directly on the patient.

Typically the location sensor and the wireless transceiver operate on a common wireless system, e.g. a wireless system based on 802.11 (i.e. 'WiFi'), 802.15.4 (i.e. 'Bluetooth'), or cellular (e.g. CDMA, GSM) protocols. In this case, a location is determined by processing the wireless signal with one or more algorithms known in the art. These include, for example, triangulating signals received from at least three different base stations, or simply estimating a location based on signal strength and proximity to a particular base station. In still other embodiments the location sensor includes a conventional global positioning system (GPS) that processes signals from orbiting satellites to determine patient's position.

The body-worn monitor can include a first voice interface, and the remote computer can include a second voice interface that integrates with the first voice interface. The location sensor, wireless transceiver, and first and second voice interfaces can all operate on a common wireless system, such as one of the above-described systems based on 802.11 or cellular protocols. The remote computer, for example, can be a monitor that is essentially identical to the monitor worn by the patient, and can be carried or worn by a medical professional. In this case the monitor associated with the medical professional features a GUI wherein the user can select to display information (e.g. vital signs, location, and alarms) corresponding to a particular patient. This monitor can also include a voice interface so the medical professional can communicate directly with the patient.

Still other embodiments are within the scope of the following claims.

What is claimed is:

1. A system for simultaneously measuring blood pressure and stroke volume of a patient, comprising:
    an impedance sensor comprising at least two electrodes and an impedance circuit, the at least two electrodes configured to be positioned on the patient in the clavicle/brachial region, and the impedance circuit configured to receive and process signals from the at least two electrodes to measure a transbrachial electro-velocimetry (TBEV) signal from the patient;
    an optical sensor configured to be positioned on the patient and comprising an optical probe configured to be positioned on a digit on a hand of the patient and an optical circuit, the optical circuit configured to receive and process signals from the optical probe to measure at least one optical signal from the patient;
    an ECG sensor configured to be positioned on the patient and comprising at least two electrodes configured to be positioned on the patient's torso and an ECG circuit, the ECG circuit configured to receive and process signals from the at least two electrodes to measure an ECG signal from the patient; and,
    a processing system configured to: (i) be worn on the patient's body; (ii) be operably connected to the impedance sensor, optical sensor, and the ECG sensor; (iii) receive the TBEV signal from the impedance sensor; (iv) receive the at least one optical signal from the optical sensor; (v) receive the ECG signal from the ECG sensor and collectively process the ECG signal and the at least one optical signal to determine a blood pressure value; (vi) process the TBEV signal to determine a time dependent derivative of the TBEV signal (d(TBEV)dZ/dt), a first zero value in d(TBEV)dZ/dt indicating onset of a pulse in d(TBEV)dZ/dt representing opening of the patient's aortic valve, a second zero value in d(TBEV)dZ/dt after onset of the pulse indicating closing of the patient's aortic valve, a d(TBEV)dZ/dt$_{max}$ value; (vii) determine a first systolic flow time (SFT) calculated using the first zero value in d(TBEV)dZ/dt and the second zero value in d(TBEV)dZ/dt; (viii) collectively process d(TBEV)dZ/dt$_{max}$ and the first SFT value to determine a first stroke volume (SV) value; (ix) process the at least one optical signal to determine a second SFT value; (x) collectively process d(TBEV)dZ/dt$_{max}$ and the second SFT value to determine a second SV value; (xi) collectively process the first and second SV values to determine a third SV value; and (xii) display the third SV value on a display device.

2. The system of claim 1, wherein the processing system is further configured to determine a time difference between the ECG signal and the at least one optical signal.

3. The system of claim 2, wherein the processing system is further configured to determine a pulse arrival time separating a QRS complex in the ECG signal and an onset of a pulse in the at least one optical signal.

4. The system of claim 3, wherein the processing system is further configured to process the pulse arrival time and a blood pressure calibration to determine a blood pressure value.

5. The system of claim 1, wherein the processing system is further configured to determine a time difference between the ECG signal and the TBEV signal.

6. The system of claim 5, wherein the processing system is further configured to determine a pulse arrival time separating a QRS complex in the ECG signal and an onset of a pulse in the TBEV signal.

7. The system of claim 6, wherein the processing system is further configured to process the pulse arrival time and a blood pressure calibration to determine a blood pressure value.

8. The system of claim 1, wherein the processing system is further configured to determine a time difference between the TBEV signal and the at least one optical signal.

9. The system of claim 8, wherein the processing system is further configured to determine a pulse transit time separating an onset of a first pulse in the TBEV signal and an onset of a second pulse in the at least one optical signal.

10. The system of claim 9, wherein the processing system is further configured to process the pulse transit time and a blood pressure calibration to determine a blood pressure value.

11. The system of claim 1, wherein the processing system is further configured to determine the second stroke volume value based on a contour of a pulse in the at least one optical signal.

* * * * *